United States Patent
Wang et al.

(10) Patent No.: US 10,039,797 B2
(45) Date of Patent: *Aug. 7, 2018

(54) METHODS OF IDENTIFYING AND QUANTIFYING SPHINGOLIPIDS

(71) Applicant: Macau University of Science and Technology, Taipa (MO)

(72) Inventors: Jing-Rong Wang, Taipa (MO); Jia-Ning Mi, Taipa (MO); Zhi-Hong Jiang, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 66 days.

This patent is subject to a terminal disclaimer.

(21) Appl. No.: 15/131,243

(22) Filed: Apr. 18, 2016

(65) Prior Publication Data

US 2017/0131300 A1    May 11, 2017

Related U.S. Application Data

(60) Provisional application No. 62/251,195, filed on Nov. 5, 2015.

(51) Int. Cl.
| | | |
|---|---|---|
| *A61K 36/068* | (2006.01) | |
| *A61K 31/133* | (2006.01) | |
| *A61K 31/164* | (2006.01) | |
| *A61K 31/688* | (2006.01) | |
| *B01D 15/42* | (2006.01) | |
| *C12Q 1/04* | (2006.01) | |
| *G01N 30/02* | (2006.01) | |
| *G01N 30/72* | (2006.01) | |
| *G01N 33/92* | (2006.01) | |

(52) U.S. Cl.
CPC .......... *A61K 36/068* (2013.01); *A61K 31/133* (2013.01); *A61K 31/164* (2013.01); *A61K 31/688* (2013.01); *B01D 15/426* (2013.01); *C12Q 1/04* (2013.01); *G01N 30/72* (2013.01); *G01N 33/92* (2013.01); *A61K 2236/333* (2013.01); *A61K 2236/39* (2013.01); *A61K 2236/50* (2013.01); *A61K 2236/53* (2013.01); *G01N 2030/027* (2013.01); *G01N 2333/37* (2013.01); *G01N 2405/08* (2013.01)

(58) Field of Classification Search
CPC .......... A61K 2236/333; A61K 2236/39; A61K 2236/50; A61K 2236/53; A61K 31/133; A61K 31/164; A61K 31/688; A61K 36/068; A61K 2039/5158; A61K 2039/55505; A61K 2039/55566; A61K 2039/6006; A61K 39/0011; A61K 39/0225; A61K 2300/00; A61K 31/7008; A61K 36/9068; A61K 2236/30; A61K 31/7024; A61K 31/7028; A61K 31/7032; B01D 15/426; C12Q 1/04; G01N 2030/027; G01N 2333/37; G01N 2405/08; G01N 30/72; G01N 33/92
See application file for complete search history.

(56) References Cited

PUBLICATIONS

Zhu, J. S.; Halpern, G. S. M.; Jones, K. H. The scientific rediscovery of an ancient Chinese herbal medicine: Cordyceps sinensis Part I. J. Altern. Complem. Med. 1998, 4 (3), 289-303.

Zhu, J. S.; Halpern, G. S. M.; Jones, K. H. The scientific rediscovery of a precious ancient Chinese herbal regimen: Cordyceps sinensis Part II. J. Altern. Complem. Med. 1998, 4 (4), 429-457.

Yao X. L.; Meran S.; Fang Y. P.; Martin J.; Midgley A.; Pan M. M.; Liu B. C.; Cui S. W.; Phillips G. O.; Phillips A. O. Cordyceps sinensis: In vitro anti-fibrotic bioactivity of natural and cultured preparations. Food Hydrocolloid. 2014, 35, 444-452.

Yan X. F.; Zhang Z. M.; Yao H. Y.; Guan Y.; Zhu J. P.; Zhang L. H.; Jia Y. L. and Wang R. W. Cardiovascular protection and antioxidant activity of the extracts from the mycelia of Cordyceps sinensis act partially via adenosine receptors. Phytother. Res. 2013, 27, 1597-1604.

Zhou X.; Gong Z.; Su Y.; Lin J.; Tang K. *Cordyceps fungi*: natural products, pharmacological functions and developmental products. J. Pharm. Pharmacol. 2009, 61, 279-291.

Fujita, T.; Inoue, K.; Yamamoto, S.; Ikumoto, T.; Sasaki, S.; Toyama, R.; Chiba, K.; Hoshino, Y.; Okumoto, T. Fungal metabolites. Part 11. A potent immunosuppressive activity found in Isaria sinclairii metabolite. J. Antibiot. 1994, 47, 208-215.

Fahy E.; Subramaniam S.; Brown H. A.; Glass C. K.; Merrill, A. H., Jr.; Robert C. Murphy R. C.; Raetz C. R. H.; Russell D. W.; Seyama Y.; Shaw W.; Shimizu T.; Spener F.; Meer G. V.; Nieuwenhze M. S. V.; White S. H.; Witztum J. L. and Dennis E. A. A comprehensive classification system for lipids. J. Lipid Res. 2005, 46, 839-861.

Schwartz, G. K.; Ward, D.; Saltz, L.; Casper, E. S.; Spiess, T.; Mullen, E.; Woodworth, J.; Venuti, R.; Zervos, P.; Storniolo, A. M.; Kelsen, D. P. A pilot clinical/pharmacological study of the protein kinase C-specific inhibitor safingol alone and in combination with doxorubicin. Clin. Cancer Res. 1997, 3, 537-543.

Coward, J.; Ambrosini, G.; Musi, E.; Truman, J. P.; Haimovitz-Friedman, A.; Allegood, J. C.; Wang, E.; Merrill, A. H., Jr.; Schwartz, G. K. Safingol (L-threo-sphinganine) induces autophagy in solid tumor cells through inhibition of PKC and the PI3-kinase pathway. Autophagy 2009, 5, 184-193.

Schoffski, P.; Dumez, H.; Ruijter, R.; Miguel-Lillo, B.; Soto-Matos, A.; Alfaro, V.; Giaccone, G. Spisulosine (ES-285) given as a weekly three-hour intravenous infusion: results of a phase I dose-escalating study in patients with advanced solid malignancies. Cancer Chemoth. Pharm. 2011, 68, 1397-1403.

Baird, R. D.; Kitzen, J.; Clarke, P. A.; Planting, A.; Reade, S.; Reid, A.; Welsh, L.; Lopez Lazaro, L.; de las Heras, B.; Judson, I. R.; Kaye, S. B.; Eskens, F.; Workman, P.; deBono, J. S.; Verweij, J. Phase I safety, pharmacokinetic, and pharmacogenomic trial of ES-285, a novel marine cytotoxic agent, administered to adult patients with advanced solid tumors. Mol. Cancer Ther. 2009, 8, 1430-1437.

(Continued)

*Primary Examiner* — Debbie K Ware

(74) *Attorney, Agent, or Firm* — Renner Kenner Greive Bobak Taylor & Weber

(57) ABSTRACT

A method of identifying and preferably quantifying at least one sphingolipid, in particular the sphingolipid portion in wild-type *Cordyceps* or *Cordyceps* derivates includes preparing a test sample solution from a *Cordyceps* sample, subjecting the test sample solution to liquid chromatrography with a mobile phase including at least a first and second eluting solvent; and performing a mass spectrometry after the step of subjecting. The quality and safety of *Cordyceps* products can be determined and wild-type *Cordyceps* and *Cordyceps* derivates may be differentiated via the ratio and/or presence of certain sphingolipids especially suitable as markers.

20 Claims, 14 Drawing Sheets

(56) References Cited

PUBLICATIONS

Bieberich, E.; Kawaguchi, T.; Yu, R. K. N-acylated serinol is a novel ceramide mimic inducing apoptosis in neuroblastoma cells. J. Biol. Chem. 2000, 275, 177-181.

Stover, T. C.; Sharma, A.; Robertson, G. P.; Kester, M. Systemic delivery of liposomal short-chain ceramide limits solid tumor growth in murine models of breast adenocarcinoma. Clin. Cancer Res. 2005, 11, 3465-3474.

Exon, J. H.; South, E. H. Effects of sphingomyelin on aberrant colonic crypt foci development, colon crypt cell proliferation and immune function in an aging rat tumor model. Food Chem. Toxicol. 2003, 41, 471-476.

Wang, J. R.; Zhang, H.; Yau, L. F.; Mi, J. N.; Lee, S.; Lee, K. C.; Hu, P.; Liu, L.; Jiang, Z. H. Improved sphingolipidomic approach based on ultra-high performance liquid chromatography and multiple mass spectrometries with application to cellular neurotoxicity. Anal. Chem. 2014, 86, 5688-5696.

METHODS OF IDENTIFYING AND QUANTIFYING SPHINGOLIPIDS

TECHNICAL FIELD

The present invention relates to a method of identifying and preferably quantifying at least one sphingolipid in wild-type *Cordyceps* and *Cordyceps* derivates. A further aspect relates to a method of identifying wild-type *Cordyceps* in a *Cordyceps* sample as well as of identifying *Cordyceps* derivates in a *Cordyceps* sample, namely for differentiating between wild-type *Cordyceps* and *Cordyceps* derivates.

BACKGROUND OF THE INVENTION

Wild-type *Cordyceps* is a composite consisting of stroma of a fungus that grows on a dead caterpillar whose larva is the primary host of the fungus, which is also known as caterpillar fungus. More specifically, wild-type *Cordyceps* grows in a natural environment and mainly consists of stroma of *Cordyceps sinensis* [Berk.] Sacc. (family Hypocreaceae) and a dead caterpillar of *Hepialus armoricanus* (family Hepialidae). It is one of the most famous and most expensive traditional Chinese medicinal materials. It is restrictedly distributed in alpine habitats on the Tibetan Plateau in China.

Wild-type *Cordyceps* proved to have various therapeutic effects on the renal system, the respiratory system and the immune system. For example, those effects include: tonifying the kidney, replenishing the lung, stanching bleeding and resolving phlegm and mucus. *Cordyceps* has been historically used for the treatments of hyposexualities, hyperglycemia, hyperlipidemia, asthenia, respiratory disease, and renal dysfunction, etc. (e.g. Zhu, J. S. et al., J. Altern. Complem. Med. 1998, 4 (3), 289-303; and Zhu, J. S. et al., J. Altern. Complem. Med. 1998, 4 (4), 429-457). In addition to the medical applications, *Cordyceps* is also widely utilized as a tonic and functional food in China (Zhu, J. S. et al. J. Altern. Complem. Med. 1998, 4 (3), 289-303).

The broad spectrum of pharmacological effects of wild-type *Cordyceps* has led to an ever-increasing demand on this herbal medicine whose natural resource is increasingly scarce. To meet the increasing demands of wild-type *Cordyceps*, several products based on fungi or mycelia isolated from wild-type *Cordyceps* and being artificially cultured have been developed and manufactured in large quantities in particular by using fermentation technology. Five of such alternative products have been approved so far as drugs by the China Food and Drug Administration (CFDA), comprising *Cordyceps sinensis, Hirsutella sinensis, Cephalosporium sinensis, Mortierella* SP and *Gliocadium roseum*. According to the data from the National Bureau of Statistics of China, the annual production of these mycelia was over 3000 tons in 2011, demonstrating a wide application and recognized therapeutic effects of these mycelial products. As alternatives of wild-type *Cordyceps*, *Cordyceps* derivates have been substantially investigated for their pharmacological effects. Studies have shown that the mycelial component could invigorate the lung and nourish kidney, improve the heart health and the liver health, as well as strengthen the immune system, etc. (for example Weng C. M., Chin. J. Inf. Tradit. Chin. Med. 2000, 7 (4), 75-76 or Wang Z. H. et al., Chin. J. Clin. Med. 2003, 3 (8), 681-682). Usually different conditions for culturing the fungi or mycelial strains are applied for production of these derivates, wherein variations in fermentation time, temperature and culture medium could be accompanied by differences in the ingredients which, thus, make quality and quantity control to very important means for ensuring safety and efficacy of a treatment with *Cordyceps*.

However, comprehensive studies on chemical constituents of wild-type *Cordyceps* compared to the above mentioned products based on isolated and artificially cultured fungi or mycelia are still absent. Currently, nucleosides, mannitol and amino acids which are, however, not the specific constituents of either the derivates or wild-type *Cordyceps* were used as markers for the quality control. In addition, the reported bioactivities of the above constituents are not fully responsible for the observed effects. The aforesaid non-specific constituents cannot reflect the true quality level of the wild-type *Cordyceps* and the above mentioned products being tested, let alone facilitate the identification and differentiation between wild-type *Cordyceps* and available alternative products. These limitations highlight the importance of identifying more specific and active constituents which can be used for quality control and thus methods allowing for identifying of and differentiating between wild-type *Cordyceps* and the mentioned alternative products.

Sphingolipids (SPLs) are a complex family of compounds that share a common structural feature, i.e. a sphingoid base backbone which could be biosynthesized from serine and a long-chain fatty acyl-CoA. The sphingoid base backbone can be subsequently converted into ceramides, phosphosphingolipids, glycosphingolipids and other subgroups of sphingolipids (Fahy, E. et al., J. Lipid Res. 2005, 46, 839-861).

In 1994, myriocin, a natural sphingolipid, was isolated from the culture broth of *Isaria sinclairii* (the imperfect stage of *Cordyceps sinclairii*) as a potent immunosuppressive constituent (Fujita, T. et al., J. Antibiot. 1994, 47, 208-215). Starting from myriocin, FTY720 was synthesized and finally developed into a drug (Fingolimod) for the treatment of multiple sclerosis and organ transplantation. Thus, SPLs might be active constituents of wild-type *Cordyceps* and respective derivates. Further studies have demonstrated the crucial role of endogenous SPLs in various biological procedures. Specifically, the natural and chemically synthesized SPLs can exert significant bioactivities. For instance, sphingoid bases have been regarded as potential anticancer agents, as represented by safingol (Schwartz, G. K. et al., Clin. Cancer Res. 1997, 3, 537-543; Coward, J. et al., Autophagy 2009, 5, 184-193) and 1-deoxysphinganine (Schoffski, P. et al., Cancer Chemoth. Pharm. 2011, 68, 1397-1403; Baird, R. D. et al., Mol. Cancer Ther. 2009, 8, 1430-1437), both of which are being evaluated in phase I clinical trials. A recent study also suggested that structural analogues of ceramide (C16-serinol) and exogenous natural ceramide exhibit promising anticancer effects (Bieberich, E. et al., Biol. Chem. 2000, 275, 177-181; Stover, T. C. et al., Clin. Cancer Res. 2005, 11, 3465-3474). Additionally, there is evidence showing that sphingomyelin has effects on the post-initiation development of preneoplastic lesions in the rat colon (Exon, J. H., South, E. H., Food Chem. Toxicol. 2003, 41, 471-476). Although this suggests that natural SPLs are pharmacologically active constituents of natural medicines, there remain challenges in identifying SPLs in a natural material or products, especially in specifically profiling SPLs including low abundance ones while clearly differentiating between them for quality and quantitative control.

Accordingly, there remains a strong need for methods which allow for identifying and quantifying components such as in wild-type *Cordyceps* and alternative products in particular for identifying wild-type *Cordyceps* and differentiating between them and alternative products as means for ensuring quality and safety of the respective treatment with *Cordyceps*.

SUMMARY OF THE INVENTION

In one aspect, the present invention relates to a method of identifying and optionally quantifying, in particular identifying and quantifying, at least one sphingolipid in a *Cordyceps* sample. The *Cordyceps* sample comprises and preferably consists of wild-type *Cordyceps* or a *Cordyceps* derivate. In particular the sphingolipid portion in the *Cordyceps* sample is identified and preferably quantified.

The *Cordyceps* sample may be a biological sample, a commercially available product, a pharmaceutical composition or the like and preferably consists of wild-type *Cordyceps* or a *Cordyceps* derivate.

Said method comprises steps of:
a) preparing a test sample solution from the *Cordyceps* sample comprising a step of
(i) extracting the *Cordyceps* sample with at least a first extracting solvent, which extracting solvent comprises an aliphatic alcohol, in particular a monohydric aliphatic alcohol containing one to four carbon atoms such as methanol;
b) subjecting the test sample solution to liquid chromatography with a mobile phase comprising at least a first and a second eluting solvent, wherein the at least first and second eluting solvent comprise a mixture of at least one aliphatic alcohol, at least one carboxylic acid and at least one carboxylic acid salt and wherein the second eluting solvent has a higher total amount of aliphatic alcohol, namely total amount of the at least one aliphatic alcohol and of possible further aliphatic alcohols, in particular of the first and a second aliphatic alcohol, compared to the amount of aliphatic alcohol in the first eluting solvent; and
c) performing a mass spectrometry following step b).

In particular, step a) comprises:
(i) extracting the *Cordyceps* sample with the at least first extracting solvent comprising an aliphatic alcohol for obtaining a *Cordyceps* extract, in particular extracting the *Cordyceps* sample with a first, a second and a third extracting solvent, which first, second and third extracting solvents each comprise a monohydric aliphatic alcohol containing one to four carbon atoms for obtaining a *Cordyceps* extract;
(ii) reconstituting the *Cordyceps* extract with a reconstitution solvent; and
(iii) filtering the reconstituted *Cordyceps* extract for obtaining the test sample solution.

Preferably, coupled UHPLC-Q-TOF and/or coupled UHPLC-QQQ is applied in steps b) and c).

In a further aspect, there is provided a method of identifying wild-type *Cordyceps* in a *Cordyceps* sample. Said method comprises steps of:
a) identifying and quantifying a sphingolipid portion in a *Cordyceps* sample as described above;
b) determining at least a first and a second *Cordyceps* wild-type indicative parameter,
c) comparing the at least first and second *Cordyceps* wild-type indicative parameter with a respective reference value.

An at least first and second *Cordyceps* wild-type indicative parameter corresponding to the respective reference value indicates that the *Cordyceps* sample comprises or consists of wild-type *Cordyceps*. The first *Cordyceps* wild-type indicative parameter is the ratio of ceramides to sphingoid bases, wherein the reference value for the first *Cordyceps* wild-type indicative parameter is an amount of ceramides of at least 10 wt.-% and less than 100 wt.-% relative to the amount of sphingoid bases. The second *Cordyceps* wild-type indicative parameter is the ratio of glycosphingolipids to phosphosphingolipids and wherein the reference value for the second *Cordyceps* wild-type indicative parameter is an amount of glycosphingolipids which is at most 80 wt.-% relative to the amount of phosphosphingolipids. Preferably, further *Cordyceps* wild-type indicative parameters are determined and compared with respective reference values.

The present invention further refers to a method of identifying a *Cordyceps* derivate, namely a *Cordyceps* derivate referenced as *Cordyceps sinensis, Hirsutella sinensis, Cephalosporium sinensis, Mortierella* SP or *Gliocadium roseum* herein in a *Cordyceps* sample. Said method comprises identifying and/or quantifying at least one sphingolipid in a *Cordyceps* sample as described above including preferred embodiments described above, preferably identifying and quantifying at least one sphingolipid in a *Cordyceps* sample.

The method of identifying a *Cordyceps* derivate in a *Cordyceps* sample preferably comprises the steps of
a) identifying and quantifying at least one and preferably more than one sphingolipid in a *Cordyceps* sample as described above;
b) determining at least one *Cordyceps* derivate indicative parameter which is in particular the amount of a sphingolipid usually in pmol/mg of the *Cordyceps* sample, preferably more than one *Cordyceps* derivate indicative parameter, namely the amount of more than one sphingolipid;
c) comparing the *Cordyceps* derivate indicative parameter with a respective reference value;
wherein an at least one *Cordyceps* derivate indicative parameter corresponding to the respective reference value, in particular the presence of the sphingolipid(s) in respective amount(s) as respective reference value(s), indicates that the respective *Cordyceps* derivate is present in the *Cordyceps* sample.

Further contemplated by the present invention is a method for determining indicative parameters for wild-type *Cordyceps* (i.e. *Cordyceps* wild-type indicative parameters) or indicative for *Cordyceps* derivates (i.e. *Cordyceps* derivate indicative parameters), in particular presence, amount or ratio of certain sphingolipids as markers which method comprises:
a) identifying and quantifying at least one and preferably more than one sphingolipid in a first *Cordyceps* sample selected from a *Cordyceps* sample comprising wild-type *Cordyceps* or a *Cordyceps* sample comprising a first *Cordyceps* derivate;
b) identifying and quantifying said at least one and preferably more than one sphingolipid in a second *Cordyceps* sample of a second *Cordyceps* derivate;
c) optionally identifying and quantifying said at least one and preferably more than one sphingolipid in further *Cordyceps* samples each comprising further *Cordyceps* derivates;
d) comparing the presence of the at least one sphingolipid, preferably the sphingolipid pattern and/or the amount of the at least one sphingolipid or ratio of sphingolipids in the respective *Cordyceps* samples;
e) defining *Cordyceps* wild-type indicative parameters and/or *Cordyceps* derivate indicative parameters and respective reference values.

The *Cordyceps* wild-type indicative parameters and/or *Cordyceps* derivate indicative parameters defined in step e)

can be used for quality control and identification of wild-type *Cordyceps* or *Cordyceps* derivates in *Cordyceps* samples.

The method of the present invention of identifying and optionally quantifying at least one sphingolipid in a *Cordyceps* sample allows for an unambiguous identification of several and different groups of therapeutically important and even of low abundance sphingolipids. In particular the specific sample preparation and chromatographic and mass spectrometric conditions allow for identifying and quantifying about 101 sphingolipids in *Cordyceps* samples. Said method was, furthermore, fully validated.

Said method is highly advantageous and can in particular be applied to identify or differentiate wild-type *Cordyceps* from *Cordyceps* derivates referenced herein as *Cordyceps sinensis, Hirsutella sinensis, Cephalosporium sinensis, Mortierella* SP or *Gliocadium roseum*. Moreover, the methods of the present invention allow for conclusions regarding the quality and, thus, the safety of the *Cordyceps* sample. This is important as the inventors also found that there are remarkable differences between wild-type *Cordyceps* and *Cordyceps* derivates regarding several sphingolipids and respective amounts and ratios of sphingolipids can, thus, serve as markers and are especially suitable for identification of wild-type *Cordyceps*. Accordingly, the present invention provides potential parameters such as ratios or specific sphingolipids as markers for qualitative and quantitative analysis of *Cordyceps* samples. The potential parameters namely the sphingolipids are in particular active ingredients that specifically contribute to the therapeutic effects of *Cordyceps*. Said sphingolipids can, thus, also be isolated and used in a medicament for treatment and prevention of diseases.

BRIEF DESCRIPTION OF DRAWINGS

FIG. 7A shows linear correlation of the added and determined amount of So (d14:1). FIG. 7B shows linear correlation of the added and determined amount of So (d20:1). FIG. 7C shows linear correlation of the added and determined amount of Cer (d18:1/6:0). FIG. 7D shows linear correlation of the added and determined amount of Cer (d18:1/18:0). FIG. 7E shows linear correlation of the added and determined amount of Cer (d18:1/22:0). FIG. 7F shows linear correlation of the added and determined amount of Cer (d18:1/24:0). FIG. 7G shows linear correlation of the added and determined amount of SM (d18:1/17:0). FIG. 7H shows linear correlation of the added and determined amount of SM (d18:1/20:0). FIG. 7I shows linear correlation of the added and determined amount of Cer (d18:1/24:0).

DESCRIPTION OF THE INVENTION AND EMBODIMENTS

Figure 1:
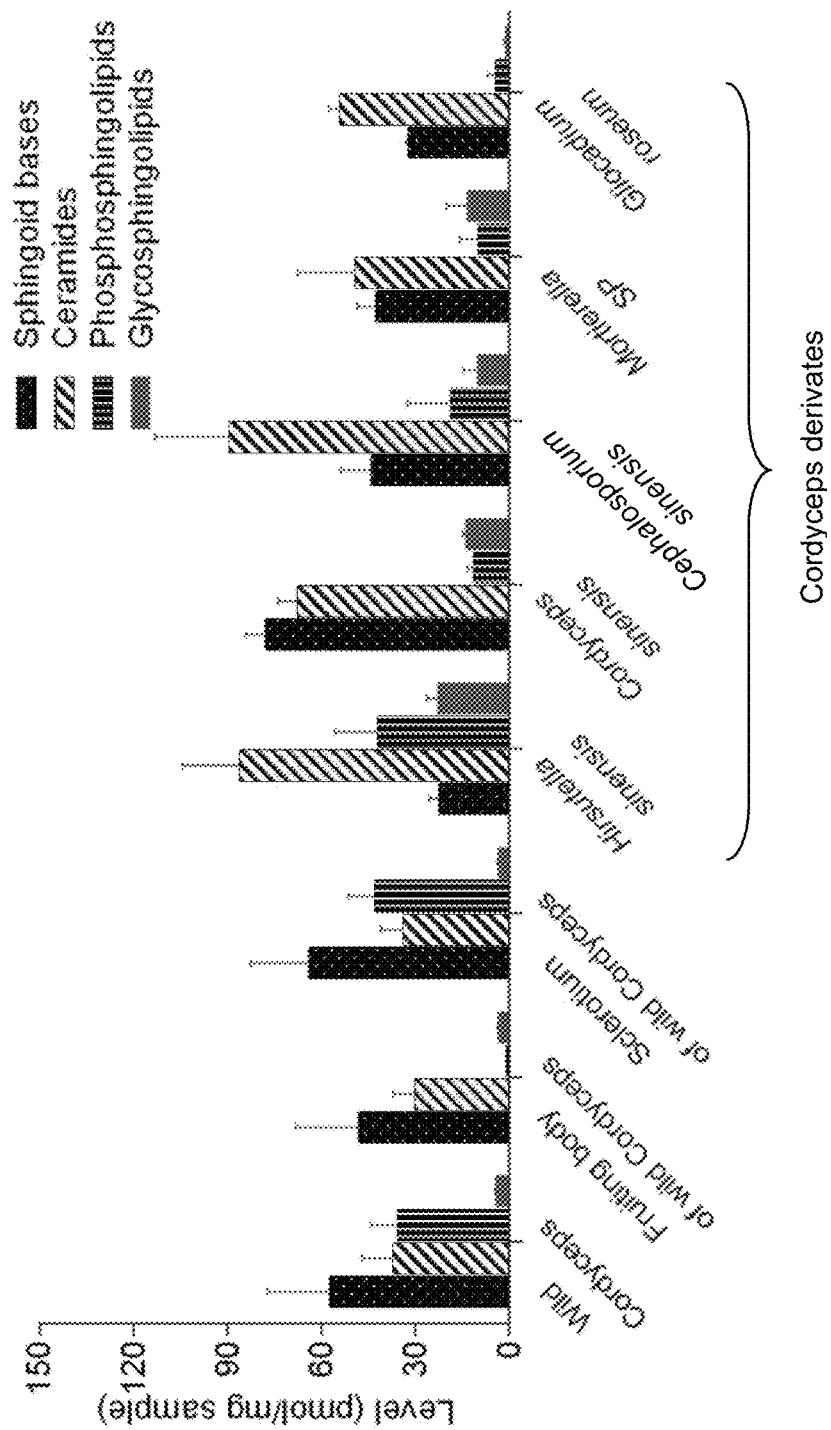
FIG. 1 shows the total levels of the subgroups of sphingolipids of the sphingolipid portion in the *Cordyceps* samples including a *Cordyceps* sample with wild-type *Cordyceps* (whole caterpillar fungus, also referenced as "wild *Cordyceps*"), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*. Each bar represents mean±SD.

The following embodiments and examples are given to enable those skilled in the art to more clearly understand and to practice the present invention. They should not be considered as limiting the scope of the invention, but merely as being illustrative and representing preferred embodiments thereof. The technical terms used in the present patent application have the meaning as commonly understood by a respective skilled person unless specifically defined otherwise.

In a first aspect, the present invention relates to a method of identifying and optionally quantifying at least one sphingolipid in a *Cordyceps* sample, i.e. a sample comprising and preferably consisting of *Cordyceps*. Said method is, thus, specifically applied to identify and optionally quantify at least one sphingolipid in *Cordyceps*.

The term "*Cordyceps*" used herein includes wild-type *Cordyceps* as well as *Cordyceps* derivates. The term "wild-type *Cordyceps*" is used for the naturally available and grown form of *Cordyceps*, namely the naturally available parasitic complex of a *Cordyceps* fungus with a caterpillar, namely and in the meaning of the present invention of the species *Cordyceps sinensis* (also known as *Ophiocordyceps sinensis*) with a caterpillar. Basically, the fungus infects the underground larva of one particular species of moth, *Hepialus armoricanus* and occasionally other species, grows and gradually changes into a fruiting body.

The term "*Cordyceps* derivates" as used herein means fungi in particular mycelia derived from wild-type *Cordyceps* in particular obtained by artificial cultivation of mycelia isolated from wild-type *Cordyceps* such as respective anamorphs of wild-type *Cordyceps sinensis*. The artificial cultivation preferably includes several techniques such as fermentation technology like submerged fermentation. The resulting fungi or mycelial strains are referred to herein as *Cordyceps* derivates, i.e. artificial *Cordyceps*. *Cordyceps* derivates in particular include the five artificial mycelial strains approved as drugs by the CFDA and commonly sold as health products as alternative to wild-type *Cordyceps*, herein referenced as *Cordyceps sinensis* such as available from Jiangxi Jiminkexin Pharmaceutical Co., Ltd., *Hirsutella sinensis* such as marketed by Hangzhou Zhongmei Huadong Pharmaceutical Co., Ltd., *Cephalosporium sinensis* such as available from Yunnan Baiyao Group Lijiang Pharmaceutical Co. Ltd., Shenyang Dongxin Pharmaceutical Co., Ltd., Hunan Kangerjia Pharmaceutical Co., Ltd., Guizhou Liangji Pharmaceutical Co., Ltd. and Jiangsu Shenhua Pharmaceutical Co., Ltd., *Mortierella* SP such as marketed by Hangzhou Tianyuan Pharmaceutical Co., Ltd. and Datong Liqun Pharmaceutical Co., Ltd. and *Gliocadium roseum* such as from Hebei Changtian Pharmaceutical Co., Ltd.

The term "sphingolipids" as used herein and as known to a skilled person refers to a family of compounds with a common structural feature, namely a sphingoid base backbone that is synthesized from serine and long-chain fatty acyl-CoA, then converted into one of the respective subgroups. Within this patent application sphingolipids include four subgroups, namely sphingoid bases, ceramides, phosphosphingolipids and glycosphingolipids.

Sphingolipids as used within this patent application are based on the structure of Formula (I), also referenced as sphingolipid basic structure:

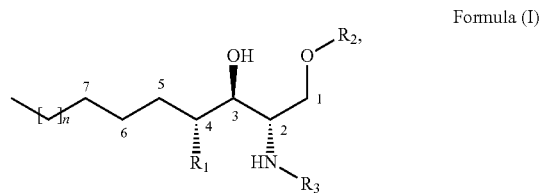

Formula (I)

The numbers 1 to 7 in said Formula indicate the position of the respective carbon atom in the carbon chain of the sphingolipid basic structure (i.e. without considering any carbon atoms in $R_2$ or $R_3$). $R_1$ is selected from —H or —OH. In case $R_1$ is —H, this is referenced as "dihydroxy base" and abbreviated with a "d" in the respective compound name. In case $R_1$ is —OH, this is referenced as "trihydroxy base" and abbreviated with a "t" in the respective compound name. $R_2$ and $R_3$ vary depending on the specific subgroup of sphingolipids and, thus, determine the specific subgroup of sphingolipids. n is an integer and usually higher than 1 such as 6, 10 or 11.

One or more than one double bond may optionally be present in the sphingolipid basic structure of Formula (I) (i.e. without considering possible double bonds in $R_2$ or $R_3$). Said additional double bond can, for example, be present at carbon position 4 (C4) in case $R_1$ is H. A second double bond optionally present when $R_1$ is —H could then be at carbon position 6 (C6) and a third optional double bond at carbon position 8 (C8) and so on. In case $R_1$ is —OH, said additional double bond can, for example, be present at carbon position 6 (C6). A second double bond optionally present when $R_1$ is —OH could then be at carbon position 8 (C8) and a third optional double bond at carbon position 10 (C10) and so on.

There are also sphingolipids in which the —OH group in the sphingolipid basic structure at carbon position 3 (C3) is missing, which embodiments are referenced herein with an "m".

The subgroup of "sphingoid bases" as used herein in particular includes sphingosines, sphinganines, sphingoid base-1-phosphate and lysosphingomyelin.

Sphingosines (also abbreviated as "So") and also named sphingenines are based on the general structure of Formula (I), wherein $R_2$ and $R_3$ are —H and wherein at least one double bond is present in the sphingolipid basic structure of Formula (I).

Sphinganines (also abbreviated as "Sa") have the general structure of Formula (I), wherein $R_2$ and $R_3$ are —H and wherein no double bond is present in the sphingolipid basic structure of Formula (I).

Sphingoid base-1-phosphates (also abbreviated as "S1P") have the general structure of Formula (I), wherein $R_3$ is —H and wherein $R_2$ is

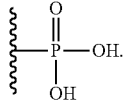

Lysosphingomyelines (also abbreviated as "S1Po") have the general structure of Formula (I), wherein $R_3$ is —H and $R_2$ is

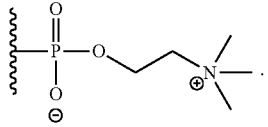 [SMILES: *P(=O)([O-])OCC[N+](C)(C)C]

The subgroup of ceramides (also abbreviated as "Cer") as used herein refers to sphingoid bases with an amide-linked fatty acid also named N-acyl-sphingoid bases and have the general structure of Formula (I), wherein $R_2$ is —H and wherein $R_3$ is a structure of Formula (II):

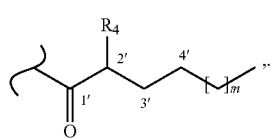

Formula (II)

wherein $R_4$ can be —H or —OH. In embodiments, in which $R_4$ is —OH, this is indicated in the respective name of the compound used herein with a supplementary expression "(OH)". m is an integer and usually above 1 such as 9, 11 or 13. One or more than one double bond may be present of which the possible location varies with the chain length of the fatty acid, i.e. the structure of Formula (II). In the structure of formula (II), for example, the double bond can be located at C9' for a C18 fatty acid chain, at C11' for a C20 fatty acid chain, at C13' for a C22 fatty acid chain and so on.

Phosphosphingolipids as a subgroup are complex sphingolipids with head groups that are attached via phosphodiester linkages and in particular include sphingomyelins, inositol phosphorylceramides and mannosylinositol phosphorylceramides.

Sphingomyelins (also abbreviated as "SM") are based on the Formula (I) with $R_3$ being based on Formula (II), wherein $R_2$ is

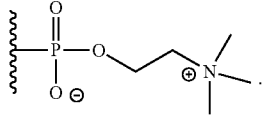 [SMILES: *P(=O)([O-])OCC[N+](C)(C)C]

Inositol phosphorylceramides (also abbreviated as "Pl-Cer") are based on the Formula (I) with $R_3$ being based on Formula (II), wherein $R_2$ is

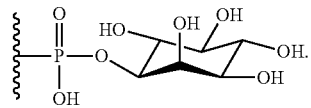

Mannosylinositol phosphorylceramides (also abbreviated as "MIPC") are based on the Formula (I) with $R_3$ being based on Formula (II), wherein $R_2$ is

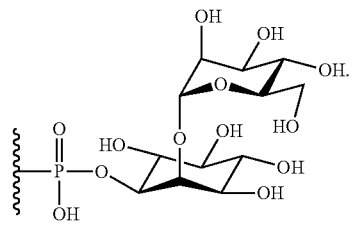

Glycosphingolipids as used herein are complex sphingolipids with head groups that are attached via glycosidic bonds, like hexosyl ceramides (also abbreviated as "Hex-Cer") which are based on the Formula (I) with $R_3$ being based on Formula (II), wherein $R_2$ is

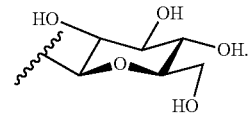

In sphingoid bases, the integer n in Formula (I) as well as presence of double bonds and number thereof and whether $R_1$ is —H or —OH is evident from the respective name of the compound used herein and in accordance with the usual nomenclature used for sphingolipids. As an example of sphingoid bases, "S1P (d18:1)" means that a total of 18 carbon atoms are present in the sphingoid basic structure of Formula (I) (i.e. without considering possible carbon atoms in $R_2$ or $R_3$) and that the number of double bonds in the sphingoid basic structure of Formula (I) (i.e. without considering possible double bonds in $R_2$ or $R_3$) is 1, i.e. n can be calculated based thereon. In case $R_1$ is —H, this is indicated with an initial "d" (dihydroxy base), wherein in case $R_1$ is —OH, this is evident from the initial letter "t". If one double bond is present, it can be, for example, at C4 in case of a dihydroxy base embodiment and can be, for example, at C6 in case of a trihydroxy base embodiment. A further double bond can be present at C6 for the dihydroxy base and C8 for the trihydroxy base and so on.

For ceramides, phosphosphingolipids and glycosphingolipids, the same applies with regard to Formula (I) indicated in the name of the respective compound as first part within the brackets. In addition to the features of Formula (I), the names of those sphingolipids used herein in accordance with the usual nomenclature further include features of the Formula (II) as second part within the brackets after the slash, i.e. $R_3$, namely m and $R_4$ are evident from the respective name indicated. As an example, Cer (d18:1/18:2) means that the structure of Formula (I) indicated as first part within the brackets, i.e. "d18:1", has 18 carbon atoms and one double bond (for example at C4) and is a dihydroxy base, i.e. $R_1$ is —H. As evident from the second part within the brackets, i.e. "18:2", $R_3$ has 18 carbon atoms and two double bonds (for example at C9' and C11') and $R_4$ is —H. In Cer (d18:1/18:2(OH)), $R_4$ is —OH.

The method of identifying and optionally quantifying at least one sphingolipid in a *Cordyceps* sample comprises steps of:

a) preparing a test sample solution from the *Cordyceps* sample comprising a step of (i) extracting the *Cordyceps* sample with at least a first extracting solvent, which first extracting solvent comprises an aliphatic alcohol;

b) subjecting the test sample solution to liquid chromatography with a mobile phase comprising at least a first and a second eluting solvent, wherein the at least first and second eluting solvent comprise a mixture of at least one aliphatic alcohol, at least one carboxylic acid and at least one carboxylic acid salt and wherein the second eluting solvent has a higher amount of aliphatic alcohol, namely total amount of the at least one aliphatic alcohol and of possible further aliphatic alcohols, in particular of the first and a second aliphatic alcohol, compared to the first eluting solvent; and c) performing a mass spectrometry following step b).

A *Cordyceps* sample comprises and preferably consists of *Cordyceps*, namely wild-type *Cordyceps* or *Cordyceps* derivates. Said *Cordyceps* sample can, for example, be a biological sample, a commercially available product or a pharmaceutical composition or the like. For the purpose of the present invention the *Cordyceps* sample preferably includes more than 80 wt.-%, further preferred more than 90 wt.-%, more preferably more than 95 wt.-% of wild-type *Cordyceps* or a *Cordyceps* derivate and in particular the *Cordyceps* sample consists of either wild-type *Cordyceps* or of a *Cordyceps* derivate.

According to the present invention, the at least one sphingolipid is selected from sphingoid bases, ceramides, phosphosphingolipids and glycosphingolipids. In preferred embodiments, said at least one sphingolipid is present in wild-type *Cordyceps*. Said sphingolipid may also be present in *Cordyceps* derivates. The method, in particular steps b) and c), can be carried out as described in Wang, J. R. et al., Anal. Chem. 2014, 86, 5688-5696 which is included herein by reference. The method of the present invention is preferably used for identifying and quantifying the at least one sphingolipid in the *Cordyceps* sample. Most preferably, at least two, further preferably at least three or most preferably at least 10 sphingolipids are identified or quantified in the *Cordyceps* sample. In especially preferred embodiments, the method is used for identifying and optionally quantifying, preferably identifying and quantifying the sphingolipid portion in the *Cordyceps* sample. The term "sphingolipid portion" used herein preferably means all or essentially all sphingolipids present in the *Cordyceps* sample, but most preferably it refers to the sphingolipids listed in table 1. I.e. the term sphingolipid portion in particular means all of the sphingolipids listed in table 1.

TABLE 1 sphingolipids preferably determined in a *Cordyceps* sample

| sphingolipid subgroup | further subgroup | sphingolipids preferably forming the sphingolipid portion |
|---|---|---|
| sphingoid bases | So | So (d17:1) |
| | | So (d14:2) |
| | | So (d14:1) |
| | | So (d16:1) |
| | | So (d17:2) |
| | | So (d18:2) |
| | | So (d18:1) |
| | | So (t18:1) |
| | | So (t18:1) isomer |
| | | So (d20:1) |
| | | So (t22:2) |
| | S1P | S1P (d17:1) |
| | | S1P (d18:1) |
| | S1Po | S1Po (d18:1) |
| | Sa | Sa (d17:0) |
| | | Sa (d16:0) |
| | | Sa (m18:0) |
| | | Sa (d17:0) isomer |
| | | Sa (d18:0) |
| | | Sa (t18:0) |
| | | Sa (t18:0) isomer |
| ceramides | Cer | Cer (d18:1/12:0) |
| | | Cer (d14:1/22:0) |
| | | Cer (d18:1/2:0) |
| | | Cer (d18:1/14:2) |
| | | Cer (d18:1/14:1) |
| | | Cer (d18:1/14:0) |
| | | Cer (d18:1/15:0) |
| | | Cer (d18:1/16:2) |
| | | Cer (d18:1/16:1) |
| | | Cer (d18:1/16:0) |
| | | Cer (d18:1/17:1) |
| | | Cer (d18:1/18:2) |
| | | Cer (d18:1/18:1) |
| | | Cer (d18:1/18:0) |
| | | Cer (d18:1/20:1) |
| | | Cer (d18:1/22:0) |
| | | Cer (d18:1/23:0) |
| | | Cer (d18:1/24:0) |
| | | Cer (d18:1/25:0) |
| | | Cer (d18:1/26:1) |
| | | Cer (d18:2/15:0) |
| | | Cer (d18:2/16:1) |
| | | Cer (d18:2/16:0) |
| | | Cer (d18:2/18:1) |
| | | Cer (d18:2/23:0) |
| | | Cer (d18:2/24:0) |
| | | Cer (d19:2/16:0) |
| | | Cer (d18:1/16:1(OH)) |
| | | Cer (d18:1/16:0(OH)) |
| | | Cer (d18:1/17:1(OH)) |
| | | Cer (d18:1/18:1(OH)) |
| | | Cer (d18:1/18:0(OH)) |
| | | Cer (d18:1/19:1(OH)) |
| | | Cer (d18:1/22:0(OH)) |
| | | Cer (d18:2/16:0(OH)) |
| | | Cer (d18:2/18:1(OH)) |
| | | Cer (d19:2/16:0(OH)) |
| | | Cer (d18:0/15:0) |
| | | Cer (d18:0/16:1) |
| | | Cer (d18:0/16:0) |
| | | Cer (d18:0/18:0) |
| | | Cer (d18:0/26:0) |
| | | Cer (t18:1/18:0) |
| | | Cer (t18:1/22:1) |
| | | Cer (t18:1/22:0) |
| | | Cer (t18:0/16:0) |
| | | Cer (t18:0/22:1) |
| | | Cer (t18:0/22:0) |
| | | Cer (t18:0/24:0) |
| | | Cer (t18:0/18:0(OH)) |
| | | Cer (t18:0/22:0(OH)) |
| | | Cer (t18:0/24:0(OH)) |

TABLE 1-continued sphingolipids preferably determined in a *Cordyceps* sample

| sphingolipid subgroup | further subgroup | sphingolipids preferably forming the sphingolipid portion |
|---|---|---|
| glycosphingolipids | HexCer | GlcCer (d18:1/12:0) |
| | | HexCer (d18:1/16:0) |
| | | HexCer (d18:2/16:0) |
| | | HexCer (d18:2/16:0(OH)) |
| | | HexCer (d19:2/15:0) |
| | | HexCer (d19:2/16:0(OH)) |
| | | HexCer (d19:2/17:0(OH)) |
| | | HexCer (d19:2/18:0(OH)) |
| | | HexCer (t19:1/16:1) |
| phosphosphingolipids | SM | SM (d18:1/12:0) |
| | | SM (d18:1/14:0) |
| | | SM (d18:1/16:0) |
| | | SM (d18:1/18:0) |
| | | SM (d18:1/20:0) |
| | | SM (d18:1/22:0) |
| | | SM (d18:1/24:0) |
| | | SM (d18:1/16:1) |
| | | SM (d18:1/20:1) |
| | | SM (d18:1/22:1) |
| | | SM (d18:2/18:0) |
| | | SM (d18:2/18:1) |
| | | SM (d18:1/18:1(OH)) |
| | | SM (d18:2/16:0(OH)) |
| | | SM (d33:1) |
| | | SM (d39:2) |
| | | SM (d42:2) |
| | | SM (d34:0) |
| | | SM (d36:0) |
| | | SM (d38:0) |
| | PI-Cer | PI-Cer (d18:0/16:0(OH)) |
| | | PI-Cer (t18:0/22:0(OH)) |
| | | PI-Cer (t18:0/24:0(OH)) |
| | MIPC | MIPC (t18:0/22:0(OH)) |
| | | MIPC (t18:0/24:0(OH)) |

In especially preferred embodiments, the method of the present invention is carried out for identifying and optionally quantifying, preferably identifying and quantifying, the sphingolipid portion in a *Cordyceps* sample, in particular all sphingolipids listed in table 1 in the *Cordyceps* sample.

Preferably, a powdered *Cordyceps* sample is used in step a) (i). Step a) may, thus, further comprise pulverizing the *Cordyceps* sample for obtaining a powdered *Cordyceps* sample before step (i). Preferably, between 1 and 100 mg, more preferably between 20 and 80 mg, still further preferably between 30 and 50 mg and in particular about 35 mg of the *Cordyceps* sample, in particular of the powdered *Cordyceps* sample, are used in step (i) for extraction.

The first extracting solvent in step a) (i) comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol of the first extracting solvent is a monohydric aliphatic alcohol having 1 to 4 carbon atoms, preferably an alkane with 1 to 4 carbon atoms with one hydrogen atom being replaced with a hydroxyl group. I.e. the aliphatic alcohol of the first extracting solvent is more preferably selected from methanol, ethanol, propanol, isopropanol, n-butanol, isobutanol, sec-butyl alcohol or tert-butyl alcohol. Most preferably, the aliphatic alcohol of the first extracting solvent is methanol.

The at least first extracting solvent preferably further comprises a halogenated hydrocarbon, i.e. as used herein a hydrocarbon, preferably an alkane, which hydrocarbon has at least one hydrogen atom substituted with a halogen atom. Preferably, the halogenated hydrocarbon in the first extracting solvent is a hydrocarbon, preferably a branched or straight chain alkane, which hydrocarbon has 1 to 4 carbon atoms and wherein at least one hydrogen atom is substituted with a halogen selected from Br, Cl, or F, in particular from Cl. Preferably, the halogenated hydrocarbon in the first extracting solvent is an alkane with 1 to 2 carbon atoms in which at least one hydrogen atom is substituted with a Cl atom, in particular selected from methyl chloride, dichloromethane or chloroform. Most preferably, the halogenated hydrocarbon in the first extracting solvent is chloroform. In further preferred embodiments of the present invention, the first extracting solvent comprises chloroform and methanol, preferably with a volume ratio of chloroform to methanol of less than 1, i.e. of less than 1:1, more preferably between 1:1.5 and 1:2.5, further preferably of about 1:2.

Preferably, at least three and most preferably three extracting solvents are used sequentially, i.e. subsequently, for extracting the *Cordyceps* sample in step a) (i). Preferably, the first, second and third extracting solvents comprise independently from each other an aliphatic alcohol, more preferably a monohydric aliphatic alcohol containing one to four carbon atoms, in particular based on a branched or straight chain alkane wherein one hydrogen atom is replaced with a hydroxyl group. Preferably, the first, second and third extracting solvents comprise independently from each other an aliphatic alcohol selected from methanol, ethanol, propanol, isopropanol, n-butanol, isobutanol, sec-butyl alcohol or tert-butyl alcohol. Further preferably, the first, second and third extracting solvents further comprise independently from each other a halogenated hydrocarbon, preferably a branched or straight chain alkane, which hydrocarbon has 1 to 4 carbon atoms and at least one hydrogen atom is substituted with a halogen selected from Br, Cl, or F, in particular from Cl, such as selected from methyl chloride, dichloromethane or chloroform. In most preferred embodiments, the first, second and third extracting solvents comprise methanol and chloroform each, wherein further preferred the volume ratio of chloroform to methanol in the first extracting solvent is less than 1, i.e. less than 1:1 and wherein the volume ratio of chloroform to methanol in the second eluting solvent is above 1, i.e. above 1:1, i.e. the volume of chloroform compared to the volume of methanol is higher in the second eluting solvent than in the first eluting solvent. More preferably, the first, second and third extracting solvents comprise methanol and chloroform each, wherein the volume ratio of chloroform to methanol in the first extracting solvent is less than 1:1 and wherein the volume ratio of chloroform to methanol in the second eluting solvent is above 1:1 and wherein the volume ratio of chloroform to methanol in the third eluting solvent is above 2:1.

The second extracting solvent preferably comprises chloroform and methanol in a volume ratio of 1.5:1 to 2.5:1, preferably about 2:1. The third extracting solvent preferably comprises chloroform and methanol in a volume ratio of chloroform to methanol of more than 2.5:1.

Further preferably, the first extracting solvent comprises chloroform and methanol, the second extracting solvent comprises chloroform and methanol, and the third extracting solvent comprises chloroform, methanol and water. More preferably, the first extracting solvent comprises and preferably essentially consists of chloroform and methanol in particular with a ratio of about 1:2 (v/v), the second extracting solvent comprises and preferably essentially consists of chloroform and methanol in particular with a ratio of about 2:1 (v/v) and the third extracting solvent comprises and preferably essentially consists of chloroform, methanol and water, in particular with a ratio of about 1.133:0.266:2 (v/v/v). The preferred three extracting solvents are in particular used sequentially, i.e. subsequently. As evident for a person skilled in the art, "comprising" means including a component but not excluding others, wherein "essentially consisting of" means consisting of the respective component along with usually and unavoidable impurities such as traces of further components or solvents or usual additives.

Preferably, step a) comprises steps of (i) extracting the *Cordyceps* sample with at least the first extracting solvent, which first extracting solvent comprises an aliphatic alcohol, in particular extracting the *Cordyceps* sample with the first, a second and a third extracting solvent for obtaining a *Cordyceps* extract;

(ii) reconstituting the *Cordyceps* extract with a reconstitution solvent for obtaining a reconstituted *Cordyceps* extract; and (iii) filtering the reconstituted *Cordyceps* extract for obtaining the test sample solution.

"Reconstitution" as used herein in particular means the addition of a reconstitution solvent to the dried *Cordyceps* extract. The reconstitution solvent is preferably added to the *Cordyceps* extract after removal of solvents present in the *Cordyceps* extract such as components of the first, second and third extracting solvent. Hence, step (i) preferably further includes removing solvents present in the *Cordyceps* extract in particular components of the first, second and third extracting solvent present after the extraction in step (i). The step of removing solvents is preferably carried out by means of one or more of drying with a stream of nitrogen, vacuum drying such as with a centrifugal vacuum concentrator in particular with SpeedVac™, freezing in liquid nitrogen and/or freeze drying. Most preferably, one or both of drying with a stream of nitrogen and/or vacuum drying in particular with a centrifugal vacuum concentrator like SpeedVac™ is used for removing the solvents before step (ii).

The reconstitution solvent, i.e. the solvent used for reconstitution in step (ii) preferably comprises and most preferably essentially consists of an aliphatic alcohol, in particular a monohydric aliphatic alcohol having 1 to 4 carbon atoms, preferably a branched or straight chain alkane with 1 to 4 carbons atoms wherein one hydrogen atom is substituted with a hydroxyl group. I.e. the aliphatic alcohol of the reconstitution solvent is more preferably selected from methanol, ethanol, propanol, isopropanol, n-butanol, isobutanol, sec-butyl alcohol or tert-butyl alcohol. Most preferably, the reconstitution solvent comprises and most preferably essentially consists of methanol.

The filtration in step (iii) is preferably carried out with a filter having a pore size of at most 0.30 μm, further preferably at most 0.25 μm and in particular about 0.22 μm.

In further preferred embodiments, step (i) comprises steps of:

1. contacting the *Cordyceps* sample with the first extracting solvent in particular comprising chloroform and methanol preferably in a ratio of less than 1:1 (v/v), preferably of about 1:2 (v/v), and subjecting the mixture of the *Cordyceps* sample and the first extracting solvent to sonication, preferably ultrasonication, preferably for at least 10 s and further preferred for about 30 s and preferably incubating the sonicated, more preferably ultrasonicated, mixture for preferably at least 4 h, preferably about 12 h at more than 30° C., preferably at about 48° C.;

2. adding a base after step 1 and incubating for at least 1 h, preferably about 2 h at least at 30° C., preferably about 37° C.;

3. neutralizing the mixture obtained after step 2 with a carboxylic acid;

4. subjecting the neutralized mixture after step 3) to centrifugation for obtaining a first supernatant and a first residue;

5. contacting said first residue with the second extracting solvent comprising chloroform and methanol in particular in a ratio of above 1:1, preferably of 2:1 (v/v) for obtaining a second residue and a second supernatant;

6. contacting the second residue with a third extracting solvent comprising chloroform, methanol and water in particular in with a ratio of chloroform to methanol of more than 2:1 (v/v), more preferably with a ratio of chloroform to methanol to water of 1.133:0.266:2 (v/v), wherein a lower and an upper layer is formed;

7. combining the first supernatant, the second supernatant and the lower layer and preferably removing solvents in particular by drying with a stream of nitrogen and/or vacuum drying in particular with a centrifugal vacuum concentrator like SpeedVac™ to form the *Cordyceps* extract.

The base in step 2 is preferably an alkali hydroxide. Alkali hydroxides are a class of chemical compounds which are composed of an alkali metal cation, i.e. cation of lithium (Li), sodium (Na), potassium (K), rubidium (Rb), caesium (Cs), and the hydroxide anion (HO). In particular, the alkali metal cation is K or Na. More preferably, the base is KOH in an aliphatic alcohol, preferably in methanol.

The term "neutralizing" as used herein means adding a carboxylic acid for obtaining a pH between 6 and 8. A carboxylic acid as used herein is a compound containing at least one carboxyl group, i.e. —COOH, in particular based on a hydrocarbon such as a branched or straight chain alkane in which at least one carbon atom forms a carboxyl group. In particular, the carboxylic acid is based on a straight chain alkane with 1 to 4 carbon atoms more preferably 1 to 2 carbon atoms, wherein at least one carbon atom forms a carboxyl group, preferably one carbon atoms forms a carboxyl group. More preferably, the carboxylic acid in step 3 is acetic acid.

The liquid chromatography as used herein refers to a chromatography with a substance to be determined in the liquid, i.e. mobile phase, and an additional solid phase, usually a column. The skilled person is aware of this term and how to carry out a liquid chromatography. The liquid chromatography is preferably a high pressure liquid chromatography (HPLC), more preferably an ultrahigh pressure liquid chromatography (UHPLC, also known as UPLC, RRLC, RSLC or UFLC). The terms high pressure liquid chromatography and ultrahigh pressure liquid chromatography are used for specific subtypes of liquid chromatography. The skilled person is aware of said terms and how to carry out such subtypes of chromatography.

Preferably, a $C_{18}$ column is used as stationary phase, i.e. a column comprising straight chain $C_{18}$ alkyl groups, i.e. the substances in the stationary phase contain 18 carbon atoms. Preferably, a $C_{18}$ column with dimensions of about 100 mm×2.1 mm and a particle size of about 1.8 μm is used, more preferably an Agilent Eclipse Plus $C_{18}$ column. Preferably, the UHPLC system is equipped with a binary solvent delivery system and a standard autosampler, more preferably the Agilent 1290 Infinity UHPLC system is used in step b).

The mobile phase comprises and preferably consists of the at least first and second eluting solvent. The first and the second eluting solvent independently from each other comprise at least one aliphatic alcohol, in particular a monohydric aliphatic alcohol having 1 to 4 carbon atoms, preferably a straight chain or branched alkane in which one hydrogen atom is substituted with a hydroxyl group. The aliphatic alcohol of the first and second eluting solvent is more preferably independently selected from methanol, ethanol, propanol, isopropanol, n-butanol, isobutanol, sec-butyl alcohol or tert-butyl alcohol. Most preferably, the aliphatic alcohol of the first and second eluting solvent is independently selected from methanol or isopropanol. Most preferably, the first eluting solvent comprises methanol as aliphatic alcohol, preferably does not comprise a further aliphatic alcohol. Most preferably, the second eluting solvent comprises methanol as first aliphatic alcohol and isopropanol as second aliphatic alcohol.

The first and second eluting solvent independently from each other further comprise at least one carboxylic acid, in particular a hydrocarbon such as a branched or straight chain alkane, wherein at least one carbon atom forms a carboxyl group. Preferably, the carboxylic acid is based on a straight chain alkane with 1 to 4 carbon atoms more preferably 1 to 2 carbon atoms, wherein at least one carbon atom forms a carboxyl group, preferably one carbon atom forms a carboxyl group. More preferably, the carboxylic acid in the first and second eluting solvent is formic acid.

The first and second eluting solvent preferably further comprise a carboxylic acid salt, namely a metal salt of a carboxylic acid, in particular an ammonium salt of a carboxylic acid of a branched or straight chain carboxylic acid with 1 to 4, more preferably 1 to 2 carbon atoms. Most preferably, the carboxylic acid salt is ammonium acetate.

More preferably, the first eluting solvent comprises methanol, $H_2O$, formic acid and ammonium acetate. The second eluting solvent most preferably comprises methanol, isopropanol, formic acid and ammonium acetate.

In particular embodiments, the first eluting solvent comprises and in particular essentially consists of methanol, $H_2O$ and formic acid (60:40:0.2, v/v/v) and 10 mM ammonium acetate and the second eluting solvent comprises and in particular essentially consists of methanol, isopropanol, and formic acid (60:40:0.2, v/v/v) and 10 mM ammonium acetate.

Preferably, a linear gradient is applied preferably with increasing amounts of the second eluting solvent. In most preferred embodiments, the linear gradient given in table 2 is applied:

TABLE 2 preferred linear gradient applied

| time (min) | amount of second eluting solvent in mobile phase |
|---|---|
| 0-3 | 0-10% |
| 3-5 | 10-40% |
| 5-5.3 | 40-55% |
| 5.3-8 | 55-60% |
| 8-8.5 | 60-80% |
| 8.5-10.5 | 80% |
| 10.5-16 | 80-90% |
| 16-19 | 90% |
| 19-22 | 90-100% |
| subsequently | 100% and equilibration with 0% |

The injection volume is in particular between 1 μL and 3 μL, preferably about 2 μL. The temperature is preferably 35° C. to 45° C., more preferably about 40° C. The run time is preferably at least 15 min, in particular about 20 min. The flow rate is preferably about 0.4 mL/min.

The mass spectrometry in step c) preferably comprises one or both of a Q-TOF mass spectrometry, i.e. quadrupole time-of-flight mass spectrometry, and/or QQQ mass spectrometry, i.e. triple-quadrupole mass spectrometry. In particular an MS/MS mode is used, also named tandem mass spectrometry mode, which is known to the skilled person.

Q-TOF mass spectrometry is preferably used for identifying the at least one sphingolipid in the *Cordyceps* sample. In especially preferred embodiments, mass spectrometry comprises the application of the jet stream technology known to the skilled person, in particular it comprises the application of an Agilent ultrahigh definition 6550 Q-TOF mass spectrometer. Preferably, a soft ionization method, in particular electrospray ionization (ESI) is used.

In preferred embodiments, the following conditions are applied for the Q-TOF mass spectrometry:
  as parameters for the jet stream a superheated ($N_2$) sheath gas temperature of 350° C. to 450°, preferably of about 400° C.; and/or preferably a flow rate of 8 L/min to 13 L/min, preferably of about 12 L/min; and/or
  as preferred electrospray ionization conditions in particular a positive ion mode, a capillary voltage of 3000 V to 5000 V, preferably of about 4000 V, a nozzle voltage of 100 to 500 V, preferably of about 300 V, a nebulizer pressure of 20 psi to 50 psi, preferably of about 40 psi (0.27579 MPa), a drying gas flow of about 5 L/min to 15 L/min, preferably of about 6 L/min, a drying gas temperature of 150° C. to 450° C., preferably of about 300° C.; and preferably a skimmer voltage of about 50 V to 80 V, preferably of about 65 V, an octapole RF peak voltage of 300 V to 600 V, preferably of about 500 V and a fragmentor voltage of about 100 V to 380 V, in particular of about 150 V.

A targeted MS/MS collision energy (CE) can be set at three different values between 20-60 eV. The mass spectra are preferably recoded at the range m/z 110-1200. Preferably, a reference solution is nebulized for continuous calibration in positive ion mode using the reference masses m/z 121.0509 and 922.0098. Preferably, full-scan and MS/MS data are processed with suitable software such as Agilent Mass Hunter Workstation Software and the results are compared with respective sphingolipid databases and/or with the data in table 7 or alternatively by comparing the results with respective standards.

QQQ mass spectrometry is preferably applied for quantifying the at least one sphingolipid in the *Cordyceps* sample, preferably based on a soft ionization method, in particular electrospray ionization (ESI). In especially preferred embodiments, an Agilent 6460 QQQ mass spectrometer is used. In preferred embodiments, the following conditions are applied for the QQQ mass spectrometry:
  as parameters for the jet stream a superheated ($N_2$) sheath gas temperature of 350° C. to 450°, preferably of about 400° C., and/or a flow rate of 8 L/min to 13 L/min, preferably of about 12 L/min;
as electrospray ionization conditions in particular a positive ion mode, a capillary voltage of 2500 V to 5000 V, preferably of about 3500 V, a nozzle voltage of 100 to 500 V, preferably of about 300 V, a nebulizer pressure of 20 psi to 50 psi, preferably of about 40 psi (0.27579 MPa), a drying gas flow of 5 L/min to 15 L/min, preferably of about 6 L/min, a drying gas temperature of 150° C. to 450° C., preferably of about 300° C.

Preferably, a MRM mode, i.e. multiple reacting monitoring mode, is used. To ensure the maximum sensitivity, a two segment scan can be adopted.

Preferred MRM transitions, fragmentor voltages and collision energy (CE) values selected for quantification of individual sphingolipids which are in particular determined are given in table 3.

TABLE 3

Preferred parameters for quantification of sphingolipids in *Cordyceps*

| sphingolipid | subgroup | No. | Name | Retention time (min) | MRM transitions (m/z) | Fragmentor (V) | CE (eV) |
|---|---|---|---|---|---|---|---|
| sphingoid bases | So | IS-1 | So (d17:1) | 6.37 | 286.3→268.3 | 80 | 5 |
| | | 1 | So (d14:2) | 3.76 | 242.2→224.2 | 80 | 5 |
| | | 2 | So (d14:1) | 5.30 | 244.2→226.1 | 80 | 5 |
| | | 3 | So (d16:1) | 5.95 | 272.3→254.2 | 80 | 5 |
| | | 4 | So (d17:2) | 7.11 | 284.3→266.2 | 80 | 5 |
| | | 5 | So (d18:2) | 6.50 | 298.3→280.3 | 80 | 5 |
| | | 6 | So (d18:1) | 6.78 | 300.3→282.3 | 80 | 5 |
| | | 7 | So (t18:1) | 6.38 | 316.3→298.3 | 80 | 5 |
| | | 8 | So (t18:1) isomer | 6.90 | 316.3→298.3 | 80 | 5 |
| | | 9 | So (d20:1) | 9.41 | 328.3→310.3 | 80 | 5 |
| | | 10 | So (t22:2) | 9.13 | 370.3→352.3 | 80 | 5 |
| | S1P | IS-2 | S1P (d17:1) | 6.55 | 366.2→250.3 | 105 | 10 |
| | | 11 | S1P (d18:1) | 9.03 | 380.3→362.3 | 105 | 10 |
| | S1Po | 12 | S1Po (d18:1) | 6.55 | 467.4→449.3 | 105 | 10 |
| | Sa | IS-3 | Sa (d17:0) | 6.57 | 288.3→270.3 | 110 | 20 |
| | | 13 | Sa (d16:0) | 6.24 | 274.3→256.3 | 110 | 20 |
| | | 14 | Sa (m18:0) | 7.12 | 286.3→268.3 | 110 | 20 |
| | | 15 | Sa (d17:0) isomer | 5.51 | 288.3→270.3 | 110 | 20 |
| | | 16 | Sa (d18:0) | 6.91 | 302.3→284.3 | 110 | 20 |
| | | 17 | Sa (t18:0) | 6.61 | 318.3→300.3 | 110 | 20 |
| | | 18 | Sa (t18:0) isomer | 6.32 | 318.3→300.3 | 110 | 20 |
| cceramides | Cer | IS-4 | Cer (d18:1/12:0) | 10.96 | 482.5→264.3 | 130 | 25 |
| | | 19 | Cer (d14:1/22:0) | 14.64 | 566.5→208.2 | 130 | 25 |
| | | 20 | Cer (d18:1/2:0) | 9.04 | 342.3→264.3 | 130 | 25 |
| | | 21 | Cer (d18:1/14:2) | 11.06 | 506.5→264.3 | 130 | 25 |
| | | 22 | Cer (d18:1/14:1) | 11.15 | 508.5→264.3 | 130 | 25 |
| | | 23 | Cer (d18:1/14:0) | 11.85 | 510.5→264.3 | 130 | 25 |
| | | 24 | Cer (d18:1/15:0) | 12.33 | 524.5→264.3 | 130 | 25 |
| | | 25 | Cer (d18:1/16:2) | 11.84 | 534.5→264.3 | 130 | 25 |
| | | 26 | Cer (d18:1/16:1) | 12.43 | 536.5→264.3 | 130 | 25 |
| | | 27 | Cer (d18:1/16:0) | 12.92 | 538.5→264.3 | 130 | 25 |
| | | 28 | Cer (d18:1/17:1) | 13.03 | 550.5→264.3 | 130 | 25 |
| | | 29 | Cer (d18:1/18:2) | 13.45 | 562.5→264.3 | 130 | 25 |
| | | 30 | Cer (d18:1/18:1) | 13.57 | 564.5→264.3 | 130 | 25 |
| | | 31 | Cer (d18:1/18:0) | 14.36 | 566.5→264.3 | 130 | 25 |
| | | 32 | Cer (d18:1/20:1) | 15.86 | 592.6→264.3 | 130 | 25 |
| | | 33 | Cer (d18:1/22:0) | 18.20 | 622.6→264.3 | 130 | 25 |
| | | 34 | Cer (d18:1/23:0) | 19.10 | 636.6→264.3 | 130 | 25 |
| | | 35 | Cer (d18:1/24:0) | 20.10 | 650.6→264.3 | 130 | 25 |
| | | 36 | Cer (d18:1/25:0) | 19.25 | 664.7→264.3 | 130 | 25 |
| | | 37 | Cer (d18:1/26:1) | 19.23 | 676.7→264.3 | 130 | 25 |
| | | 38 | Cer (d18:2/15:0) | 11.83 | 522.5→262.3 | 130 | 25 |
| | | 39 | Cer (d18:2/16:1) | 11.85 | 534.5→262.3 | 130 | 25 |
| | | 40 | Cer (d18:2/16:0) | 12.38 | 536.5→262.3 | 130 | 25 |
| | | 41 | Cer (d18:2/18:1) | 13.50 | 562.5→262.3 | 130 | 25 |
| | | 42 | Cer (d18:2/23:0) | 18.18 | 634.6→262.3 | 130 | 25 |
| | | 43 | Cer (d18:2/24:0) | 19.06 | 648.6→262.3 | 130 | 25 |
| | | 44 | Cer (d19:2/16:0) | 12.76 | 550.5→276.3 | 130 | 25 |
| | | 45 | Cer (d18:1/16:1(OH)) | 12.32 | 552.5→264.3 | 130 | 25 |
| | | 46 | Cer (d18:1/16:0(OH)) | 12.40 | 554.5→264.3 | 130 | 25 |
| | | 47 | Cer (d18:1/17:1(OH)) | 15.36 | 566.5→264.3 | 130 | 25 |
| | | 48 | Cer (d18:1/18:1(OH)) | 14.53 | 580.5→264.3 | 130 | 25 |
| | | 49 | Cer (d18:1/18:0(OH)) | 13.55 | 582.5→264.3 | 130 | 25 |
| | | 50 | Cer (d18:1/19:1(OH)) | 12.55 | 594.5→264.3 | 130 | 25 |
| | | 51 | Cer (d18:1/22:0(OH)) | 17.11 | 638.6→264.3 | 130 | 25 |
| | | 52 | Cer (d18:2/16:0(OH)) | 11.84 | 552.5→262.3 | 130 | 25 |
| | | 53 | Cer (d18:2/18:1(OH)) | 11.52 | 578.5→262.3 | 130 | 25 |
| | | 54 | Cer (d19:2/16:0(OH)) | 12.20 | 566.5→276.3 | 130 | 25 |
| | | 55 | Cer (d18:0/15:0) | 12.75 | 526.5→266.3 | 130 | 25 |
| | | 56 | Cer (d18:0/16:1) | 13.23 | 538.5→266.3 | 130 | 25 |
| | | 57 | Cer (d18:0/16:0) | 13.35 | 540.5→266.3 | 130 | 25 |
| | | 58 | Cer (d18:0/18:0) | 14.63 | 568.6→266.3 | 130 | 25 |
| | | 59 | Cer (d18:0/26:0) | 20.82 | 680.7→266.3 | 130 | 25 |
| | | 60 | Cer (t18:1/18:0) | 12.99 | 582.5→262.3 | 130 | 25 |

TABLE 3-continued

Preferred parameters for quantification of sphingolipids in *Cordyceps*

| sphingolipid | subgroup | No. | Name | Retention time (min) | MRM transitions (m/z) | Fragmentor (V) | CE (eV) |
|---|---|---|---|---|---|---|---|
| | | 61 | Cer (t18:1/22:1) | 16.15 | 636.6→262.3 | 130 | 25 |
| | | 62 | Cer (t18:1/22:0) | 15.64 | 638.6→262.3 | 130 | 25 |
| | | 63 | Cer (t18:0/16:0) | 12.28 | 556.5→264.3 | 130 | 25 |
| | | 64 | Cer (t18:0/22:1) | 16.12 | 638.6→264.3 | 130 | 25 |
| | | 65 | Cer (t18:0/22:0) | 16.13 | 640.6→264.3 | 130 | 25 |
| | | 66 | Cer (t18:0/24:0) | 17.45 | 668.7→264.3 | 130 | 25 |
| | | 67 | Cer (t18:0/18:0(OH)) | 12.98 | 600.6→264.3 | 130 | 25 |
| | | 68 | Cer (t18:0/22:0(OH)) | 15.48 | 656.6→264.3 | 130 | 25 |
| | | 69 | Cer (t18:0/24:0(OH)) | 16.83 | 684.7→264.3 | 130 | 25 |
| glycosphingolipids | HexCer | IS-5 | GlcCer (d18:1/12:0) | 10.40 | 644.5→264.3 | 130 | 30 |
| | | 70 | HexCer (d18:1/16:0) | 12.21 | 700.6→264.3 | 130 | 30 |
| | | 71 | HexCer (d18:2/16:0) | 11.52 | 698.6→262.3 | 130 | 30 |
| | | 72 | HexCer (d18:2/16:0(OH)) | 11.25 | 714.6→262.3 | 130 | 30 |
| | | 73 | HexCer (d19:2/15:0) | 11.46 | 698.6→276.3 | 130 | 30 |
| | | 74 | HexCer (d19:2/16:0(OH)) | 11.75 | 728.6→276.3 | 130 | 30 |
| | | 75 | HexCer (d19:2/17:0(OH)) | 12.00 | 742.6→276.3 | 130 | 30 |
| | | 76 | HexCer (d19:2/18:0(OH)) | 12.53 | 756.6→276.3 | 130 | 30 |
| | | 77 | HexCer (t19:1/16:1) | 11.20 | 728.6→276.3 | 130 | 30 |
| phosphosphingolipids | SM | IS-6 | SM (d18:1/12:0) | 10.37 | 647.5→184.1 | 170 | 20 |
| | | 78 | SM (d18:1/14:0) | 11.1 | 675.5→184.1 | 170 | 20 |
| | | 79 | SM (d18:1/16:0) | 12 | 703.6→184.1 | 170 | 20 |
| | | 80 | SM (d18:1/18:0) | 13.25 | 731.6→184.1 | 170 | 20 |
| | | 81 | SM (d18:1/20:0) | 14.51 | 759.6→184.1 | 170 | 20 |
| | | 82 | SM (d18:1/22:0) | 15.61 | 787.7→184.1 | 170 | 20 |
| | | 83 | SM (d18:1/24:0) | 16.91 | 815.7→184.1 | 170 | 20 |
| | | 84 | SM (d18:1/16:1) | 11.66 | 701.6→184.1 | 170 | 20 |
| | | 85 | SM (d18:1/20:1) | 13.9 | 757.6→184.1 | 170 | 20 |
| | | 86 | SM (d18:1/22:1) | 15.12 | 785.7→184.1 | 170 | 20 |
| | | 87 | SM (d18:2/18:0) | 12.75 | 729.6→184.1 | 170 | 20 |
| | | 88 | SM (d18:2/18:1) | 11.81 | 727.6→184.1 | 170 | 20 |
| | | 89 | SM (d18:1/18:1(OH)) | 12.38 | 745.6→184.1 | 170 | 20 |
| | | 90 | SM (d18:2/16:0(OH)) | 11.07 | 717.6→184.1 | 170 | 20 |
| | | 91 | SM (d33:1) | 11.56 | 689.6→184.1 | 170 | 20 |
| | | 92 | SM (d39:2) | 14.56 | 771.6→184.1 | 170 | 20 |
| | | 93 | SM (d42:2) | 16.14 | 813.7→184.1 | 170 | 20 |
| | | 94 | SM (d34:0) | 12.5 | 705.6→184.1 | 170 | 20 |
| | | 95 | SM (d36:0) | 13.84 | 733.6→184.1 | 170 | 20 |
| | | 96 | SM (d38:0) | 14.9 | 761.7→184.1 | 170 | 20 |
| | PI-Cer | 97 | PI-Cer (d18:0/16:0(OH)) | 10.90 | 798.5→538.5 | 170 | 30 |
| | | 98 | PI-Cer (t18:0/22:0(OH)) | 12.84 | 898.6→638.6 | 170 | 30 |
| | | 99 | PI-Cer (t18:0/24:0(OH)) | 13.95 | 926.7→666.6 | 170 | 30 |
| | MIPC | 100 | MIPC (t18:0/22:0(OH)) | 12.60 | 1060.7→638.6 | 170 | 40 |
| | | 101 | MIPC (t18:0/24:0(OH)) | 13.68 | 1088.7→666.6 | 170 | 40 |

Preferably, the obtained full-scan and MS or MS/MS data are processed with suitable software such as with an Agilent Mass Hunter Workstation Software.

In most preferred embodiments, in step b) and step c) a liquid chromatography coupled to a mass spectrometer is used, i.e. LC/MS such as commercially available, in particular LC-ESI-MS or LC-ESI-MS/MS. Thus, LC for separating the components in the *Cordyceps* sample is applied, wherein the separated components are then automatically introduced in a mass spectrometer. Preferably, UHPLC, coupled to a mass spectrometer such as UHPLC-Q-TOF-MS and/or UHPLC-QQQ-MS is used in step b) and c). Preferably, single MS mode or a MS/MS mode can used in step c), preferably MS/MS mode and most preferably based on ESI.

In embodiments of the present invention, UHPLC-Q-TOF-MS is used for identifying the at least one sphingolipid, preferably the sphingolipid portion, in particular all sphingolipids listed in table 1, in the *Cordyceps* sample, and subsequently QQQ-MS is used for quantifying the at least one sphingolipid, preferably the sphingolipid portion, in particular all sphingolipids listed in table 1, in the *Cordyceps* sample.

In a further aspect, a method of identifying wild-type *Cordyceps* in a *Cordyceps* sample is provided comprising steps of:
a) identifying and quantifying the sphingolipid portion, in particular all sphingolipids listed in table 1, in a *Cordyceps* sample as described above including above described preferred embodiments of the method steps;
b) determining at least a first and a second *Cordyceps* wild-type indicative parameter,
c) comparing the at least first and second *Cordyceps* wild-type indicative parameter with a respective reference value.

Said at least first and second *Cordyceps* wild-type indicative parameter corresponding to the respective reference value indicates that the sample of *Cordyceps* is wild-type *Cordyceps*, i.e. in case both, namely the first and second *Cordyceps* wild-type indicative parameter, correspond to the respective reference values, the sample comprises and/or is of wild-type *Cordyceps*.

The term "*Cordyceps* wild-type indicative parameter" as used herein is a parameter which has a characteristic value in wild-type *Cordyceps* suitable to distinguish wild-type *Cordyceps* from *Cordyceps* derivates and further preferably also suitable to distinguish wild-type *Cordyceps* from parts thereof, namely the isolated fruiting body or the *sclerotium* of wild-type *Cordyceps* alone. "*Cordyceps* derivate indicative parameter" is likewise a parameter indicative of a specific *Cordyceps* derivate, i.e. suitable to identify a specific *Cordyceps* derivate from other *Cordyceps* derivates and wild-type *Cordyceps*.

Said first *Cordyceps* wild-type indicative parameter is the ratio of ceramides to sphingoid bases, wherein the reference value is an amount of total ceramides of at least 10 wt.-% and less than 100 wt.-% relative to the total amount of sphingoid bases. I.e. wild-type *Cordyceps* has a lower amount of ceramides compared to the amount of sphingoid bases, in particular sphingoid bases are the dominant sphingolipid in wild-type *Cordyceps*. Preferably, the reference value for the first *Cordyceps* wild-type indicative parameter means an amount of ceramides of at least 15 wt.-% and at most 85 wt.-%, more preferably at least 25 wt.-% and at most 85 wt.-% relative to the amount of sphingoid bases.

Said second *Cordyceps* wild-type indicative parameter is the ratio of glycosphingolipids to phosphosphingolipids and wherein the reference value is an amount of glycosphingolipids which is at most 80 wt.-% relative to the amount of phosphosphingolipids. I.e. wild-type *Cordyceps* has a lower amount of glycosphingolipids compared to the amount of phosphosphingolipids. Preferably, the reference value for the second *Cordyceps* wild-type indicative parameter is an amount of glycosphingolipids which is at least 2 wt.-% and at most 80 wt.-%, further preferably at least 2 wt.-% and at most 70 wt.-%, further preferably at least 5 wt.-% and at most 50 wt.-% relative to the amount of phosphosphingolipids.

Preferably, at least one further *Cordyceps* wild-type indicative parameters is used in addition to the first and second *Cordyceps* wild-type indicative parameter, more preferably a combination of two or more of the following *Cordyceps* wild-type indicative parameters in addition to the first and second *Cordyceps* wild-type indicative parameters:

the ratio of phosphosphingolipids to ceramides, wherein the reference value in step c) for said further *Cordyceps* wild-type indicative parameter is an amount of phosphosphingolipids which is at least 50 wt.-% and at most 110 wt.-% relative to the amount of ceramides;

the ratio of sphinganines to sphingosines, wherein the reference value in step c) for said further *Cordyceps* wild-type indicative parameter is that the amount of sphinganines is at most 80 wt.-%, preferably between 20 wt.-% and 80 wt.-%, more preferably between 20 wt.-% and 70 wt.-%, in particular between 20 wt.-% and 60 wt.-% relative to the amount of sphingosines; preferably said parameter of the ratio of sphinganines to sphingosines is combined with a further *Cordyceps* wild-type indicative parameter, namely that certain sphingosines are present as reference value selected from So (d14:1), So (d14:2), So (d18:2), So (d20:1), So (t18:1), So (t18:1) isomer and So (t22:2);

the ratio of certain ceramides, namely of t18Cer to d18Cer, wherein the reference value in step c) for said further *Cordyceps* wild-type indicative parameter is that the amount of t18Cer is at least 50 wt.-% relative to the amount of d18Cer;

the ratio of inositol phosphorylceramides (Pl-Cer) to sphingomyelins (SM), wherein the reference value in step c) for said further *Cordyceps* wild-type indicative parameter is that the amount of Pl-Cer is at most 20 wt.-% relative to the amount of SM;

the amount of hexosyl ceramides (HexCer), wherein the reference value in step c) for said further *Cordyceps* wild-type indicative parameter is that the amount of HexCer in the *Cordyceps* sample is between 2 pmol/mg and 6 pmol/mg, in particular 3 pmol/mg to 5 pmol/mg;

the amount of sphingosines (So), wherein the reference value in step c) for said further *Cordyceps* wild-type indicative parameter is that the amount of So in the *Cordyceps* sample is at least 25 pmol/mg, preferably at least 30 pmol/mg;

the amount of d18 Cer, wherein the reference value in step c) for said further *Cordyceps* wild-type indicative parameter is that the amount of d18Cer in the *Cordyceps* sample is at most 30 pmol/mg, preferably at most 25 pmol/mg;

the sum of the amounts of Pl-Cer and MIPC, wherein the reference value in step c) for said further *Cordyceps* wild-type indicative parameter is that sum of the amounts of Pl-Cer and MIPC in the *Cordyceps* sample is at most 5 pmol/mg, preferably at most 2 pmol/mg.

The sphingolipids are preferably the ones given in table 1. I.e. the above reference values are based on all of the sphingolipids mentioned there. With other words, for example the amount of sphingoid bases preferably refers to the total amount of the sphingoid bases listed in table 1. The amount of ceramides refers to the sum of amounts, i.e. the total amount, of the ceramides listed in table 1. Similar is true for glycosphingolipids, phosphosphingolipids, So, Sa, SM, Pl-Cer, d18Cer, t18Cer, MIPC and HexCer. As a further example, d18Cer preferably refers to the ceramides given in table 1 which have 18 carbon atoms in the carbon chain in Formula (I) (without considering the carbons atoms in $R_3$) and are of a dihydroxy type (dihydroxy base), i.e. all Cer starting with Cer (d18:[ . . . ]) in table 1. Accordingly, the amount of d18 Cer is preferably the total amount of the respective d18 Cer listed in table 1. Similar is true for t18 Cer and its amount.

A preferred further *Cordyceps* wild-type indicative parameter includes the amount of one or more of the following sphingolipids, which sphingolipids are especially suitable as markers, and further indicate presence of wild-type *Cordyceps* if the respective reference value in table 4 is met:

TABLE 4 preferred further *Cordyceps* wild-type indicative parameters

| preferred further *Cordyceps* wild-type indicative parameter: amount of | Preferred reference value (amount of respective sphingolipid in pmol/mg of the *Cordyceps* sample) | Further preferred reference value (amount of respective sphingolipid in pmol/mg of the *Cordyceps* sample) |
|---|---|---|
| HexCer (t19:1/16:1) | 0.4 to 1 | about 0.715 ± 0.120 |
| HexCer (d19:2/16:0(OH)) | 0.5 to 1.5 | about 0.958 ± 0.289 |
| So (d18:1) | 0.1 to 1 | about 0.493 ± 0.268 |

TABLE 4-continued preferred further *Cordyceps* wild-type indicative parameters

| preferred further *Cordyceps* wild-type indicative parameter: amount of | Preferred reference value (amount of respective sphingolipid in pmol/mg of the *Cordyceps* sample) | Further preferred reference value (amount of respective sphingolipid in pmol/mg of the *Cordyceps* sample) |
|---|---|---|
| Sa (d16:0) | up to 0.1 | about 0.013 ± 0.013 |
| PI-Cer (d18:0/16:0(OH)) | up to 0.1 | about 0 |
| SM (d18:2/16:0(OH)) | 0.2 to 0.8 | about 0.419 ± 0.058 |
| Cer (d18:1/18:1) | up to 0.5 | about 0.074 ± 0.069 |
| Cer (d18:0/18:0) | up to 0.2 | about 0.008 ± 0.006 |
| Cer (d18:0/16:1) | up to 0.2 | about 0.031 ± 0.025 |
| SM (d18:2/18:0) | 6 to 15 | about 10.426 ± 2.543 |
| Sa (m18:0) | up to 0.15 | about 0.046 ± 0.011 |

Most preferably, a further *Cordyceps* wild-type indicative parameter includes the amount of each of HexCer (t19:1/16:1), Sa (d16:0), SM (d18:2/16:0(OH)), Cer (d18:0/16:1) and Cer (d18:1/18:1), wherein the reference value in step c) for said further *Cordyceps* wild-type indicative parameter is that the amount of HexCer (t19:1/16:1) is at most 3 pmol/mg, Sa (d16:0) at most 1 pmol/mg, SM (d18:2/16:0(OH)) at least 0.2 pmol/mg, Cer (d18:0/16:1) at most 0.4 pmol/mg and Cer (d18:1/18:1) at most 1 pmol/mg, preferably the amount of HexCer (t19:1/16:1) is at most 2 pmol/mg, of Sa (d16:0) at most 0.4 pmol/mg, of SM (d18:2/16:0(OH)) at least 0.3 pmol/mg, of Cer (d18:0/16:1) at most 0.2 pmol/mg and of Cer (d18:1/18:1) at most 0.3 pmol/mg of the *Cordyceps* sample.

The present invention further refers to a method of identifying a *Cordyceps* derivate, namely a *Cordyceps* derivate referenced as *Cordyceps sinensis*, *Hirsutella sinensis*, *Cephalosporium sinensis*, *Mortierella* SP or *Gliocadium roseum* herein in a *Cordyceps* sample. Said method comprises identifying and/or quantifying at least one sphingolipid in a *Cordyceps* sample as described above including preferred embodiments described above, preferably identifying and quantifying at least one sphingolipid in a *Cordyceps* sample. Preferably, the at least one sphingolipid is at least one of table 5, more preferably at least two of them, in particular at least three of them and more preferably all of them are identified and preferably identified and quantified.

TABLE 5 preferred sphingolipids for identifying *Cordyceps* derivates with preferred reference values

| *Cordyceps* derivate | Sphingolipid | Preferred reference value (amount of sphingolipid) for *Cordyceps* derivate in pmol/mg of the *Cordyceps* sample |
|---|---|---|
| *Hirsutella sinensis* | HexCer (t19:1/16:1) | 4.416 ± 0.619 |
| | HexCer (d19:2/16:0(OH)) | 5.436 ± 0.638 |
| | So (d18:1) | 3.023 ± 0.423 |
| | Sa (d16:0) | 0.014 ± 0.006 |
| | So (t22:2) | 0.252 ± 0.071 |
| | So (d20:1) | 2.329 ± 0.583 |
| | Cer (d18:1/16:1) | 12.510 ± 1.138 |
| | Cer (d18:1/18:1) | 1.227 ± 0.845 |
| | Cer (d18:2/18:1) | 0.009 ± 0.005 |
| | SM (d14:1/20:0) | 11.618 ± 2.342 |
| | Sa (t18:0) | 0.107 ± 0.049 |
| *Cordyceps sinensis* | Sa (d16:0) | 12.732 ± 0.724 |
| | HexCer (d19:2/16:0(OH)) | 10.203 ± 1.147 |
| | PI-Cer (d18:0/16:0(OH)) | 6.977 ± 1.505 |
| | So (t22:2) | 10.170 ± 0.732 |
| | So (d20:1) | 12.913 ± 0.829 |
| | Cer (d19:2/16:0(OH)) | 10.203 ± 1.147 |
| | Cer (d18:1/16:1) | 11.865 ± 1.381 |
| | Cer (d18:2/18:1) | 0.118 ± 0.035 |
| | Cer (d18:1/18:1) | 0.446 ± 0.396 |
| | Sa (t18:0) | 0.674 ± 0.121 |
| | Sa (t18:0) isomer | 2.373 ± 0.210 |
| *Cephalosporium sinensis* | SM (d18:2/16:0(OH)) | 0.017 ± 0.031 |
| | Cer (d18:1/18:1) | 12.008 ± 2.387 |
| | Cer (d18:0/18:0) | 9.885 ± 3.149 |
| | Cer (d18:1/16:1) | 1.109 ± 0.309 |
| | HexCer (d19:2/16:0(OH)) | 0.547 ± 0.802 |
| | Sa (d16:0) | 0.33 ± 0.174 |
| | Cer (d19:2/16:0(OH)) | 0.547 ± 0.802 |
| | Cer (d18:2/16:1) | 1.008 ± 0.299 |
| | So (d16:1) | 0.375 ± 0.223 |
| | Sa (t18:0) | 0.261 ± 0.121 |
| | So (t18:1) | 0.107 ± 0.062 |
| | Cer (d18:1/14:1) | 0.053 ± 0.016 |
| *Mortierella* SP | Cer (d18:0/16:1) | 0.616 ± 0.110 |
| | SM (d18:2/18:0) | 0.145 ± 0.051 |
| | SM (d18:2/16:0(OH)) | 0.054 ± 0.016 |
| | HexCer (t19:1/16:1) | 0.056 ± 0.018 |
| | Cer (d18:2/18:1) | 0.543 ± 0.083 |
| | SM (d14:1/20:0) | 1.080 ± 0.410 |
| | Sa (d16:0) | 0.068 ± 0.033 |
| | Cer (d19:2/16:0(OH)) | 3.820 ± 2.451 |
| | Cer (d18:2/16:1) | 2.350 ± 0.452 |

TABLE 5-continued preferred sphingolipids for identifying *Cordyceps* derivates with preferred reference values

| *Cordyceps* derivate | Sphingolipid | Preferred reference value (amount of sphingolipid) for *Cordyceps* derivate in pmol/mg of the *Cordyceps* sample |
|---|---|---|
| | Cer (d18:1/18:1) | 3.823 ± 1.802 |
| | So (d16:1) | 1.317 ± 0.340 |
| | Sa (t18:0) | 0.392 ± 0.096 |
| | So (t18:1) | 0.196 ± 0.078 |
| *Gliocadium roseum* | Cer (d18:1/18:1) | 13.455 ± 0.594 |
| | Sa (d16:0) | 0.211 ± 0.005 |
| | Sa (m18:0) | 0.283 ± 0.024 |
| | Sa (t18:0) | 4.544 ± 0.177 |
| | Sa (t18:0) isomer | 10.881 ± 0.455 |
| | So (t18:1) | 0.929 ± 0.065 |
| | Cer (d18:1/14:1) | 0.141 ± 0.004 |
| | Cer (d18:2/18:1) | 0.029 ± 0.018 |

The method of identifying a *Cordyceps* derivate in a *Cordyceps* sample preferably comprises steps of
a) identifying and quantifying at least one and preferably more than one sphingolipid in a *Cordyceps* sample as described above, in particular identifying and quantifying the sphingolipids given in table 5;
b) determining at least one *Cordyceps* derivate indicative parameter which is in particular the amount of a sphingolipid in table 5 in pmol/mg of the *Cordyceps* sample, preferably more than one *Cordyceps* derivate indicative parameter, namely the amounts of more than one sphingolipid and in particular all sphingolipids given in table 5;
c) comparing the *Cordyceps* derivate indicative parameter with a respective reference value, in particular the reference values given in table 5;
wherein an at least one and preferably two or more than two *Cordyceps* derivate indicative parameters, in particular all listed in table 5, corresponding to the respective reference values, in particular presence of the sphingolipid(s) in the amount(s) as respective reference value(s) listed in table 5, indicates that the respective *Cordyceps* derivate is present in the *Cordyceps* sample.

Further contemplated by the present invention is a method for determining indicative parameters for wild-type *Cordyceps* (i.e. *Cordyceps* wild-type indicative parameters) or indicative for *Cordyceps* derivates (i.e. *Cordyceps* derivate indicative parameters), in particular relating to the presence, amount or ratio of certain sphingolipids as markers which method comprises:
a) identifying and quantifying at least one and preferably more than one sphingolipid in a first *Cordyceps* sample selected from a *Cordyceps* sample comprising wild-type *Cordyceps* or a *Cordyceps* sample comprising a first *Cordyceps* derivate;
b) identifying and quantifying said at least one and preferably more than one sphingolipid in a second *Cordyceps* sample of a *Cordyceps* derivate and a second *Cordyceps* derivate, respectively;
c) optionally identifying and quantifying said at least one and preferably more than one sphingolipid in further *Cordyceps* samples each comprising further *Cordyceps* derivates;
d) comparing the presence of the at least one sphingolipid, preferably the sphingolipid pattern and/or the amount of the at least one sphingolipid or ratio of sphingolipids in the respective *Cordyceps* samples;
e) defining *Cordyceps* wild-type indicative parameters and/or *Cordyceps* derivate indicative parameters and respective reference values.

The *Cordyceps* wild-type indicative parameters and/or *Cordyceps* derivate indicative parameters defined in step e) can be used for quality control and identification of wild-type *Cordyceps* or any *Cordyceps* derivates in *Cordyceps* samples.

EXAMPLES

Example 1

Preparation of Standard References and *Cordyceps* Samples

Methanol (LC-MS grade), isopropanol (LC-MS grade) and chloroform (HPLC grade) were purchased from Avantor Performance Materials, Lnc. (Center Valley, Pa., USA). Formic acid (LC-MS grade), acetic acid (LC-MS grade), ammonium acetate (purity≥98%) and potassium hydroxide (KOH, purity 85%) were purchased from Sigma-Aldrich (St. Louis, Mo., USA). Distilled water was prepared using a Milli-Q system (Millipore, Billerica, Mass.).

Example 1A

Preparation of the Internal Standard

An internal standard cocktail (Internal standards mixture II, 25 µM of each compound in ethanol) containing C17-sphingosine [So (d17:1)], C17-sphinganine [Sa (d17:0)], C17-sphingosine-1-phosphate [SIP (dl 7:1)], C12-ceramide [Cer (dl 8:1/12:0)], C12-sphingomyelin [SM (d18:1/12:0)] and C12-glucosylceramide [GlcCer (d18:1/12:0)] was purchased from Avanti Polar Lipids (Alabaster, Ala., USA). SPL standards including Cer (d18:1/6:0), Cer (d18:1/18:0), Cer (18:1/22:0), Cer (d18:1/24:0), SM (d18:1/17:0) and SM (d18:1/24:0) were also obtained from Avanti. So (d14:1), So (d20:1) and SM (d18:1/20:0) were obtained from Matreya LLC (Pleasant Gap, Pa., USA).

The stock solution of internal standard cocktail (I.S. 25 µM) was prepared sequentially to afford a series of working solutions (0.05, 0.125, 0.25, 0.5, 1.25, 2.5, 5, 12.5, 25, 37.5 and 50 µM). A mixture standard stock solution was prepared by dissolving the nine standards in methanol to a final concentration of 50 µM. This standard stock solution was then diluted to yield a series of working solutions of 0.5, 1, 2, 5, 10, 25 and 50 µM.

Example 1B

Preparation of the Test Sample Solution from the *Cordyceps* Sample

Wild-type *Cordyceps* were purchased from Qinghai Province and Wai Yuen Tong Medicine Company Limited (Hong Kong) in August 2013. Each wild-type *Cordyceps* included the whole wild-type. In addition, two isolated parts cut from the whole wild-type *Cordyceps*, namely the fruiting body and the *sclerotium* were provided. The *Cordyceps* derivates *Cordyceps sinensis* were from Jiangxi Jiminkexin Pharmaceutical Co., Ltd.; *Hirsutella sinensis* were from Hangzhou Zhongmei Huadong Pharmaceutical Co., Ltd.; *Gliocadium roseum* were from Hebei Changtian Pharmaceutical Co., Ltd.; *Mortierella* SP were from Hangzhou Tianyuan Pharmaceutical Co., Ltd. and Datong Liqun Pharmaceutical Co., Ltd.; *Cephalosporium sinensis* were from Yunnan Baiyao Group Lijiang Pharmaceutical Co. Ltd., Shenyang Dongxin Pharmaceutical Co., Ltd., Hunan Kangerjia Pharmaceutical Co., Ltd., Guizhou Liangji Pharmaceutical Co., Ltd. and Jiangsu Shenhua Pharmaceutical Co., Ltd.

Test sample solutions were prepared and measurement has been carried out in accordance with the following procedures.

35 mg of powdered *Cordyceps* sample was accurately weighed into a glass bottle. In which extraction solvent 1 [0.75 mL chloroform/methanol (1:2, v/v)] and 10 µL 2.5 µM IS were subsequently added. The mixture was dispersed by applying an ultrasonicator for 30 s and incubated at 48° C. for 12 h. After incubation, 75 µL of KOH in methanol (1 M) was added and the mixture was incubated at 37° C. for 2 h. The resultant mixture was then neutralized with acetic acid and centrifuged. The supernatant was collected and the residue was re-extracted with a second extracting solvent [1 mL chloroform/methanol (2:1, v/v)] and a third extracting solvent [0.4 mL chloroform/methanol (1:2, v/v), 1 mL chloroform and 2 mL $H_2O$], sequentially. The first two supernatants and the third lower layer were combined and $N_2$ dried. All extracts were reconstituted in 150 µL methanol. All solutions were filtered through a 0.22 µm filter before analysis.

Example 2

Identification and Quantification of Sphingolipids in *Cordyceps* Samples

Example 2A

LC-MS Analysis and MS Analysis

Liquid chromatography-mass spectrometric (LC-MS) analysis was performed with optimized LC-MS conditions. Chromatographic separation was performed on an Agilent 1290 Infinity UHPLC system (Santa Clara, Calif., USA) equipped with a binary solvent delivery system and a standard autosampler. An Agilent Eclipse Plus C18 column (100×2.1 mm, 1.8 µm) was employed to separate SPLs. Detection of SPLs was performed on an Agilent 6550 Q-TOF mass spectrometer (Santa Clara, Calif., USA). The Jet Stream electrospray ionization source was operated in positive ion mode. Quantitative analysis was carried out in multiple reaction monitoring (MRM) mode using an Agilent 6460 QQQ mass spectrometer (Santa Clara, Calif., USA). The MRM transitions (precursor ion→product ion), fragmentor voltages, and CE values selected for each individual SPLs were those given in Table 6.

The dynamic MRM data were processed with Agilent Mass Hunter Workstation Software. Quantitative results of SPLs in samples were calculated based on below formula:

Level(targeted SPL)=25 pmol×[Area(targeted SPL)/Area(IS)].

The quantitative data of wild-type *Cordyceps* and *Cordyceps* derivates were converted into Microsoft Excel format and imported into SIMCA 14.0 software (version 14.0, Umetrics, Umea, Sweden) for multivariate analysis. Variables significantly changed among different samples were selected based on VIP≥1 and the validated by using T-test analysis.

Example 2B

Method Validation

Linearity was determined by spiking 6 internal standards (IS) into samples prior to extraction. Triplicates of each IS were prepared and analyzed at no less than nine appropriate concentration levels. Calibration curves were constructed by linear regression. Linearity was verified by correlation coefficients ($r^2$). The lowest concentration in the calibration curve was further diluted for Limit of Quantitation (LOQ) and Limit of Detection (LOD) tests. LOD and LOQ were defined as the lowest concentration when signal-to-noise ratios (S/N) of about 3 and 10 was obtained, respectively.

The precision of injection was evaluated using 6 replicate injections of the sample solution. The intra- and inter-day precision of the quantitative procedure were determined based on the results of 6 analyses of samples within a day and 9 analyses of samples on three consecutive days. All precision were obtained by calculating the relative standard deviations (RSD) for the levels of endogenous SPLs in samples.

Recovery was examined by comparing signal response of IS spiked into samples before and after SPLs extraction at three different levels. At each level, six replicates of samples were prepared. Mean recovery and RSDs were calculated to verify the extraction efficiency of IS.

The stability of each analyte in sample solution was tested by measuring the levels directly after sample preparation and at different time intervals, after storage at 4° C. The stability of the system was evaluated using quality control samples (QC, the sample was pooled with equal volume of all analysis samples) which were analyzed across the whole analysis process. All validation parameters were evaluated by calculating RSDs.

The quantitative accuracy of the method was validated by investigating the linear correlation between the added and determined amount of individual SPLs in the samples. In the test, a fixed amount of IS (25 pmol) and the amounts of sphingolipid standard varied from 0 to 500 pmol were spiked into a series of samples prior to extraction. The levels of individual SPLs spiked in samples were determined after removal of the pre-determined levels in samples.

Example 2C

Result of the Identification of Sphingolipids in *Cordyceps* Samples

Based on the method of present invention, sphingolipids (SPLs) in *Cordyceps* samples were identified on the basis of high-resolution MS and MS/MS data, matching of SPLs with comprehensive SPL database, and confirmation of SPL standards. As the result, a total of 101 SPLs were identified from a pooled sample of five *Cordyceps* derivates, as shown in Table 7, including 10 sphingosines (So), 6 sphinganines (Sa), one sphingoid base 1-phosphate (S1P), one lysosphingomyelin (S1Po), 51 ceramides (Cer), 8 hexosyl ceramides (HexCer), 19 sphingomyelins (SM), 3 inositol phosphorylceramides (PI-Cer) and 2 mannosylinositol phosphorylceramides (MIPC). It can be seen that Cer are the most diverse SPL in mycelia, followed by SM and So. Among the 101 identified SPL, 88 species were also identified in wild-type *Cordyceps*.

Example 2D

Method Validation for Quantitative Analysis

To quantitatively profile the SPLs, a MRM-based method was performed in accordance with the method as described in Wang, J. R. et al. *Anal. Chem.* 2014, 86, 5688-5696. The method was further validated for the quantification of SPLs in wild-type *Cordyceps* and *Cordyceps* derivates related to wild-type *Cordyceps*.

Linearity, LOD and LOQ were determined. As shown in Table 8, all 6 calibration curves exhibited good linearity ($r^2 \geq 0.9977$) over wide dynamic ranges which spanned more than 2 orders of magnitude. The LOD ranged between 0.005 and 3.34 nM, whereas LOQ ranged between 0.0167 and 16.7 nM, suggesting that the method is highly sensitive for simultaneous quantification of a complete panel of SPLs.

Injection precision, intra- and inter-day precisions were evaluated. As shown in Table 6, the RSDs of the levels of all quantified endogenous SPLs in samples were less than 6% for injection precision tests. Satisfactory RSD median values (3.79% and 3.96%) were achieved for intra- and inter-day precisions, demonstrating acceptable precision of the method for SPLs analysis.

Stability was examined. As shown in Table 6, The RSDs for the levels of approximately 90% endogenous SPLs in samples were less than 10% for stability tests. The RSDs for the levels of over 90% endogenous SPLs in QC samples were less than 15% across the whole process.

Recovery was examined. As shown in Table 8, mean recovery of 87.05%, 83.72%, 81.70%, 100.15%, 99.42% and 88.43% were achieved, respectively, for IS So (d17:1), S1P (d17:1), Sa (d17:0), Cer (18:1/12:0), GlcCer (d18:1/12:0) and SM (d18:1/12:0). RSD values of the recoveries of all IS at all spiking levels were less than 5%.

The quantitative accuracy of the method was further validated. As shown in FIG. 7A to 7I, a good correlation between the added and determined amounts of individual SPLs with different carbon chains was confirmed. The fitting equation slopes were between 0.95 and 1.08 and correlation coefficients $r^2 \geq 0.991$. The data suggested that the method is suitable to quantify alterations in the mass content of individual SPLs, and demonstrated a good accuracy of our method for quantification of changes over a wide range (5-500 pmol).

Example 2E

Quantitative Comparison of Sphingolipids in *Cordyceps* Samples

By using the validated method, a total of 101 SPLs in wild-type *Cordyceps* and *Cordyceps* derivates were quantitatively profiled. With reference to FIG. 1, there is illustrated the overall distribution of SPLs with the total contents of the four subgroups of SPLs. According to results, there is a rank order of sphingoid bases>ceramides> phosphosphingolipids>> glycosphingolipids in wild-type *Cordyceps*, and a different order (ceramides>sphingoid bases>>phosphosphingolipids/glycosphingolipids) in most *Cordyceps* derivates. Regarding *Cordyceps* derivates, some special distribution features were observed for *Cordyceps sinensis* and *Hirsutella sinensis*.

In *Cordyceps sinensis*, sphingoid bases were relatively rich and their total content was higher than that of ceramides, which is a reversed rank order of sphingoid bases and ceramides for the other *Cordyceps* derivates. In *Hirsutella sinensis*, however, the total content of sphingoid bases was notably low whereas the abundance of phosphosphingolipids was relatively high, which led to a reversed rank order of sphingoid bases and phosphosphingolipids for the other *Cordyceps* derivates.

The quantitative results also revealed distribution pattern of individual SPLs of wild-type *Cordyceps* and *Cordyceps* derivates, which is described by the subgroups further below.

Example 2F

Sphingoid Bases in *Cordyceps* Samples

Figure 2A:
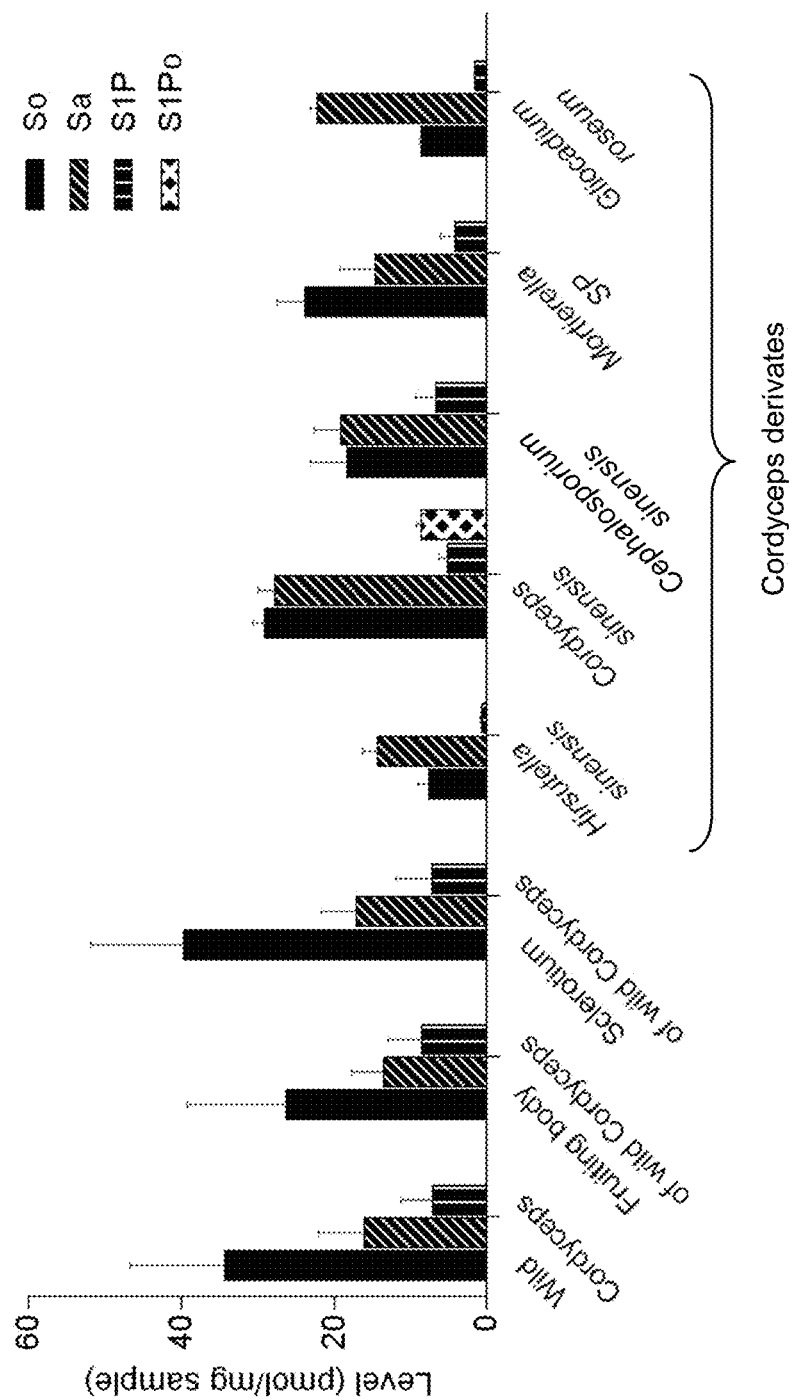
FIG. 2A shows the total levels of subgroups of sphingoid bases, namely So, Sa, S1P and S1Po, in the *Cordyceps* samples (each bar represents mean±SD) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.
Figure 2B:
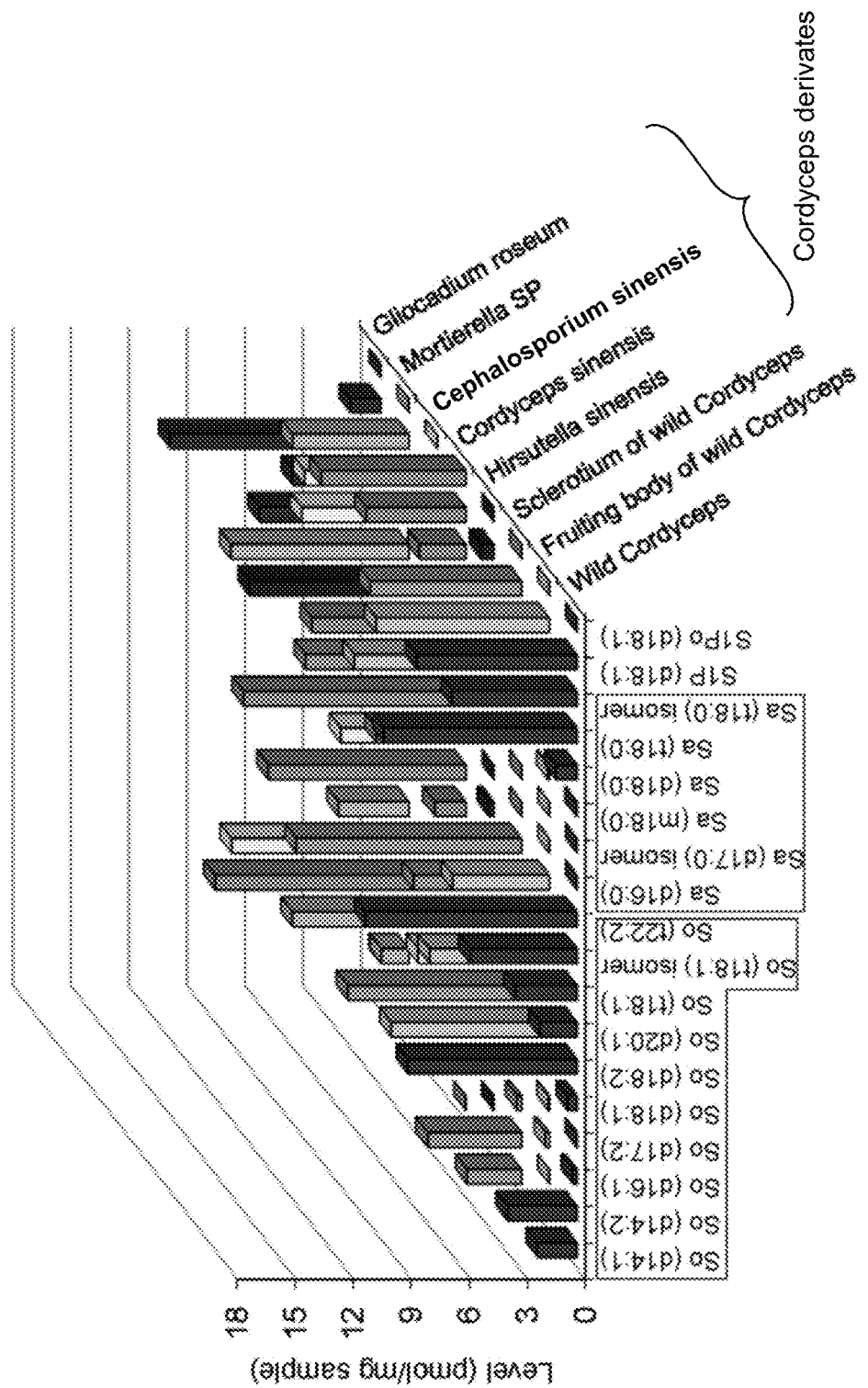
FIG. 2B shows the levels of 18 sphingoid bases in the *Cordyceps* samples (each bar represents mean value of individual sphingoid bases) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.

A total of 18 sphingoid bases were quantified, including 10 So, 6 Sa, one S1P and one S1Po (FIGS. 2A-2B). Levels of the four subclasses in both wild-type *Cordyceps* and *Cordyceps* derivates were generally in an order of So>Sa>S1P>S1Po, except for *Hirsutella sinensis* and *Gliocadium roseum*, in which Sa was more abundant than So and the content of S1P was extremely low (as low as 0.66 and 1.56 pmol/mg, vs about 7.17 pmol/mg in other samples).

Structurally, sphingoid bases with carbon chain length 18 were more abundant than those species with carbon chain length<18 in terms of both number of species and content in all samples. When comparing different samples, the total content of sphingoid bases was found to be the highest in *Cordyceps sinensis*, followed by wild-type *Cordyceps* (including individual part of fruiting body of the wild-type *Cordyceps* and individual part of *sclerotium* of the wild-type *Cordyceps*), *Cephalosporium sinensis*, *Mortierella* SP, *Gliocadium roseum* and *Hirsutella sinensis*. Of note, the total content of sphingoid bases in *Cordyceps sinensis* was more than 3-folds of that in *Hirsutella sinensis*, clearly showing a large difference in the level of sphingoid bases among the *Cordyceps* samples.

Example 2G

Ceramides in *Cordyceps* Samples

Figure 3A:
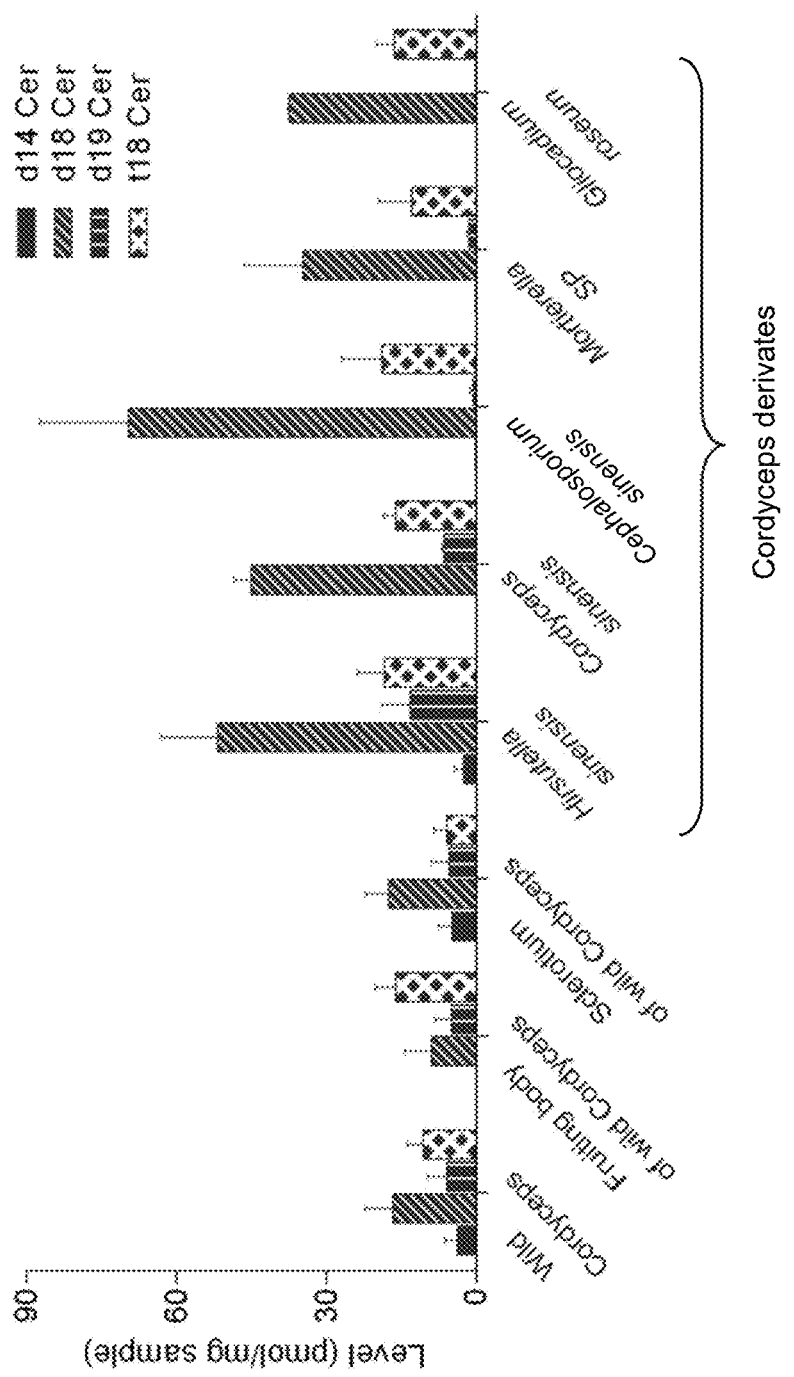
FIG. 3A shows the total levels of subgroups of ceramides, namely d14 Cer, d18 Cer, d19 Cer and t18 Cer, in the *Cordyceps* samples (each bar represents mean±SD) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.
Figure 3B:
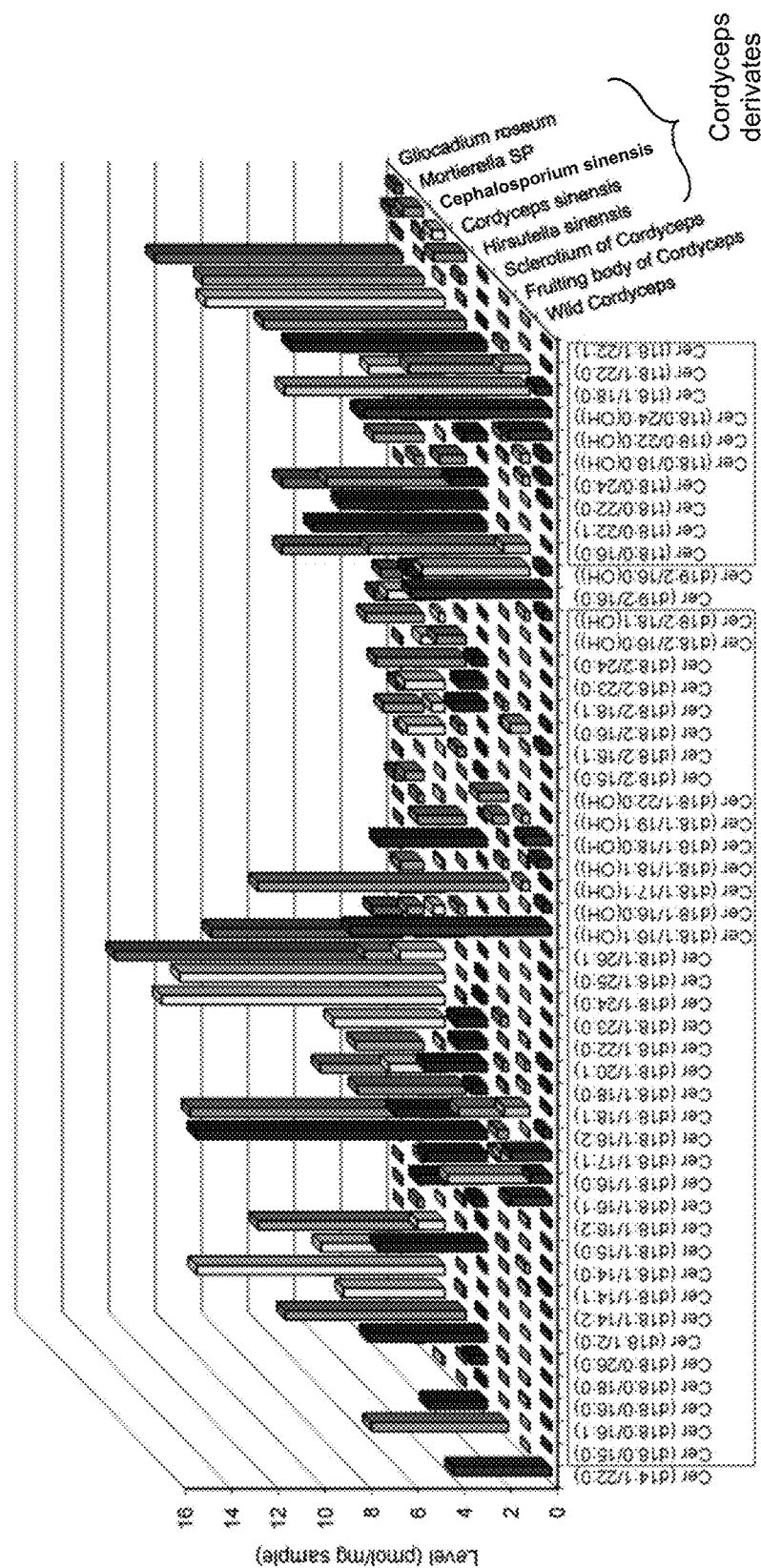
FIG. 3B shows the levels of 51 ceramides in the *Cordyceps* samples (each bar represents mean value of individual ceramides) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.

Ceramides were the most structurally diverse species. A total of 51 ceramides were quantitatively determined (FIGS. 3A-3B). It can be seen that ceramides with d18 sphingoid base backbone were the most structurally diverse (28-38 species) and represents the dominant species, followed by those species with t18 sphingoid base backbone (9-10 species, with content of approximately 30% of that of d18 species). Of note, two uncommon Cers with odd-numbered sphingoid base backbone [Cer (d19:2/16:0) and Cer (d19:2/16:0(OH))] and one Cer with very short chain length sphingoid base backbone (d14) were found as low-abundance species in most samples. The d19 species was relatively rich in *Hirsutella sinensis* and wild-type *Cordyceps*.

Comparison of the total content of Cer among samples suggested that *Cephalosporium sinensis* has the highest content of Cer, followed by other *Cordyceps* derivates, whereas wild-type *Cordyceps* has the lowest content of Cer.

Example 2H

Phosphosphingolipids in *Cordyceps* Samples

Figure 4A:
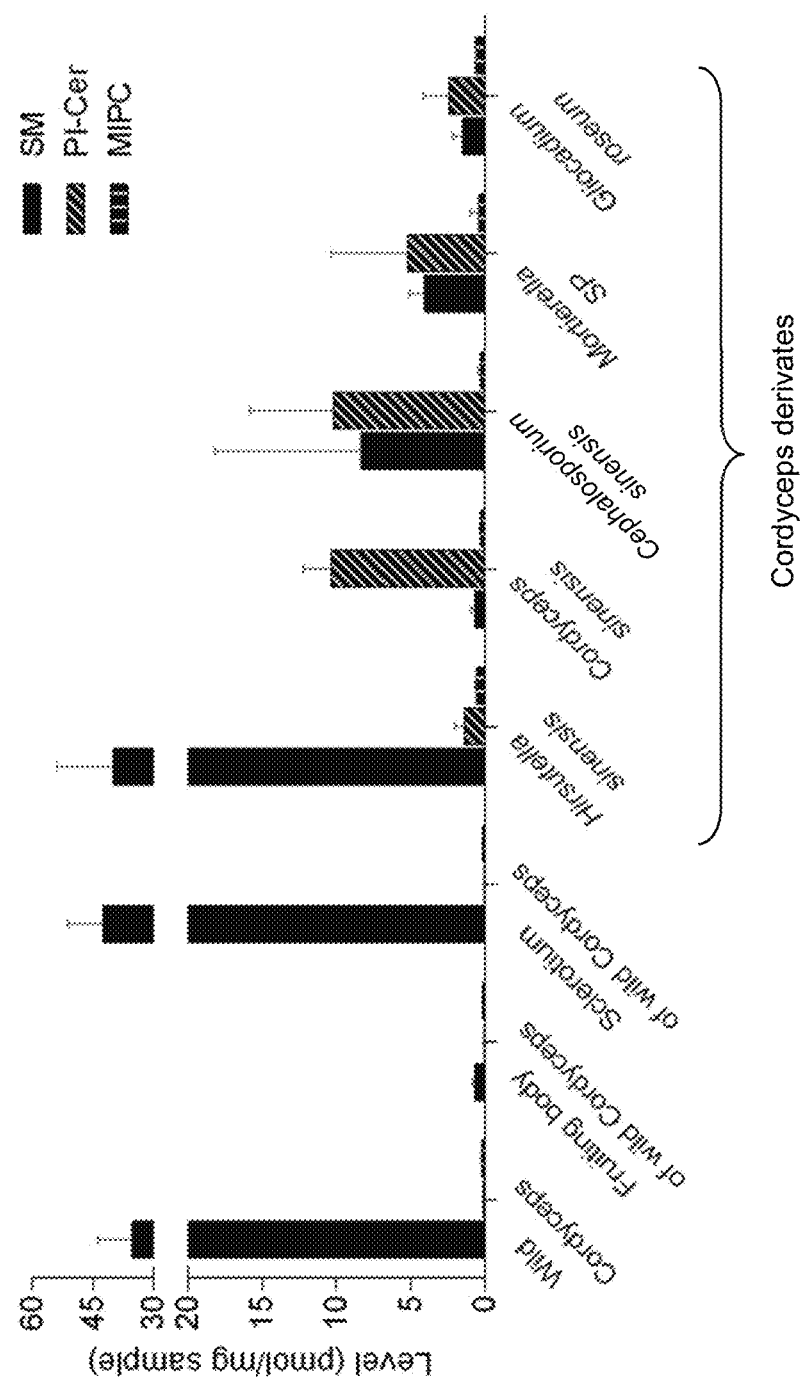
FIG. 4A shows the total levels of subgroups of phosphosphingolipids, namely SM, Pl-Cer and MIPC, in the *Cordyceps* samples (each bar represents mean±SD) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.
Figure 4B:
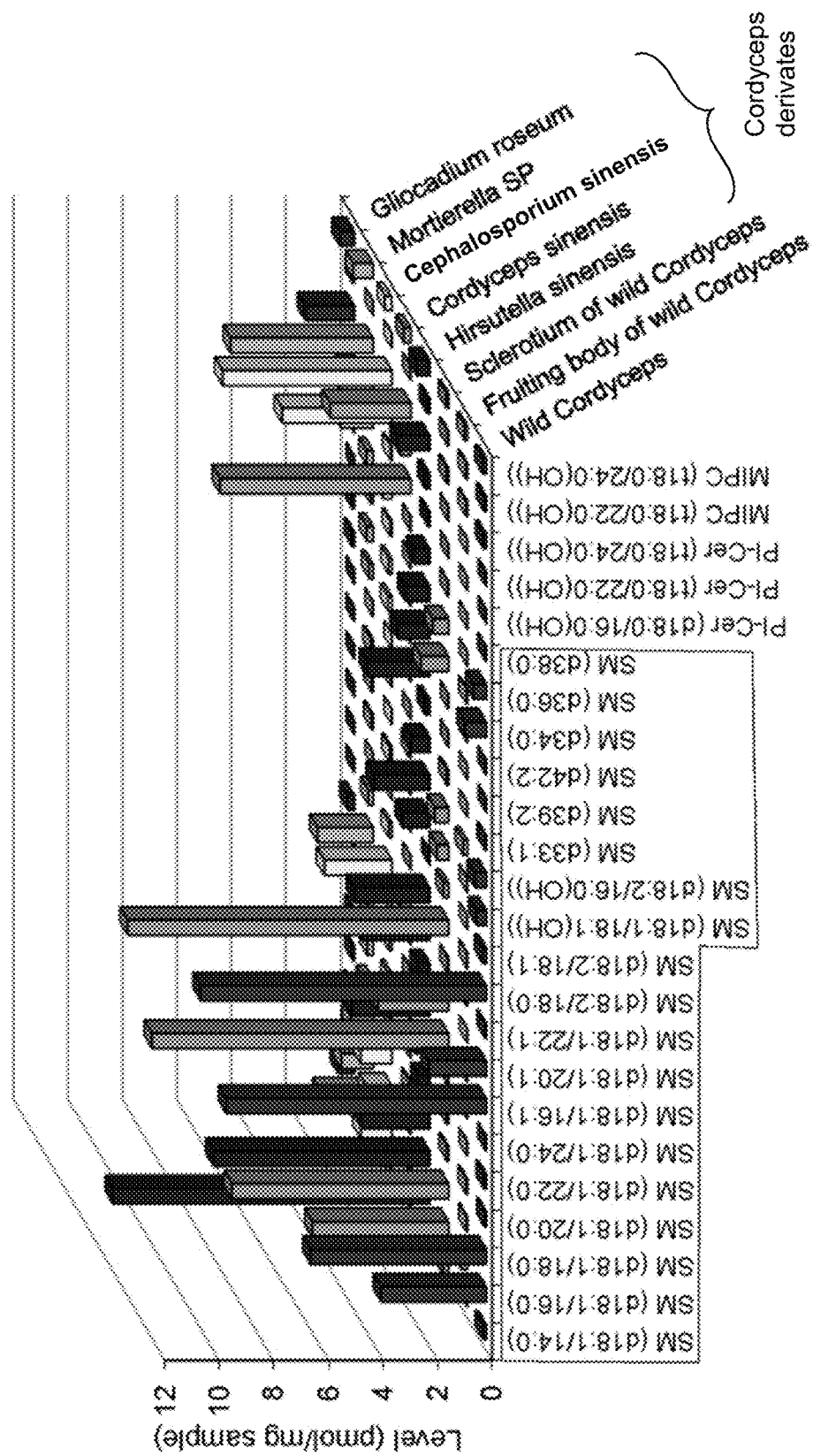
FIG. 4B shows the levels of 24 phosphosphingolipids in the *Cordyceps* samples (each bar represents mean value of individual phosphosphingolipids) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.

As shown in FIGS. 4A-4B, a total of 24 phosphosphingolipids belonging to three subclasses were measured, including 19 SMs, 3 Pl-Cer and 2 MIPCs. In both wild-type *Cordyceps* and *Cordyceps* derivates, SMs and/or Pl-Cer were dominant species whereas MIPCs were minor SPLs. Even though, the levels of SMs and Pl-Cer varied remarkably.

In *Cordyceps sinensis*, the abundance of SM (0.69 pmol/mg) was about 14-folds lower than that of Pl-Cer (10.32 pmol/mg), while in *Cephalosporium sinensis*, *Gliocadium roseum* and *Mortierella* SP, the total content of SM (about 1.5-8.3 pmol/mg) was comparable to that of Pl-Cer (2.4-10.2 pmol/mg). However, different from both *Cordyceps sinensis* and *Cephalosporium sinensis* etc, the level of SM in *Hirsutella sinensis* and wild-type *Cordyceps* was notably high (about 35-42 pmol/mg), while Pl-Cer was much less (about 0.1-1.4 pmol/mg).

Example 21

Glycosphingolipids in *Cordyceps* Samples

Figure 5A:
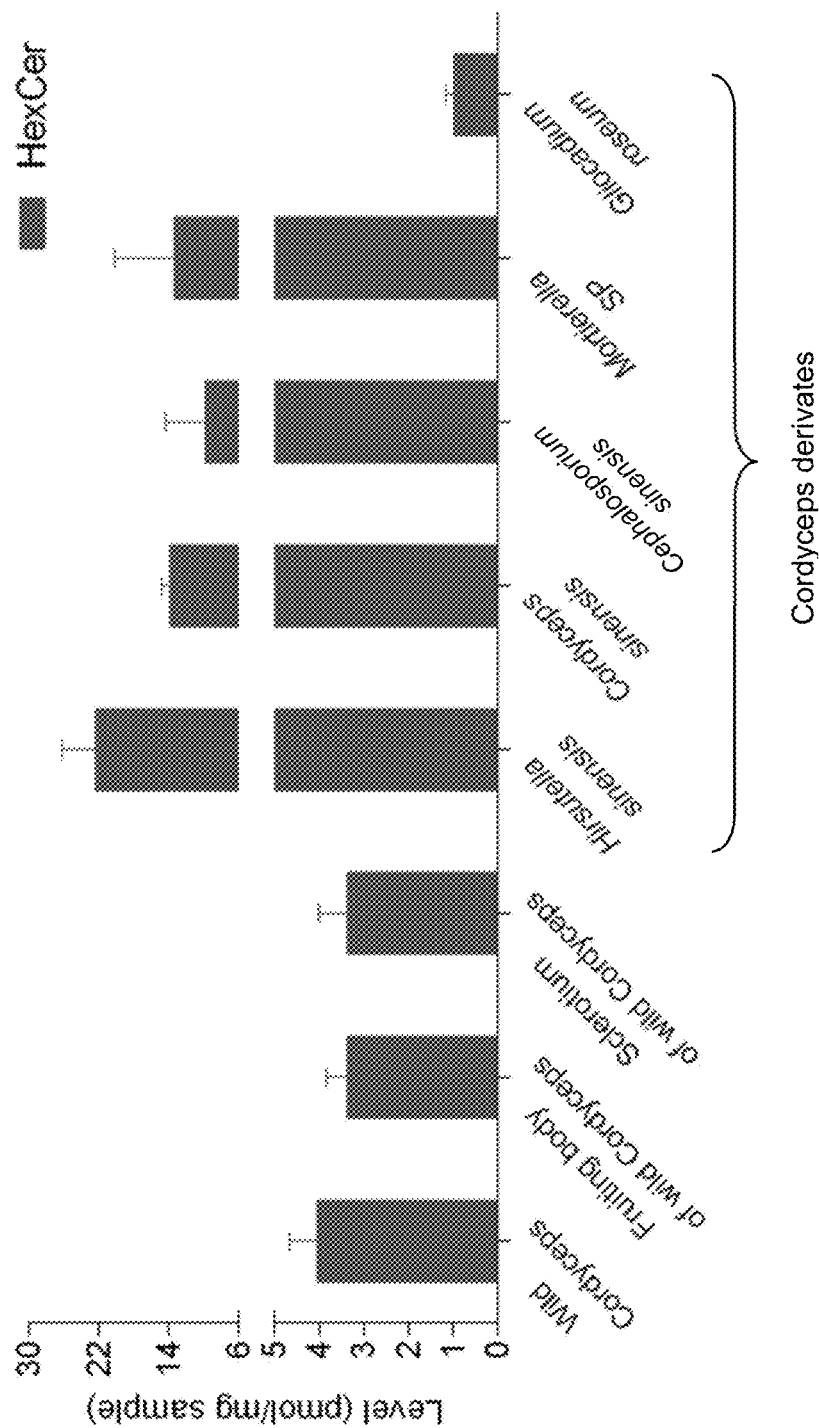
FIG. 5A shows the total level of HexCer in the *Cordyceps* samples (each bar represents mean±SD) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.
Figure 5B:
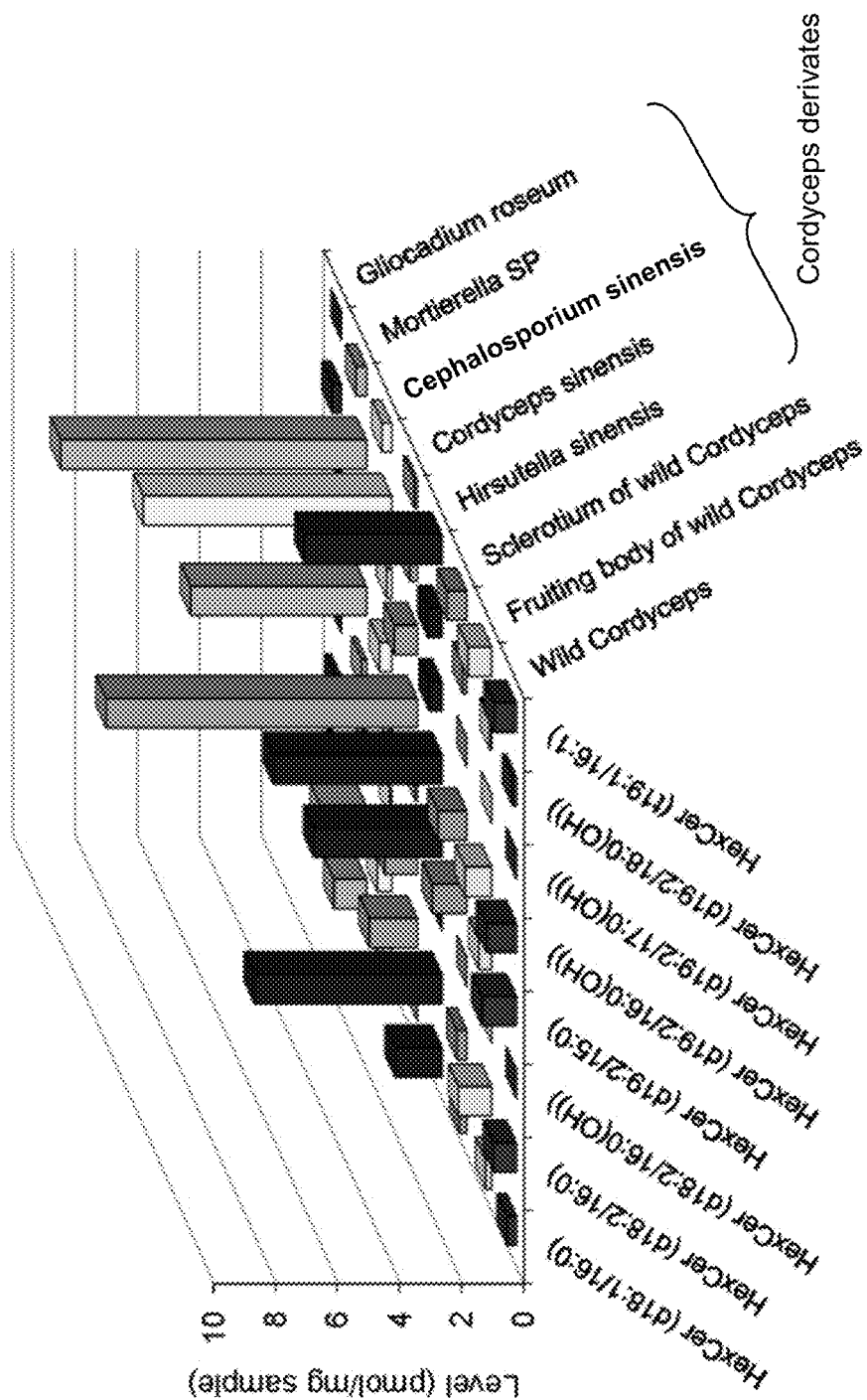
FIG. 5B shows the levels of 8 glycosphingolipids in the *Cordyceps* samples (each bar represents mean value of individual glycosphingolipids) including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.

Glycosphingolipids observed in all samples belong to the subclass of HexCer. Among which, species with sphingoid base bone of d19:2 accounted for majority of the structures (more than 80%). A total of 8 HexCer were quantified and the results were shown in FIG. 5A-5B.

It can be seen that in all samples, the total levels of HexCer in *Cordyceps* derivates were generally 2-5 folds of that in wild-type *Cordyceps*, except for *Gliocadium roseum* of which the HexCer abundance was even lower than wild-type *Cordyceps*.

Example 2J

Comparing SPLs in Wild-Type *Cordyceps* with *Cordyceps* Derivates

Supervised partial least squares discriminant analysis (PLS-DA) model was employed to visualize the general classification of samples so as to further differentiate each of the sample from the others.

Figure 6A:
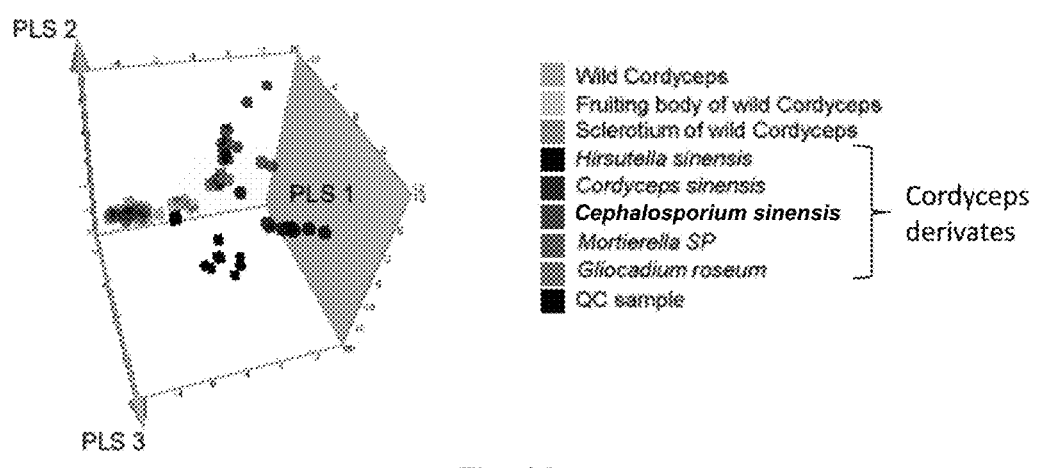
FIG. 6A shows a partial least squares discriminant analysis (PLS-DA) score scatter 3D plot of the sphingolipids in the *Cordyceps* samples including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.

As shown in FIG. 6A, QC samples employed in the analysis were clustered into one group in the PLS-DA score scatter 3D plot, demonstrating acceptable reproducibility of the quantitative analysis data. It can be seen that wild-type *Cordyceps* was separated from *Cordyceps* derivates at PLS 1 vector, *Hirsutella sinensis* was separated from others at PLS 2 vector, and *Cordyceps sinensis*, *Cephalosporium sinensis* and other related species were separated at PLS 3 vector.

Figure 6B:
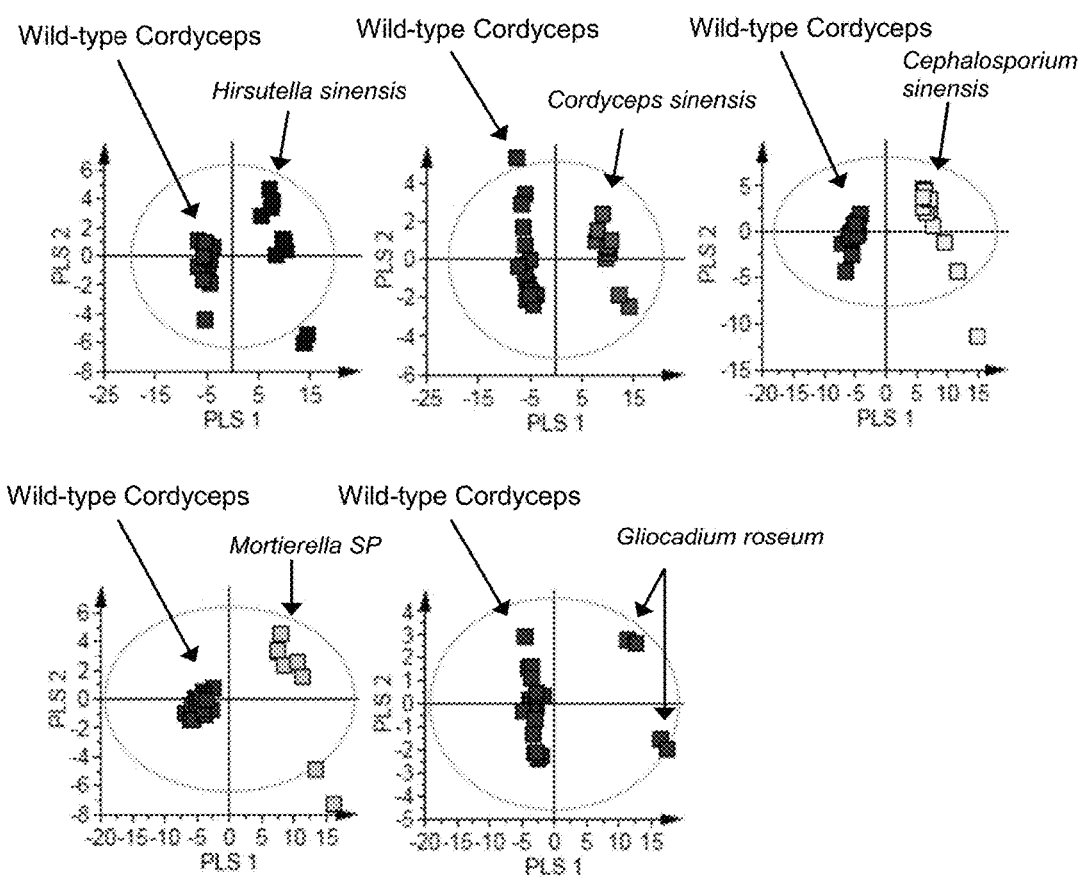
FIG. 6B shows PLS-DA score scatter 3D plots of the sphingolipids in the *Cordyceps* samples including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.

These results showed significant difference among sphingolipidomes of wild-type *Cordyceps* and *Cordyceps* derivates. PLS-DA was further performed for wild-type *Cordyceps* and *Cordyceps* derivates and the plot was shown in FIG. 6B. It can be seen that wild-type *Cordyceps* and *Cordyceps* derivates were separated from each other, showing that this model clearly distinguishes wild-type *Cordyceps* from *Cordyceps* derivates, and vice versa. The PLS-DA model has a high $R^2Y$ value of 0.55-0.66 and $Q^2$ value of 0.94-0.97, demonstrating a good predictability of the model. Based on PLS-DA analysis, the SPLs with VIP≥1 were selected as leading SPL, i.e. potential marker for quality and quantitative measures, and further confirmed by using T-test.

Example 2K

Identification of Sphingolipids Especially Suitable for Identifying Wild-Type *Cordyceps*

Sphingolipids especially suitable for identifying wild-type *Cordyceps*, i.e. potential markers, for the differentiation between wild-type *Cordyceps* and *Cordyceps* derivates including *Hirsutella sinensis*, *Cordyceps sinensis*, *Cephalosporium sinensis*, *Mortierella* SP and *Gliocadium roseum* were selected in accordance with VIP values.

Figure 6C:
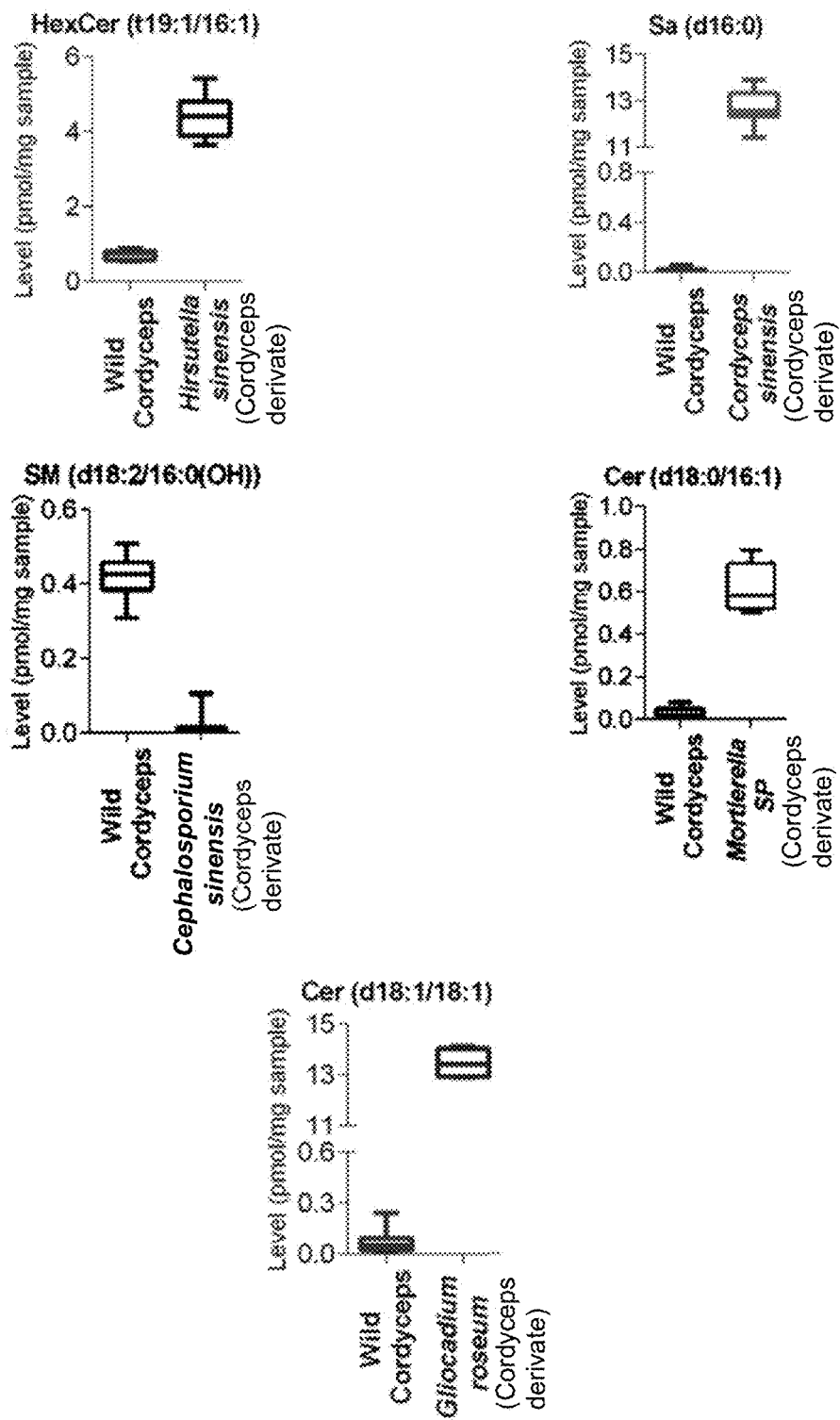
FIG. 6C shows the significance of representative sphingolipids obtained from multivariate statistical analysis among different *Cordyceps* samples including a *Cordyceps* sample with wild-type *Cordyceps* (whole caterpillar fungus), isolated parts from wild-type *Cordyceps*, namely the fruiting body or the *sclerotium*, and *Cordyceps* derivates, namely *Hirsutella sinensis, Cordyceps sinensis, Cephalosporium sinensis, Mortierella* SP and *Gliocadium roseum*.
Figure 7A:
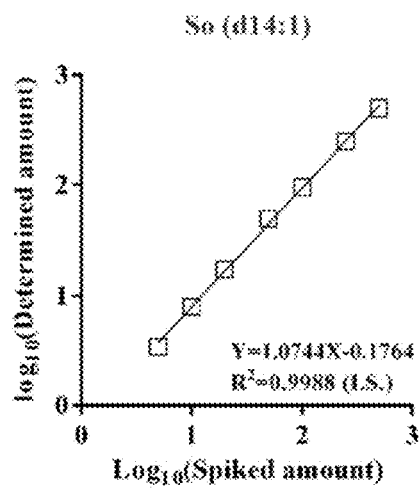
FIG. 7A to 7I show linear correlation of the added and determined amounts of individual sphingolipid standards with different carbon chains.
Figure 7B:
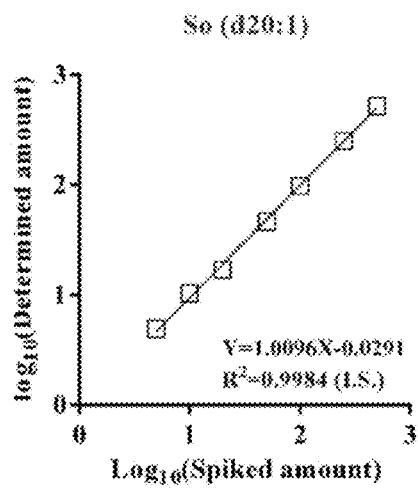
Figure 7C:
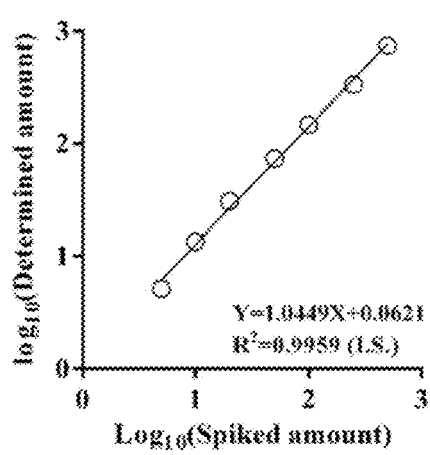
Figure 7D:
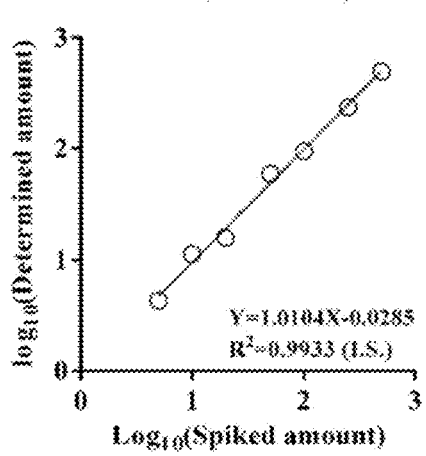
Figure 7E:
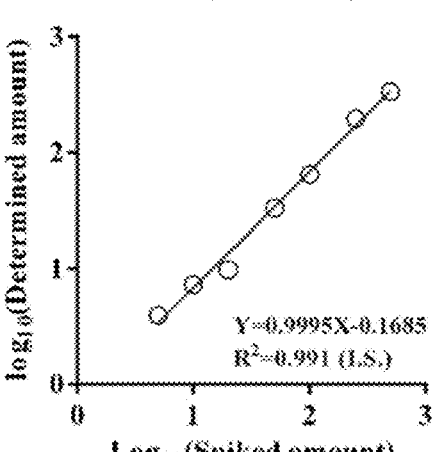
Figure 7F:
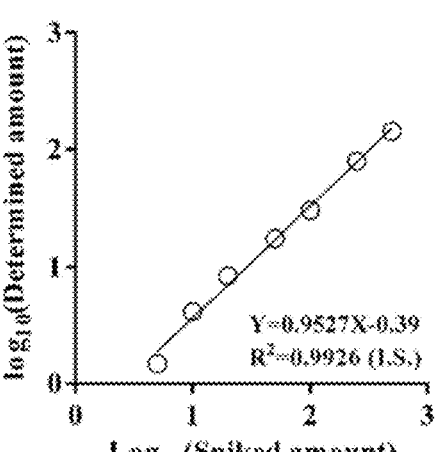
Figure 7G:
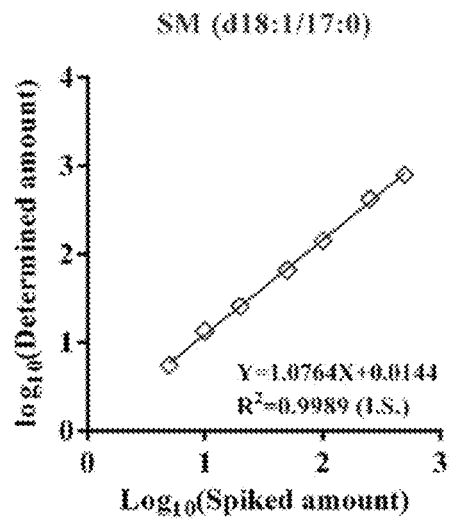
Figure 7H:
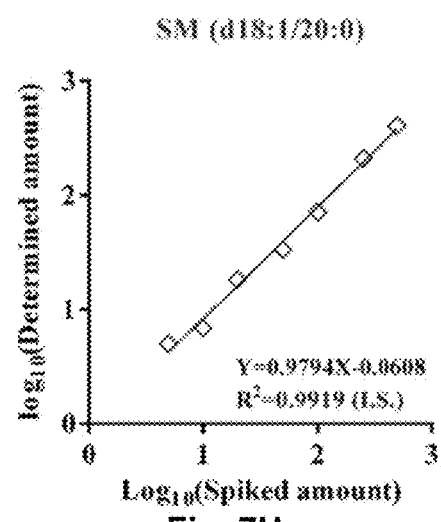
Figure 7I:
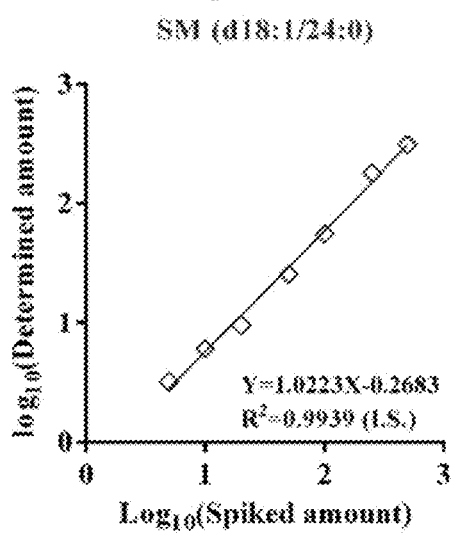

Among the results, three SPLs with the highest VIP values were selected to be the potential marker respectively (table 9). Significant differences of 5 representative markers [HexCer (t19:1/16:1), Sa (d16:0), SM (d18:2/16:0(OH)), Cer (d18:0/16:1) and Cer (d18:1118:1)] between wild-type *Cordyceps* and *Cordyceps* derivates were shown in FIG. 6C. Additionally, potential markers that confirmed with PLS-DA model analysis for differentiating *Cordyceps* derivates are also presented in Table 9, in which sphingoid bases was the highest contributing SPL for the classification of most *Cordyceps* derivates.

Accordingly, the present invention provides a method of quantitative profiling SPLs in wild-type *Cordyceps* and *Cordyceps* derivates being related to *Cordyceps*. It offers a robust method for evaluating the quality of wild-type *Cordyceps* and *Cordyceps* derivates in the aspect of sphingolipidomes. Based on multivariate analysis, respective sphingolipids were found as potential chemical markers for the differentiation of wild-type *Cordyceps* and different *Cordyceps* derivates. In addition, the present invention provides comprehensive chemical evidences for the pharmacological effects and clinical efficacy of wild-type *Cordyceps* and *Cordyceps* derivates.

TABLE 6

MRM parameters and validation data for the quantitation of 101 SPLs in wild-type *Cordyceps* and *Cordyceps* derivates

| SPLs | Subgroup | Internal No. | Name od SPL | RT (min) | MRM transitions (m/z) | Fragmentor (v) | CE* (v) |
|---|---|---|---|---|---|---|---|
| Sphingoid bases | So | IS-1 | So (d17:1) | 6.37 | 286.3→268.3 | 80 | 5 |
|  |  | 1 | So (d14:2) | 3.76 | 242.2→224.2 | 80 | 5 |
|  |  | 2 | So (d14:1) | 5.30 | 244.2→226.1 | 80 | 5 |
|  |  | 3 | So (d16:1) | 5.95 | 272.3→254.2 | 80 | 5 |
|  |  | 4 | So (d17:2) | 7.11 | 284.3→266.2 | 80 | 5 |
|  |  | 5 | So (d18:2) | 6.50 | 298.3→280.3 | 80 | 5 |
|  |  | 6 | So (d18:1) | 6.78 | 300.3→282.3 | 80 | 5 |
|  |  | 7 | So (t18:1) | 6.38 | 316.3→298.3 | 80 | 5 |
|  |  | 8 | So (t18:1) isomer | 6.90 | 316.3→298.3 | 80 | 5 |
|  |  | 9 | So (d20:1) | 9.41 | 328.3→310.3 | 80 | 5 |
|  |  | 10 | So (t22:2) | 9.13 | 370.3→352.3 | 80 | 5 |

TABLE 6-continued

MRM parameters and validation data for the quantitation of 101 SPLs in wild-type *Cordyceps* and *Cordyceps* derivates

| | | | | | | | |
|---|---|---|---|---|---|---|---|
| | | S1P | IS-2 | S1P (d17:1) | 6.55 | 366.2→250.3 | 105 | 10 |
| | | | 11 | S1P (d18:1) | 9.03 | 380.3→362.3 | 105 | 10 |
| | | S1Po[#] | 12 | S1Po (d18:1) | 6.55 | 467.4→449.3 | 105 | 10 |
| | | Sa | IS-3 | Sa (d17:0) | 6.57 | 288.3→270.3 | 110 | 20 |
| | | | 13 | Sa (d16:0) | 6.24 | 274.3→256.3 | 110 | 20 |
| | | | 14 | Sa (m18:0) | 7.12 | 286.3→268.3 | 110 | 20 |
| | | | 15 | Sa (d17:0) isomer | 5.51 | 288.3→270.3 | 110 | 20 |
| | | | 16 | Sa (d18:0) | 6.91 | 302.3→284.3 | 110 | 20 |
| | | | 17 | Sa (t18:0) | 6.61 | 318.3→300.3 | 110 | 20 |
| | | | 18 | Sa (t18:0) isomer | 6.32 | 318.3→300.3 | 110 | 20 |
| Ceramides | Cer | IS-4 | Cer (d18:1/12:0) | 10.96 | 482.5→264.3 | 130 | 25 |
| | | 19 | Cer (d14:1/22:0) | 14.64 | 566.5→208.2 | 130 | 25 |
| | | 20 | Cer (d18:1/2:0) | 9.04 | 342.3→264.3 | 130 | 25 |
| | | 21 | Cer (d18:1/14:2) | 11.06 | 506.5→264.3 | 130 | 25 |
| | | 22 | Cer (d18:1/14:1) | 11.15 | 508.5→264.3 | 130 | 25 |
| | | 23 | Cer (d18:1/14:0) | 11.85 | 510.5→264.3 | 130 | 25 |
| | | 24 | Cer (d18:1/15:0) | 12.33 | 524.5→264.3 | 130 | 25 |
| | | 25 | Cer (d18:1/16:2) | 11.84 | 534.5→264.3 | 130 | 25 |
| | | 26 | Cer (d18:1/16:1) | 12.43 | 536.5→264.3 | 130 | 25 |
| | | 27 | Cer (d18:1/16:0) | 12.92 | 538.5→264.3 | 130 | 25 |
| | | 28 | Cer (d18:1/17:1) | 13.03 | 550.5→264.3 | 130 | 25 |
| | | 29 | Cer (d18:1/18:2) | 13.45 | 562.5→264.3 | 130 | 25 |
| | | 30 | Cer (d18:1/18:1) | 13.57 | 564.5→264.3 | 130 | 25 |
| | | 31 | Cer (d18:1/18:0) | 14.36 | 566.5→264.3 | 130 | 25 |
| | | 32 | Cer (d18:1/20:1) | 15.86 | 592.6→264.3 | 130 | 25 |
| | | 33 | Cer (d18:1/22:0) | 18.20 | 622.6→264.3 | 130 | 25 |
| | | 34 | Cer (d18:1/23:0) | 19.10 | 636.6→264.3 | 130 | 25 |
| | | 35 | Cer (d18:1/24:0) | 20.10 | 650.6→264.3 | 130 | 25 |
| | | 36 | Cer (d18:1/25:0) | 19.25 | 664.7→264.3 | 130 | 25 |
| | | 37 | Cer (d18:1/26:1) | 19.23 | 676.7→264.3 | 130 | 25 |
| | | 38 | Cer (d18:2/15:0) | 11.83 | 522.5→262.3 | 130 | 25 |
| | | 39 | Cer (d18:2/16:1) | 11.85 | 534.5→262.3 | 130 | 25 |
| | | 40 | Cer (d18:2/16:0) | 12.38 | 536.5→262.3 | 130 | 25 |
| | | 41 | Cer (d18:2/18:1) | 13.50 | 562.5→262.3 | 130 | 25 |
| | | 42 | Cer (d18:2/23:0) | 18.18 | 634.6→262.3 | 130 | 25 |
| | | 43 | Cer (d18:2/24:0) | 19.06 | 648.6→262.3 | 130 | 25 |
| | | 44 | Cer (d19:2/16:0) | 12.76 | 550.5→276.3 | 130 | 25 |
| | | 45 | Cer (d18:1/16:1(OH)) | 12.32 | 552.5→264.3 | 130 | 25 |
| | | 46 | Cer (d18:1/16:0(OH)) | 12.40 | 554.5→264.3 | 130 | 25 |
| | | 47 | Cer (d18:1/17:1(OH)) | 15.36 | 566.5→264.3 | 130 | 25 |
| | | 48 | Cer (d18:1/18:1(OH)) | 14.53 | 580.5→264.3 | 130 | 25 |
| | | 49 | Cer (d18:1/18:0(OH)) | 13.55 | 582.5→264.3 | 130 | 25 |
| | | 50 | Cer (d18:1/19:1(OH)) | 12.55 | 594.5→264.3 | 130 | 25 |
| | | 51 | Cer (d18:1/22:0(OH)) | 17.11 | 638.6→264.3 | 130 | 25 |
| | | 52 | Cer (d18:2/16:0(OH)) | 11.84 | 552.5→262.3 | 130 | 25 |
| | | 53 | Cer (d18:2/18:1(OH)) | 11.52 | 578.5→262.3 | 130 | 25 |
| | | 54 | Cer (d19:2/16:0(OH)) | 12.20 | 566.5→276.3 | 130 | 25 |
| | | 55 | Cer (d18:0/15:0) | 12.75 | 526.5→266.3 | 130 | 25 |
| | | 56 | Cer (d18:0/16:1) | 13.23 | 538.5→266.3 | 130 | 25 |
| | | 57 | Cer (d18:0/16:0) | 13.35 | 540.5→266.3 | 130 | 25 |
| | | 58 | Cer (d18:0/18:0) | 14.63 | 568.6→266.3 | 130 | 25 |
| | | 59 | Cer (d18:0/26:0) | 20.82 | 680.7→266.3 | 130 | 25 |
| | | 60 | Cer (t18:1/18:0) | 12.99 | 582.5→262.3 | 130 | 25 |
| | | 61 | Cer (t18:1/22:1) | 16.15 | 636.6→262.3 | 130 | 25 |
| | | 62 | Cer (t18:1/22:0) | 15.64 | 638.6→262.3 | 130 | 25 |
| | | 63 | Cer (t18:0/16:0) | 12.28 | 556.5→264.3 | 130 | 25 |
| | | 64 | Cer (t18:0/22:1) | 16.12 | 638.6→264.3 | 130 | 25 |
| | | 65 | Cer (t18:0/22:0) | 16.13 | 640.6→264.3 | 130 | 25 |
| | | 66 | Cer (t18:0/24:0) | 17.45 | 668.7→264.3 | 130 | 25 |
| | | 67 | Cer (t18:0/18:0(OH)) | 12.98 | 600.6→264.3 | 130 | 25 |
| | | 68 | Cer (t18:0/22:0(OH)) | 15.48 | 656.6→264.3 | 130 | 25 |
| | | 69 | Cer (t18:0/24:0(OH)) | 16.83 | 684.7→264.3 | 130 | 25 |
| Glycosphingolipids | HexCer | IS-5 | GlcCer (d18:1/12:0) | 10.40 | 644.5→264.3 | 130 | 30 |
| | | 70 | HexCer (d18:1/16:0) | 12.21 | 700.6→264.3 | 130 | 30 |
| | | 71 | HexCer (d18:2/16:0) | 11.52 | 698.6→262.3 | 130 | 30 |
| | | 72 | HexCer (d18:2/16:0(OH)) | 11.25 | 714.6→262.3 | 130 | 30 |
| | | 73 | HexCer (d19:2/15:0) | 11.46 | 698.6→276.3 | 130 | 30 |
| | | 74 | HexCer (d19:2/16:0(OH)) | 11.75 | 728.6→276.3 | 130 | 30 |
| | | 75 | HexCer (d19:2/17:0(OH)) | 12.00 | 742.6→276.3 | 130 | 30 |
| | | 76 | HexCer (d19:2/18:0(OH)) | 12.53 | 756.6→276.3 | 130 | 30 |
| | | 77 | HexCer (t19:1/16:1) | 11.20 | 728.6→276.3 | 130 | 30 |
| Phosphosphingolipids | SM | IS-6 | SM (d18:1/12:0) | 10.37 | 647.5→184.1 | 170 | 20 |
| | | 78 | SM (d18:1/14:0) | 11.1 | 675.5→184.1 | 170 | 20 |
| | | 79 | SM (d18:1/16:0) | 12 | 703.6→184.1 | 170 | 20 |
| | | 80 | SM (d18:1/18:0) | 13.25 | 731.6→184.1 | 170 | 20 |
| | | 81 | SM (d18:1/20:0) | 14.51 | 759.6→184.1 | 170 | 20 |
| | | 82 | SM (d18:1/22:0) | 15.61 | 787.7→184.1 | 170 | 20 |
| | | 83 | SM (d18:1/24:0) | 16.91 | 815.7→184.1 | 170 | 20 |

TABLE 6-continued

MRM parameters and validation data for the quantitation of 101 SPLs in wild-type *Cordyceps* and *Cordyceps* derivates

| | | | | | | |
|---|---|---|---|---|---|---|
| | | 84 | SM (d18:1/16:1) | 11.66 | 701.6→184.1 | 170 | 20 |
| | | 85 | SM (d18:1/20:1) | 13.9 | 757.6→184.1 | 170 | 20 |
| | | 86 | SM (d18:1/22:1) | 15.12 | 785.7→184.1 | 170 | 20 |
| | | 87 | SM (d18:2/18:0) | 12.75 | 729.6→184.1 | 170 | 20 |
| | | 88 | SM (d18:2/18:1) | 11.81 | 727.6→184.1 | 170 | 20 |
| | | 89 | SM (d18:1/18:1(OH)) | 12.38 | 745.6→184.1 | 170 | 20 |
| | | 90 | SM (d18:2/16:0(OH)) | 11.07 | 717.6→184.1 | 170 | 20 |
| | | 91 | SM (d33:1) | 11.56 | 689.6→184.1 | 170 | 20 |
| | | 92 | SM (d39:2) | 14.56 | 771.6→184.1 | 170 | 20 |
| | | 93 | SM (d42:2) | 16.14 | 813.7→184.1 | 170 | 20 |
| | | 94 | SM (d34:0) | 12.5 | 705.6→184.1 | 170 | 20 |
| | | 95 | SM (d36:0) | 13.84 | 733.6→184.1 | 170 | 20 |
| | | 96 | SM (d38:0) | 14.9 | 761.7→184.1 | 170 | 20 |
| PI-Cer[#] | | 97 | PI-Cer (d18:0/16:0(OH)) | 10.90 | 798.5→538.5 | 170 | 30 |
| | | 98 | PI-Cer (t18:0/22:0(OH)) | 12.84 | 898.6→638.6 | 170 | 30 |
| | | 99 | PI-Cer (t18:0/24:0(OH)) | 13.95 | 926.7→666.6 | 170 | 30 |
| MIPC[#] | | 100 | MIPC (t18:0/22:0(OH)) | 12.60 | 1060.7→638.6 | 170 | 40 |
| | | 101 | MIPC (t18:0/24:0(OH)) | 13.68 | 1088.7→666.6 | 170 | 40 |

| | | | Precision and stability (RSD %)[£] | | | | |
|---|---|---|---|---|---|---|---|
| SPLs | Subgroup | Internal No. | Injection precision | Intra-day precision | Inter-day precision | Analyte's stability | System's stability |
| Sphingoid bases | So | IS-1 | 1.17 | 1.25 | 2.02 | 2.04 | 2.88 |
| | | 1 | ND[$] | ND | ND | ND | 2.51 |
| | | 2 | 0.74 | 2.85 | 2.18 | 2.50 | 2.43 |
| | | 3 | ND | ND | ND | ND | 4.68 |
| | | 4 | ND | ND | ND | ND | 3.69 |
| | | 5 | 0.98 | 5.08 | 6.59 | 3.97 | 2.45 |
| | | 6 | 0.41 | 1.85 | 2.10 | 1.90 | 2.99 |
| | | 7 | 0.55 | 1.16 | 1.09 | 2.69 | 2.30 |
| | | 8 | 0.52 | 1.19 | 1.43 | 4.40 | 2.35 |
| | | 9 | 0.35 | 1.80 | 1.86 | 2.09 | 6.36 |
| | | 10 | 1.15 | 12.19 | 14.89 | 1.57 | 3.37 |
| | S1P | IS-2 | 0.30 | 0.94 | 1.74 | 4.79 | 5.40 |
| | | 11 | 1.02 | 4.67 | 2.43 | 2.54 | 5.76 |
| | S1Po[#] | 12 | ND | ND | ND | ND | 5.83 |
| | Sa | IS-3 | 0.49 | 2.15 | 2.19 | 1.37 | 4.34 |
| | | 13 | ND | ND | ND | ND | 4.51 |
| | | 14 | ND | ND | ND | ND | 3.72 |
| | | 15 | ND | ND | ND | ND | 3.31 |
| | | 16 | 0.63 | 2.58 | 3.41 | 4.02 | 3.88 |
| | | 17 | 1.03 | 0.57 | 0.61 | 0.83 | 4.48 |
| | | 18 | 0.58 | 2.43 | 2.06 | 6.09 | 3.11 |
| Ceramides | Cer | IS-4 | 1.88 | 3.92 | 4.03 | 3.57 | 5.41 |
| | | 19 | 1.32 | 3.48 | 3.47 | 11.06 | 12.46 |
| | | 20 | 5.60 | 12.69 | 11.98 | 4.50 | 4.86 |
| | | 21 | 0.53 | 3.79 | 3.89 | 4.72 | 10.21 |
| | | 22 | 2.99 | 7.11 | 9.99 | 16.17 | 5.95 |
| | | 23 | 2.17 | 4.63 | 4.19 | 18.05 | 10.86 |
| | | 24 | 0.50 | 1.55 | 1.36 | 9.58 | 14.48 |
| | | 25 | 2.43 | 3.31 | 3.83 | 12.62 | 10.23 |
| | | 26 | 0.54 | 1.26 | 3.14 | 4.72 | 9.47 |
| | | 27 | 1.50 | 2.80 | 6.05 | 9.14 | 11.30 |
| | | 28 | 1.78 | 4.85 | 4.33 | 15.91 | 13.69 |
| | | 29 | 1.12 | 5.98 | 6.29 | 7.52 | 14.02 |
| | | 30 | 0.78 | 0.95 | 1.20 | 4.06 | 9.26 |
| | | 31 | 1.72 | 3.04 | 4.54 | 8.21 | 12.44 |
| | | 32 | 1.01 | 8.45 | 7.15 | 6.96 | 20.58 |
| | | 33 | 4.88 | 10.12 | 8.26 | 17.27 | 19.05 |
| | | 34 | 2.82 | 4.01 | 7.49 | 5.38 | 14.47 |
| | | 35 | 4.22 | 4.78 | 4.05 | 3.73 | 13.24 |
| | | 36 | ND | ND | ND | ND | 14.40 |
| | | 37 | 5.08 | 2.38 | 2.94 | 7.04 | 14.17 |
| | | 38 | 2.53 | 4.35 | 6.87 | 14.73 | 11.54 |
| | | 39 | 0.73 | 6.26 | 3.63 | 7.28 | 2.68 |
| | | 40 | 0.39 | 1.49 | 1.17 | 3.74 | 11.23 |
| | | 41 | ND | ND | ND | ND | 10.07 |
| | | 42 | ND | ND | ND | ND | 21.35 |
| | | 43 | 4.01 | 4.34 | 5.62 | 5.10 | 13.95 |
| | | 44 | 1.04 | 1.50 | 2.49 | 5.83 | 10.33 |
| | | 45 | 3.06 | 4.12 | 4.46 | 9.65 | 14.78 |
| | | 46 | 1.34 | 0.73 | 0.71 | 6.06 | 11.96 |
| | | 47 | 2.36 | 2.68 | 3.95 | 6.35 | 14.16 |
| | | 48 | 0.31 | 2.22 | 3.70 | 4.98 | 14.72 |
| | | 49 | ND | ND | ND | ND | 8.01 |
| | | 50 | 1.66 | 2.36 | 2.18 | 7.49 | 12.06 |

TABLE 6-continued

MRM parameters and validation data for the quantitation of 101 SPLs in wild-type *Cordyceps* and *Cordyceps* derivates

| | | | | | | | |
|---|---|---|---|---|---|---|---|
| | | | 51 | 2.40 | 6.06 | 10.11 | 19.27 | 19.71 |
| | | | 52 | 2.88 | 5.74 | 14.77 | 19.71 | 13.98 |
| | | | 53 | ND | ND | ND | ND | 12.92 |
| | | | 54 | 0.35 | 3.57 | 5.49 | 2.41 | 6.30 |
| | | | 55 | 1.03 | 7.52 | 7.17 | 15.16 | 12.59 |
| | | | 56 | 2.35 | 5.60 | 4.32 | 10.49 | 9.24 |
| | | | 57 | 1.77 | 5.60 | 4.49 | 11.40 | 9.75 |
| | | | 58 | ND | ND | ND | ND | 14.79 |
| | | | 59 | ND | ND | ND | ND | 14.20 |
| | | | 60 | ND | ND | ND | ND | 14.17 |
| | | | 61 | ND | ND | ND | ND | 14.48 |
| | | | 62 | 5.95 | 22.80 | 21.75 | 17.75 | 18.08 |
| | | | 63 | 1.02 | 3.71 | 4.67 | 9.28 | 10.46 |
| | | | 64 | ND | ND | ND | ND | 21.05 |
| | | | 65 | 0.43 | 9.40 | 8.70 | 7.21 | 14.36 |
| | | | 66 | 1.76 | 2.15 | 2.66 | 4.83 | 21.36 |
| | | | 67 | 2.68 | 4.36 | 4.53 | 11.48 | 12.06 |
| | | | 68 | 1.17 | 3.70 | 2.89 | 5.04 | 14.51 |
| | | | 69 | 2.32 | 2.59 | 2.43 | 18.20 | 22.32 |
| Glycosphingolipids | HexCer | | IS-5 | 1.99 | 1.09 | 1.04 | 4.79 | 5.89 |
| | | | 70 | 1.53 | 6.73 | 9.43 | 7.96 | 14.79 |
| | | | 71 | 1.20 | 2.91 | 2.01 | 4.81 | 4.81 |
| | | | 72 | 2.15 | 6.51 | 7.11 | 5.81 | 14.71 |
| | | | 73 | 1.93 | 6.63 | 5.60 | 5.33 | 6.50 |
| | | | 74 | 0.50 | 11.97 | 15.09 | 4.32 | 8.65 |
| | | | 75 | 5.44 | 2.33 | 2.42 | 23.88 | 20.74 |
| | | | 76 | 0.58 | 3.80 | 3.08 | 12.18 | 10.77 |
| | | | 77 | ND | ND | ND | ND | 10.09 |
| Phosphosphingolipids | SM | | IS-6 | 1.87 | 2.02 | 1.72 | 5.38 | 5.40 |
| | | | 78 | 0.39 | 2.83 | 3.51 | 2.44 | 3.63 |
| | | | 79 | 0.52 | 1.33 | 2.18 | 2.3 | 4.9 |
| | | | 80 | 0.83 | 1.94 | 2.06 | 3.6 | 4.99 |
| | | | 81 | 1.06 | 5.48 | 4.76 | 5.08 | 10.22 |
| | | | 82 | 5.52 | 4.99 | 4.81 | 2.1 | 11.33 |
| | | | 83 | 2.12 | 3.65 | 2.42 | 2.09 | 14.39 |
| | | | 84 | 1.07 | 2.15 | 2.05 | 3.98 | 3.62 |
| | | | 85 | 1.75 | 2.8 | 3.48 | 3.14 | 9.43 |
| | | | 86 | 0.47 | 4.6 | 6.32 | 4.76 | 7.39 |
| | | | 87 | 1.4 | 6.59 | 6.9 | 7.41 | 5.37 |
| | | | 88 | ND | ND | ND | ND | 7.42 |
| | | | 89 | 1.35 | 2.82 | 3.91 | 5.21 | 7.03 |
| | | | 90 | 1.43 | 1.33 | 0.86 | 4.21 | 4.13 |
| | | | 91 | 2.79 | 5.38 | 4.6 | 2.57 | 7.44 |
| | | | 92 | 2.68 | 5.07 | 4.16 | 4.51 | 11.93 |
| | | | 93 | 1.65 | 2.82 | 2.77 | 1.49 | 10.5 |
| | | | 94 | 1.29 | 5.33 | 3.96 | 6.85 | 6.14 |
| | | | 95 | 1.91 | 3.23 | 3.04 | 5.74 | 7.85 |
| | | | 96 | ND | ND | ND | ND | 11.75 |
| | PI-Cer[#] | | 97 | ND | ND | ND | ND | 5.50 |
| | | | 98 | ND | ND | ND | ND | 14.83 |
| | | | 99 | 1.73 | 5.26 | 4.66 | 12.65 | 13.32 |
| | MIPC[#] | | 100 | ND | ND | ND | ND | 20.32 |
| | | | 101 | 2.37 | 19.15 | 23.55 | 20.13 | 11.82 |

*CE, Collision Energy.
[£]Precisions and stabilities of endogenous SPLs in validation samples (*Hirsutella sinensis*) were calculated according to the quantitative data, while precisions and stabilities of 6 IS were calculated using peak area data; system's stability was determined using QC sample.
$ND, Not detected in validation samples.
[#]The IS for quantitation of S1Po was IS-2; the IS for quantitation of PI-Cer and MIPC was IS-4.

TABLE 7

Identification of SPLs in wild-type *Cordyceps* and *Cordyceps* derivates being related to wild-type *Cordyceps* by using UHPLC-QTOF-MS/MS

| Internal No. | Name of SPL | Formula | [M + H]+ (m/z) | Diff (ppm) | Score | RT (min) | ms/ms fragments (m/z) |
|---|---|---|---|---|---|---|---|
| IS-1 | So (d17:1) | C17H35NO2 | 286.2740 | 0.06 | 99.70 | 6.37 | 268.2627, 250.2545 |
| 1 | So (d14:2) | C14H27NO2 | 242.2111 | −0.82 | 83.88 | 3.76 | 224.1996, 206.1895, 194.1887, 60.0440 |
| 2 | So (d14:1) | C14H29NO2 | 244.2270 | −1.34 | 81.57 | 5.30 | 226.1296, 60.0436 |
| 3 | So (d16:1) | C16H33NO2 | 272.2578 | −2.50 | 91.98 | 5.95 | 254.2414, 236.2334, 60.0443 |
| 4 | So (d17:2) | C17H33NO2 | 284.2583 | 1.30 | 49.53 | 7.11 | 266.2485 |
| 5 | So (d18:2) | C18H35NO2 | 298.2742 | −3.82 | 83.03 | 9.10 | 280.2652, 60.0448 |
| 6 | So (d18:1) | C18H37NO2 | 300.2898 | −0.05 | 99.57 | 8.07 | 282.2774, 264.2371, 60.0450 |
| 7 | So (t18:1) | C18H37NO3 | 316.2850 | −1.38 | 82.52 | 6.38 | 298.2727, 280.2623, 262.2517, 250.2525, 60.0446 |
| 8 | So (t18:1) isomer | C18H37NO3 | 316.2847 | −0.28 | 81.81 | 6.90 | 298.2746, 60.0444 |
| 9 | So (d20:1) | C20H41NO2 | 328.3213 | 0.64 | 98.97 | 9.41 | 310.3100 |

TABLE 7-continued

Identification of SPLs in wild-type *Cordyceps* and *Cordyceps* derivates being related to wild-type *Cordyceps* by using UHPLC-QTOF-MS/MS

| Internal No. | Name of SPL | Formula | [M + H]+ (m/z) | Diff (ppm) | Score | RT (min) | ms/ms fragments (m/z) |
|---|---|---|---|---|---|---|---|
| 10 | So (t22:2) | C22H43NO3 | 370.3316 | −0.35 | 98.90 | 7.49 | 352.3225 |
| IS-2 | S1P (d17:1) | C17H36NO5P | 366.2406 | −0.56 | 99.74 | 6.55 | 250.2536 |
| 11 | S1P (d18:1) | C18H38NO5P | 380.2564 | 1.20 | 82.71 | 9.03 | 362.3209, 264.2659 |
| 12 | S1Po (d18:1)* | C23H49N2O5P | 467.3597 | −5.08 | 74.93 | 6.55 | 449.3489, 184.0734 |
| IS-3 | Sa (d17:0) | C17H37NO2 | 288.2898 | −0.09 | 99.29 | 6.57 | 270.2781, 252.2673, 240.2680, 60.0442 |
| 13 | Sa (d16:0) | C16H35NO2 | 274.2740 | −0.68 | 95.38 | 6.24 | 256.2617, 238.2522, 60.0443 |
| 14 | Sa (m18:0) | C18H39NO | 286.3105 | 0.19 | 98.89 | 7.12 | 268.2989 |
| 15 | Sa (d17:0) isomer* | C17H37NO2 | 288.2889 | −3.54 | 95.85 | 5.51 | 270.2784 |
| 16 | Sa (d18:0) | C18H39NO2 | 302.3048 | −1.81 | 46.59 | 6.91 | 284.2926, 266.2819, 254.2842, 60.0439 |
| 17 | Sa (t18:0) | C18H39NO3 | 318.3026 | 7.56 | 84.09 | 6.61 | 300.2883, 282.2782, 264.2683, 270.2782, 252.2670, 60.0442 |
| 18 | Sa (t18:0) isomer | C18H39NO3 | 318.3004 | −0.40 | 99.04 | 6.32 | 300.2888, 288.2772, 270.2790 |
| IS-4 | Cer (d18:1/12:0) | C30H59NO3 | 482.4565 | −1.59 | 92.99 | 10.96 | 464.4431, 446.4281, 434.4308, 282.2786, 264.2678, 252.2671 |
| 19 | Cer (d14:1/22:0) | C36H71NO3 | 566.5468 | −6.53 | 55.89 | 14.64 | 548.5263, 530.5278, 518.5263, 226.2156, 208.2054, 196.2049, 60.0442 |
| 20 | Cer (d18:1/2:0)* | C20H39NO3 | 342.3000 | 1.50 | 91.72 | 9.04 | 264.2606 |
| 21 | Cer (d18:1/14:2) | C32H59NO3 | 506.4574 | 0.06 | 93.77 | 11.06 | 282.2837, 264.2675, 60.0617 |
| 22 | Cer (d18:1/14:1) | C32H61NO3 | 508.4715 | −1.59 | 96.56 | 11.15 | 264.2723 |
| 23 | Cer (d18:1/14:0) | C32H63NO3 | 510.4878 | −1.20 | 96.55 | 11.85 | 492.4738, 474.4603, 462.4662, 282.2777, 264.2673, 252.2662, 60.0435 |
| 24 | Cer (d18:1/15:0) | C33H65NO3 | 524.5042 | 0.39 | 97.66 | 12.33 | 506.4927, 488.4815, 282.2796, 264.2687, 252.2678, 60.0444 |
| 25 | Cer (d18:1/16:2) | C34H63NO3 | 534.4880 | 0.38 | 97.77 | 11.84 | 282.2789, 264.2685, 252.2686 |
| 26 | Cer (d18:1/16:1) | C34H65NO3 | 536.5042 | 0.36 | 94.85 | 12.43 | 518.493, 506.4931, 488.4800, 282.2795, 264.2691, 252.2691, 60.0447 |
| 27 | Cer (d18:1/16:0) | C34H67NO3 | 538.5204 | 1.72 | 98.10 | 12.92 | 520.4758, 502.4667, 282.2624, 264.2530, 252.2530, 60.0412 |
| 28 | Cer (d18:1/17:1) | C35H67NO3 | 550.5185 | −0.65 | 98.47 | 13.03 | 300.2898, 282.2742, 264.2661, 60.0437 |
| 29 | Cer (d18:1/18:2) | C36H67NO3 | 562.5183 | −1.90 | 97.30 | 13.45 | 544.5042, 300.2883, 282.2783, 264.2674, 252.2687, 60.0446 |
| 30 | Cer (d18:1/18:1) | C36H69NO3 | 564.5353 | 0.50 | 99.81 | 13.57 | 548.5343, 530.4838, 300.2836, 282.2760, 264.2643, 252.2700, 60.0442 |
| 31 | Cer (d18:1/18:0) | C36H71NO3 | 566.5486 | −2.80 | 67.90 | 14.36 | 548.5343, 518.5343, 282.2788, 264.2708, 252.2720, 60.0450 |
| 32 | Cer (d18:1/20:1) | C38H73NO4 | 592.5713 | 7.76 | 73.80 | 15.86 | 556.5546, 282.2793, 264.2689, 252.2685, 60.0443 |
| 33 | Cer (d18:1/22:0) | C40H79NO3 | 622.6127 | −1.42 | 96.67 | 18.20 | 604.5998, 586.5841, 300.2889, 282.2779, 264.2680, 252.2672, 60.0441 |
| 34 | Cer (d18:1/23:0)* | C41H81NO3 | 636.6274 | −2.36 | 94.37 | 19.10 | 618.6192, 600.6006, 300.2886, 282.2778, 264.2695, 252.2668, 60.0441 |
| 35 | Cer (d18:1/24:0)* | C42H83NO3 | 650.6433 | −2.38 | 94.72 | 20.10 | 632.6333, 614.6204, 300.2887, 282.2806, 264.2690, 252.2727, 60.0441 |
| 36 | Cer (d18:1/25:0) | C43H85NO3 | 664.6585 | −3.59 | 74.25 | 19.25 | 300.2901, 282.2772, 264.2687, 252.2648, 60.0434 |
| 37 | Cer (d18:1/26:1) | C44H85NO3 | 676.6589 | −2.30 | 72.91 | 19.23 | 300.2924, 282.2786, 264.2682, 252.2685, 60.0435 |
| 38 | Cer (d18:2/15:0) | C33H63NO3 | 522.4881 | −0.99 | 96.90 | 11.83 | 504.4757, 486.4644, 474.4622, 280.2621, 262.2525, 250.2525, 60.0437 |
| 39 | Cer (d18:2/16:1) | C34H63NO3 | 534.4887 | 1.13 | 46.93 | 11.85 | 516.4747, 280.2627, 262.2520, 250.2527, 60.0448 |
| 40 | Cer (d18:2/16:0) | C34H65NO3 | 536.5047 | 1.63 | 98.33 | 12.38 | 518.5032, 500.4807, 488.4866, 280.2630, 262.2528, 250.2523, 60.0446 |
| 41 | Cer (d18:2/18:1) | C36H67NO3 | 562.5183 | −1.90 | 97.30 | 13.50 | 544.5027, 298.2732, 280.2608, 262.2517, 60.0443 |
| 42 | Cer (d18:2/23:0) | C41H79NO3 | 634.6120 | −2.61 | 90.40 | 18.18 | 616.6017, 598.6093, 298.2733, 280.2624, 262.2523, 250.2508, 60.0446 |
| 43 | Cer (d18:2/24:0)* | C42H81NO3 | 648.6282 | −1.20 | 96.21 | 19.06 | 630.6151, 612.5993, 298.2729, 280.2626, 262.2522, 250.2522, 60.0443 |
| 44 | Cer (d19:2/16:0) | C35H67NO3 | 550.5180 | −2.66 | 95.77 | 12.76 | 532.5053, 514.4940, 502.4963, 294.2781, 276.2676, 264.2679, 60.0441 |
| 45 | Cer (d18:1/16:1(OH)) | C34H65NO4 | 552.4987 | 0.18 | 93.34 | 12.32 | 534.4662, 516.4655, 282.2793, 264.2690, 252.2664, 60.0434 |
| 46 | Cer (d18:1/16:0(OH)) | C34H67NO4 | 554.5137 | −1.09 | 98.26 | 12.40 | 536.4763, 518.4844, 500.4834, 318.2981, 300.2877, 282.2777, 264.2676, 252.2678, 60.0442 |
| 47 | Cer (d18:1/17:1(OH)) | C35H67NO4 | 566.5138 | −0.88 | 97.50 | 15.36 | 548.5389, 530.5290, 300.2885, 282.2786, 264.2678, 252.2676, 60.0442 |
| 48 | Cer (d18:1/18:1(OH)) | C36H69NO4 | 580.5215 | 1.79 | 89.58 | 14.53 | 562.5497, 532.3500, 282.2766, 264.2688, 252.2640, 60.0421 |
| 49 | Cer (d18:1/18:0(OH)) | C36H71NO4 | 582.5455 | 0.20 | 85.70 | 13.55 | 564.2850, 534.1585, 282.2682, 264.2682, 252.2677, 60.0442 |
| 50 | Cer (d18:1/19:1(OH)) | C37H71NO4 | 594.5424 | −4.67 | 81.99 | 12.55 | 282.2656, 264.2670, 252.2348, 60.0452 |
| 51 | Cer (d18:1/22:0(OH))* | C40H79NO4 | 638.6089 | 1.10 | 98.65 | 17.11 | 620.5936, 602.5772, 300.2884, 282.2769, 264.2676, 252.2644, 60.0443 |
| 52 | Cer (d18:2/16:0(OH)) | C34H65NO4 | 552.4991 | 0.91 | 84.54 | 11.84 | 534.4955, 516.4797, 298.2779, 280.2621, 262.2527, 250.2495, 60.0449 |
| 53 | Cer (d18:2/18:1(OH)) | C36H67NO4 | 578.5137 | −1.04 | 88.31 | 11.52 | 560.5017, 542.4887, 524.4798, 512.4791, 316.2824, 298.2728, 280.2623, 262.2518, 250.2508, 60.0441 |
| 54 | Cer (d19:2/16:0(OH)) | C35H67NO4 | 566.5167 | 3.22 | 90.99 | 12.20 | 566.5060, 548.5021, 530.4916, 294.2780, 276.2684, 264.2693, 60.0436 |
| 55 | Cer (d18:0/15:0)* | C33H67NO3 | 526.5185 | −1.58 | 49.26 | 12.75 | 508.5046, 490.4941, 284.2962, 266.2840, 254.2827, 60.0441 |
| 56 | Cer (d18:0/16:1) | C34H67NO3 | 538.5194 | 0.01 | 94.87 | 13.23 | 520.4573, 502.4465, 302.2804, 284.2702, 266.2606, 254.2210, 60.0398 |
| 57 | Cer (d18:0/16:0) | C34H69NO3 | 540.5350 | 0.02 | 47.62 | 13.35 | 522.5168, 504.5167, 302.3034, 284.2930, 266.2819, 254.2848, 60.0442 |
| 58 | Cer (d18:0/18:0) | C36H73NO3 | 568.5660 | −0.53 | 97.48 | 14.63 | 550.5549, 532.5356, 302.3041, 284.2927, 266.2838, 254.2854, 60.0439 |

TABLE 7-continued

Identification of SPLs in wild-type *Cordyceps* and *Cordyceps* derivates being related to wild-type *Cordyceps* by using UHPLC-QTOF-MS/MS

| Internal No. | Name of SPL | Formula | [M + H]+ (m/z) | Diff (ppm) | Score | RT (min) | ms/ms fragments (m/z) |
|---|---|---|---|---|---|---|---|
| 59 | Cer (d18:0/26:0)* | C44H89NO3 | 680.6932 | 2.63 | 95.31 | 20.82 | 662.6779, 644.6688, 302.3044, 284.2943, 266.2837, 254.2835, 60.0443 |
| 60 | Cer (t18:1/18:0) | C36H71NO4 | 582.5454 | −2.78 | 87.05 | 12.99 | 564.5238, 546.5252, 280.2609, 262.2535, 250.2525, 60.044 |
| 61 | Cer (t18:1/22:1)* | C40H77NO4 | 636.5916 | −1.41 | 97.00 | 16.15 | 618.5775, 600.5669, 316.2958, 298.2726, 280.2620, 262.2527, 250.2512, 60.0442 |
| 62 | Cer (t18:1/22:0) | C40H79NO4 | 638.6075 | −1.72 | 95.50 | 15.64 | 620.5942, 602.5830, 584.5657, 316.2827, 298.2730, 280.2626, 262.2522, 250.2507, 60.0443 |
| 63 | Cer (t18:0/16:0) | C34H69NO4 | 556.5283 | −3.49 | 47.41 | 12.28 | 282.2782, 264.2673, 252.2681, 60.0443 |
| 64 | Cer (t18:0/22:1) | C40H79NO4 | 638.6066 | −2.51 | 92.94 | 16.12 | 620.5912, 602.5785, 318.2885, 282.2785, 264.2677, 252.2681, 60.0443 |
| 65 | Cer (t18:0/22:0) | C40H81NO4 | 640.6224 | −2.61 | 95.18 | 16.13 | 622.6117, 604.6000, 318.3000, 300.2895, 282.2789, 264.2680, 252.2677, 60.0445 |
| 66 | Cer (t18:0/24:0) | C42H85NO4 | 668.6558 | 1.30 | 98.39 | 17.45 | 650.6451, 632.6331, 614.6217, 318.3005, 300.2900, 282.2792, 264.2687, 252.2685, 60.0446 |
| 67 | Cer (t18:0/18:0(OH)) | C36H73NO5 | 600.5558 | −1.30 | 96.81 | 12.98 | 582.5451, 564.5357, 546.5223, 534.5204, 318.3015, 300.2895, 282.2799, 264.2693, 252.2686, 60.045 |
| 68 | Cer (t1 8:0/22:0(OH)) | C40H81NO5 | 656.6183 | −1.13 | 97.91 | 15.48 | 638.6032, 620.5948, 602.5856, 318.2980, 300.2891, 282.2780, 264.2676, 252.2673, 60.0441 |
| 69 | Cer (t18:0/24:0(OH)) | C42H85NO5 | 684.6709 | 3.48 | 52.12 | 16.83 | 666.6481, 648.6362, 630.6249, 612.6156, 318.3042, 300.2934, 282.2830, 264.2720, 252.2713, 60.0454 |
| IS-5 | GlcCer (d18:1/12:0) | C36H69NO8 | 644.5116 | −0.11 | 99.98 | 10.40 | 264.2684, 60.0441 |
| 70 | HexCer (d18:1/16:0)* | C40H77NO8 | 700.5704 | −2.69 | 93.97 | 12.21 | 682.5608, 664.5436, 520.5076, 502.4982, 490.4893, 282.2788, 264.2683, 252.2698, 60.0445 |
| 71 | HexCer (d18:2/16:0) | C40H75NO8 | 698.5573 | 1.27 | 86.87 | 11.52 | 680.5461, 536.5047, 518.4944, 500.4838, 280.2669, 262.2535, 250.2535 |
| 72 | HexCer (d18:2/16:0(OH)) | C40H75NO9 | 714.5522 | 0.55 | 97.12 | 11.25 | 696.5392, 534.4879, 516.4774, 504.477, 280.2636, 262.2532, 252.2534, 60.0455 |
| 73 | HexCer (d19:2/15:0) | C40H75NO8 | 698.5555 | −1.43 | 94.75 | 11.46 | 680.4951, 662.6058, 536.4120, 518.4675, 294.2805, 276.2660, 264.2522, 60.0440 |
| 74 | HexCer (d19:2/16:0(OH)) | C41H77NO9 | 728.5679 | 1.05 | 86.31 | 11.75 | 710.5562, 692.5422, 566.5138, 548.5038, 530.4929, 518.4936, 294.2794, 276.2691, 264.2694, 60.0447 |
| 75 | HexCer (d19:2/17:0(OH))* | C42H79NO9 | 742.5842 | 1.87 | 94.85 | 12.00 | 724.5716, 562.5191, 544.5080, 532.5108, 294.2787, 276.2696, 60.0451 |
| 76 | HexCer (d19:2/18:0(OH)) | C43H81NO9 | 756.5992 | 0.21 | 96.54 | 12.53 | 738.5863, 576.5335, 558.5236, 546.5249, 294.2788, 276.2689, 264.2686, 60.0447 |
| 77 | HexCer (t19:1/16:1) | C41H77NO9 | 728.5678 | 0.82 | 98.38 | 11.20 | 710.5435, 692.5330, 548.4912, 530.4811, 512.4701, 330.2718, 312.2484, 294.2775, 276.2677, 60.0441 |
| IS-6 | SM (d18:1/12:0) | C35H71N2O6P | 647.5119 | 2.88 | 89.65 | 10.37 | 282.2788, 264.2672, 184.0742 |
| 78 | SM (d18:1/14:0) | C37H75N2O6P | 675.5435 | −0.31 | 99.53 | 11.10 | 264.2628, 184.0733 |
| 79 | SM (d18:1/16:0) | C39H79N2O6P | 703.5773 | 3.43 | 87.95 | 12.00 | 264.2723, 184.0738 |
| 80 | SM (d18:1/18:0) | C41H83N2O6P | 731.6061 | 0.01 | 99.51 | 13.25 | 264.2670, 184.0732 |
| 81 | SM (d18:1/20:0) | C43H87N2O6P | 759.6377 | 0.06 | 99.42 | 14.51 | 264.2675, 184.0731 |
| 82 | SM (d18:1/22:0) | C45H91N2O6P | 787.6679 | −1.82 | 93.87 | 15.61 | 264.2642, 184.074 |
| 83 | SM (d18:1/24:0) | C47H95N2O6P | 815.6937 | −7.51 | 66.52 | 16.91 | 264.2616, 184.0717 |
| 84 | SM (d18:1/16:1) | C39H77N2O6P | 701.5586 | −0.56 | 99.03 | 11.66 | 264.2670, 184.0733 |
| 85 | SM (d18:1/20:1) | C43H85N2O6P | 757.6234 | 2.11 | 95.74 | 13.90 | 264.2676, 184.0726 |
| 86 | SM (d18:1/22:1) | C45H89N2O6P | 785.6519 | −2.62 | 85.23 | 15.12 | 264.2686, 184.0741 |
| 87 | SM (d18:2/18:0) | C41H81N2O6P | 729.5895 | −2.38 | 81.30 | 12.75 | 262.2550, 184.0738 |
| 88 | SM (d18:2/18:1) | C41H79N2O6P | 727.5733 | −3.23 | 89.12 | 11.81 | 262.2520, 184.0729 |
| 89 | SM (d18:1/18:1(OH)) | C41H81N2O7P | 745.5853 | −0.49 | 94.97 | 12.38 | 264.2709, 184.0737 |
| 90 | SM (d18:2/16:0(OH)) | C39H77N2O7P | 717.5546 | 0.34 | 70.39 | 11.07 | 262.2531, 184.0738 |
| 91 | SM (d33:1) | C38H77N2O6P | 689.5578 | −1.61 | 93.11 | 11.56 | 184.0728 |
| 92 | SM (d39:2) | C44H87N2O6P | 771.6349 | −4.65 | 72.19 | 14.56 | 184.0726 |
| 93 | SM (d42:2) | C47H93N2O6P | 813.6809 | −5.03 | 78.04 | 16.14 | 184.0734 |
| 94 | SM (d34:0) | C39H81N2O6P | 705.5906 | 0.19 | 99.72 | 12.50 | 184.0732 |
| 95 | SM (d36:0) | C41H85N2O6P | 733.6209 | −1.32 | 96.37 | 13.84 | 184.0734 |
| 96 | SM (d38:0) | C43H89N2O6P | 761.6523 | −1.98 | 91.96 | 14.90 | 184.0728 |
| 97 | PI-Cer (d18:0/16:0(OH))* | C40H80NO12P | 798.5494 | 0.38 | 91.30 | 10.90 | 780.5319, 556.5266, 538.5169, 520.5078, 284.2930, 266.2852, 60.0425 |
| 98 | PI-Cer (t18:0/22:0(OH)) | C46H92NO13P | 898.6364 | −1.67 | 96.77 | 12.84 | 880.6528, 666.6358, 638.6056, 620.5907, 602.4465, 300.2888, 282.2773, 264.2655, 252.2662, 60.0443 |
| 99 | PI-Cer (t18:0/24:0(OH)) | C48H96NO13P | 926.6692 | 0.01 | 98.13 | 13.95 | 908.6490, 684.6483, 666.6362, 648.6261, 630.6105, 300.2882, 282.2777, 264.2674, 252.2677, 60.0442 |
| 100 | MIPC (t18:0/22:0(OH)) | C52H102NO18P | 1060.6880 | −2.55 | 91.03 | 12.60 | 1042.5295, 898.6364, 880.6253, 656.6104, 638.6042, 300.2909, 282.2738, 264.2668, 60.0447 |
| 101 | MIPC (t18:0/24:0(OH)) | C54H106NO18P | 1088.7205 | −1.36 | 95.15 | 13.68 | 926.9604, 666.6345, 648.6163, 300.2877, 282.2777, 264.2664, 60.0445 |

*Sphingolipids were identified from *Cordyceps* derivates only.

TABLE 8

Calibration equations, correlation coefficients ($r^2$), linear ranges, limit of detection (LOD), limit of quantitation (LOQ) and recovery of IS

| IS | Calibration equations | $r^2$ | Linear range (nM) | LOD (nM) | LOQ (nM) | Low[#] (n = 6) Recovery (%) | RSD (%) | Medium[&] (n = 6) Recovery (%) | RSD (%) | High[*] (n = 6) Recovery (%) | RSD (%) | Mean Recovery (%) |
|---|---|---|---|---|---|---|---|---|---|---|---|---|
| IS-1 | Y = 443.61X − 1920.10 | 0.9992 | 3.34-3340.00 | 0.025 | 0.835 | 96.72 | 3.50 | 83.13 | 1.83 | 81.31 | 2.37 | 87.05 |
| IS-2 | Y = 86.64X − 960.46 | 0.9977 | 8.35-3340.00 | 1.670 | 6.680 | 90.23 | 3.56 | 89.33 | 1.28 | 71.59 | 1.61 | 83.72 |
| IS-3 | Y = 92.01X − 1303.30 | 0.9977 | 16.70-3340.00 | 3.340 | 16.700 | 88.98 | 4.81 | 75.43 | 2.30 | 80.69 | 1.27 | 81.70 |
| IS-4 | Y = 413.61X − 12809.00 | 0.9988 | 8.35-3340.00 | 0.025 | 1.670 | 104.12 | 3.07 | 101.40 | 4.46 | 94.94 | 1.39 | 100.15 |
| IS-5 | Y = 1171.30X + 12114.00 | 0.9994 | 3.34-3340.00 | 0.005 | 0.017 | 100.65 | 2.99 | 97.01 | 2.10 | 100.60 | 1.62 | 99.42 |
| IS-6 | Y = 74.38X − 2785.00 | 0.9983 | 8.35-3340.00 | 1.670 | 6.680 | 73.06 | 3.24 | 94.43 | 2.28 | 97.81 | 4.84 | 88.43 |

[#]Low, Low concentration;

[&]Medium, Medium concentration;

[*]High, High concentration

TABLE 9

Level of representative SPLs discriminating wild-type *Cordyceps* and *Cordyceps* derivates

| Group A V.S. Group B | SPLs | VIP | Group A | Group B | p |
|---|---|---|---|---|---|
| Wild-type *Cordyceps* V.S. *Hirsutella sinensis* | HexCer (t19:1/16:1) | 1.38 | 0.715 ± 0.120 | 4.416 ± 0.619 | 0.0000 |
| | HexCer (d19:2/16:0(OH)) | 1.37 | 0.958 ± 0.289 | 5.436 ± 0.638 | 0.0000 |
| | So (d18:1) | 1.35 | 0.493 ± 0.268 | 3.023 ± 0.423 | 0.0000 |
| Wild-type *Cordyceps* V.S. *Cordyceps sinensis* | Sa (d16:0) | 1.41 | 0.013 ± 0.013 | 12.732 ± 0.724 | 0.0000 |
| | HexCer (d19:2/16:0(OH)) | 1.40 | 0.958 ± 0.289 | 10.203 ± 1.147 | 0.0000 |
| | PI-Cer (d18:0/16:0(OH)) | 1.40 | 0 | 6.977 ± 1.505 | 0.0000 |
| Wild-type *Cordyceps* V.S. *Cephalosporium sinensis* | SM (d18:2/16:0(OH)) | 1.46 | 0.419 ± 0.058 | 0.017 ± 0.031 | 0.0000 |
| | Cer (d18:1/18:1) | 1.45 | 0.074 ± 0.069 | 12.008 ± 2.387 | 0.0000 |
| | Cer (d18:0/18:0) | 1.40 | 0.008 ± 0.006 | 9.885 ± 3.149 | 0.0000 |
| Wild-type *Cordyceps* V.S. *Mortierella* SP | Cer (d18:0/16:1) | 1.41 | 0.031 ± 0.025 | 0.616 ± 0.110 | 0.0000 |
| | SM (d18:2/18:0) | 1.40 | 10.426 ± 2.543 | 0.145 ± 0.051 | 0.0000 |
| | SM (d18:2/16:0(OH)) | 1.37 | 0.419 ± 0.058 | 0.054 ± 0.016 | 0.0000 |
| Wild-type *Cordyceps* V.S. *Gliocadium roseum* | Cer (d18:1/18:1) | 1.45 | 0.074 ± 0.069 | 13.455 ± 0.594 | 0.0000 |
| | Sa (d16:0) | 1.44 | 0.013 ± 0.013 | 0.211 ± 0.005 | 0.0000 |
| | Sa (m18:0) | 1.44 | 0.046 ± 0.011 | 0.283 ± 0.024 | 0.0002 |
| *Hirsutella sinensis* V.S. *Cordyceps sinensis* | Sa (d16:0) | 1.28 | 0.014 ± 0.006 | 12.732 ± 0.724 | 0.0000 |
| | So (t22:2) | 1.28 | 0.252 ± 0.071 | 10.170 ± 0.732 | 0.0000 |
| | So (d20:1) | 1.27 | 2.329 ± 0.583 | 12.913 ± 0.829 | 0.0000 |
| *Hirsutella sinensis* V.S. *Cephalosporium sinensis* | Cer (d18:1/16:1) | 1.42 | 12.510 ± 1.138 | 1.109 ± 0.309 | 0.0000 |
| | HexCer (d19:2/16:0(OH)) | 1.37 | 5.436 ± 0.638 | 0.547 ± 0.802 | 0.0000 |
| | Cer (d18:1/18:1) | 1.36 | 1.227 ± 0.845 | 12.008 ± 2.387 | 0.0000 |
| *Hirsutella sinensis* V.S. *Mortierella* SP | HexCer (t19:1/16:1) | 1.41 | 4.416 ± 0.619 | 0.056 ± 0.018 | 0.0000 |
| | Cer (d18:2/18:1) | 1.39 | 0.009 ± 0.005 | 0.543 ± 0.083 | 0.0000 |
| | SM (d14:1/20:0) | 1.35 | 11.618 ± 2.342 | 1.080 ± 0.410 | 0.0000 |
| *Hirsutella sinensis* V.S. *Gliocadium roseum* | Sa (d16:0) | 1.41 | 0.014 ± 0.006 | 0.211 ± 0.005 | 0.0000 |
| | Sa (t18:0) | 1.41 | 0.107 ± 0.049 | 4.544 ± 0.177 | 0.0000 |
| | Cer (d18:1/18:1) | 1.41 | 1.227 ± 0.845 | 13.455 ± 0.594 | 0.0000 |
| *Cordyceps sinensis* V.S. *Cephalosporium sinensis* | Sa (d16:0) | 1.56 | 12.732 ± 0.724 | 0.33 ± 0.174 | 0.0000 |
| | Cer (d19:2/16:0(OH)) | 1.56 | 10.203 ± 1.147 | 0.547 ± 0.802 | 0.0000 |
| | Cer (d18:1/16:1) | 1.55 | 11.865 ± 1.381 | 1.109 ± 0.309 | 0.0000 |
| *Cordyceps sinensis* V.S. *Mortierella* SP | Sa (d16:0) | 1.43 | 12.732 ± 0.724 | 0.068 ± 0.033 | 0.0000 |
| | Cer (d19:2/16:0(OH)) | 1.41 | 10.203 ± 1.147 | 3.820 ± 2.451 | 0.0001 |
| | Cer (d18:2/18:1) | 1.38 | 0.118 ± 0.035 | 0.543 ± 0.083 | 0.0000 |
| *Cordyceps sinensis* V.S. *Gliocadium roseum* | Cer (d18:1/18:1) | 1.28 | 0.446 ± 0.396 | 13.455 ± 0.594 | 0.0000 |
| | Sa (t18:0) | 1.28 | 0.674 ± 0.121 | 4.544 ± 0.177 | 0.0000 |
| | Sa (t18:0) isomer | 1.28 | 2.373 ± 0.210 | 10.881 ± 0.455 | 0.0000 |
| *Cephalosporium sinensis* V.S. *Mortierella* SP | Cer (d18:2/16:1) | 1.76 | 1.008 ± 0.299 | 2.350 ± 0.452 | 0.0000 |
| | Cer (d18:1/18:1) | 1.74 | 12.008 ± 2.387 | 3.823 ± 1.802 | 0.0000 |
| | So (d16:1) | 1.70 | 0.375 ± 0.223 | 1.317 ± 0.340 | 0.0000 |
| *Cephalosporium sinensis* V.S. *Gliocadium roseum* | Sa (t18:0) | 1.90 | 0.261 ± 0.121 | 4.544 ± 0.177 | 0.0000 |
| | So (t18:1) | 1.88 | 0.107 ± 0.062 | 0.929 ± 0.065 | 0.0000 |
| | Cer (d18:1/14:1) | 1.81 | 0.053 ± 0.016 | 0.141 ± 0.004 | 0.0000 |
| *Mortierella* SP V.S. *Gliocadium roseum* | Sa (t18:0) | 1.41 | 0.392 ± 0.096 | 4.544 ± 0.177 | 0.0000 |
| | So (t18:1) | 1.39 | 0.196 ± 0.078 | 0.929 ± 0.065 | 0.0000 |
| | Cer (d18:2/18:1) | 1.36 | 0.543 ± 0.083 | 0.029 ± 0.018 | 0.0000 |

The invention claimed is:

1. A method of identifying and optionally quantifying at least one sphingolipid in a *Cordyceps* sample, which method comprises steps of:
   a) preparing a test sample solution from a *Cordyceps* sample comprising a step of
      (i) extracting the *Cordyceps* sample with at least a first extracting solvent comprising an aliphatic alcohol;
      (ii) reconstituting the *Cordyceps* extract with a reconstitution solvent and
      (iii) filtering the reconstituted *Cordyceps* extract
   b) subjecting the test sample solution to liquid chromatography with a mobile phase comprising at least a first and a second eluting solvent, wherein the at least first and second eluting solvent comprise a mixture of at least one aliphatic alcohol, at least one carboxylic acid and at least one carboxylic acid salt and wherein the second eluting solvent has a higher total amount of aliphatic alcohol compared to the first eluting solvent; and
   c) performing a mass spectrometry following step b).

2. The method of claim 1, wherein the *Cordyceps* sample is used in step a) (i) in powdered form and wherein 20 mg to 80 mg of the powdered *Cordyceps* sample are used.

3. The method of claim 1, wherein the aliphatic alcohol in step a) (i) is a monohydric aliphatic alcohol containing one to four carbon atoms.

4. The method of claim 1, wherein step a) (i) further comprises extracting the *Cordyceps* sample with the first extraction solvent and, additionally, a second and a third extracting solvent, and wherein the first, second and third extracting solvents each comprise a monohydric aliphatic alcohol containing one to four carbon atoms for obtaining a *Cordyceps* extract.

5. The method of claim 4, wherein the first extracting solvent comprises chloroform and methanol, the second extracting solvent comprises chloroform and methanol, and the third extracting solvent comprises chloroform, methanol and water and wherein the volume ratio of chloroform to methanol in the first extracting solvent is less than 1:1 (v/v) and wherein the volume ratio of chloroform to methanol in the second extracting solvent is above 1:1 (v/v) and wherein the volume ratio of chloroform to methanol in the third extracting solvent is above 2:1 (v/v).

6. The method of claim 4, wherein step a) (i) comprises mixing the *Cordyceps* sample with the first extracting solvent, the first extracting solvent comprising chloroform and methanol in a ratio of chloroform to methanol of less than 1:1 (v/v);
   subjecting the mixture of the *Cordyceps* sample and the first extracting solvent to ultrasonication;
   incubating the ultrasonicated mixture at more than 30° C.;
   adding an alkali hydroxide after said step of incubating to created an alkalized mixture;
   further incubating the alkalized mixture at least at 30° C. and subsequently neutralizing the alkalized mixture with a carboxylic acid to create a neutralized mixture;
   subjecting the neutralized mixture to centrifugation to obtain a first supernatant and a first residue;
   contacting the first residue with the second extracting solvent, the second extracting solvent comprising chloroform and methanol in a ratio of chloroform to methanol of more than 1:1 (v/v) to obtain a second residue and a second supernatant;
   contacting the second residue with the third extracting solvent, the third extracting solvent comprising chloroform and methanol in a ratio of chloroform to methanol of more than 2:1 (v/v) and water, whereby a lower and upper layer is formed;
   combining the first supernatant, the second supernatant and the lower layer; and
   removing the first, second, and third extracting solvents to form the *Cordyceps* extract.

7. The method of claim 4, wherein the reconstitution solvent in step (ii) is methanol.

8. The method of claim 4, wherein the filtration in step (iii) is carried out with a filter having a pore size of at most 0.30 μm.

9. The method of claim 1, wherein the liquid chromatography in step b) is an ultrahigh pressure liquid chromatography and wherein a $C_{18}$ column is used as stationary phase.

10. The method of claim 1, wherein the first eluting solvent comprises methanol, water, formic acid and ammonium acetate and the second eluting solvent comprises methanol, isopropanol, formic acid and ammonium acetate.

11. The method of claim 10, wherein the first eluting solvent comprises methanol, water, formic acid (60:40:0.2, v/v/v) and 10 mM ammonium acetate and the second eluting solvent comprises methanol, isopropanol, formic acid (60:40:0.2, v/v/v) and 10 mM ammonium acetate and wherein a linear gradient is applied with increasing amounts of the second eluting solvent.

12. The method of claim 1, wherein the mass spectrometry includes the application of a Q-TOF mass spectrometry.

13. The method of claim 1, wherein the mass spectrometry includes the application of a QQQ mass spectrometry.

14. The method of claim 1, wherein step c) is performed by a mass spectrometer operating in a MS/MS mode.

15. A method of identifying wild-type *Cordyceps* in a *Cordyceps* sample comprising steps of:
   a) identifying and quantifying the sphingolipid portion in a *Cordyceps* sample with the method as claimed in claim 1;
   b) determining at least a first and a second *Cordyceps* wild-type indicative parameter;
   c) comparing the at least first and second *Cordyceps* wild-type indicative parameter with reference values;
   wherein an at least first and second *Cordyceps* wild-type indicative parameter corresponding to the reference values indicates that the *Cordyceps* sample comprises wild-type *Cordyceps;*
   and wherein the first *Cordyceps* wild-type indicative parameter is the ratio of ceramides to sphingoid bases, wherein the reference value for the first *Cordyceps* wild-type indicative parameter is an amount of ceramides of at least 10 wt.-% and less than 100 wt.-% relative to the amount of sphingoid bases; and
   wherein the second *Cordyceps* wild-type indicative parameter is the ratio of glycosphingolipids to phosphosphingolipids and wherein the reference value for the second *Cordyceps* wild-type indicative parameter is an amount of glycosphingolipids of at most 80 wt.-% relative to the amount of phosphosphingolipids.

16. The method of claim 15, wherein in step a) the liquid chromatography is an ultrahigh pressure liquid chromatography and wherein the mass spectrometry includes Q-TOF mass spectrometry and/or QQQ mass spectrometry.

17. The method of claim 15, wherein the reference value for the first *Cordyceps* wild-type indicative parameter is an amount of ceramides of at least 15 wt.-% and at most 85 wt.-% relative to the amount of sphingoid bases; and wherein the reference value for the second *Cordyceps* wild-type indicative parameter is an amount of glycosphingolipids which is at least 5 wt.-% and at most 50 wt.-% relative to the amount of phosphosphingolipids.

18. The method of claim 15, wherein a further *Cordyceps* wild-type indicative parameter is determined in step b) which further *Cordyceps* wild-type indicative parameter is the ratio of phosphosphingolipids to ceramides and wherein the reference value in step c) for said further *Cordyceps* wild-type indicative parameter is an amount of phosphosphingolipids which is at least 50 wt.-% and at most 110 wt.-% relative to the amount of ceramides.

19. The method of claim 15, wherein a further *Cordyceps* wild-type indicative parameter is determined in step b) which further *Cordyceps* wild-type indicative parameter is the ratio of sphinganines to sphingosines and wherein the reference value in step c) for said further *Cordyceps* wild-type indicative parameter is that the amount of sphinganines is between 20 wt.-% to 70 wt.-% relative to the amount of sphingosines.

20. The method of claim 15, wherein a further *Cordyceps* wild-type indicative parameter is determined in step b) which further *Cordyceps* wild-type indicative parameter is the amount of each of HexCer (t19:1/16:1), Sa (d16:0), SM (d18:2/16:0(OH)), Cer (d18:0/16:1) and Cer (d18:1/18:1), wherein the reference value in step c) for said further *Cordyceps* wild-type indicative parameter is that the amount of HexCer (t19:1/16:1) is at most 3 pmol/mg, of Sa (d16:0) is at most 1 pmol/mg, of SM (d18:2/16:0(OH)) is at least 0.2 pmol/mg, of Cer (d18:0/16:1) is at most 0.4 pmol/mg and of Cer (d18:1/18:1) is at most 1 pmol/mg of the *Cordyceps* sample.

* * * * *